US008788057B2

(12) United States Patent
Stevenson et al.

(10) Patent No.: US 8,788,057 B2
(45) Date of Patent: Jul. 22, 2014

(54) MULTIPLEXER FOR SELECTION OF AN MRI COMPATIBLE BANDSTOP FILTER PLACED IN SERIES WITH A PARTICULAR THERAPY ELECTRODE OF AN ACTIVE IMPLANTABLE MEDICAL DEVICE

(75) Inventors: Robert A. Stevenson, Canyon Country, CA (US); Gabriel A. Kustra, Cheektowaga, NY (US)

(73) Assignee: Greatbatch Ltd., Clarence, NY (US)

( * ) Notice: Subject to any disclaimer, the term of this patent is extended or adjusted under 35 U.S.C. 154(b) by 709 days.

(21) Appl. No.: 12/817,030

(22) Filed: Jun. 16, 2010

(65) Prior Publication Data

US 2010/0318160 A1 Dec. 16, 2010

Related U.S. Application Data

(63) Continuation of application No. 12/337,376, filed on Dec. 17, 2008, which is a continuation-in-part of application No. 12/337,170, filed on Dec. 17, 2008.

(60) Provisional application No. 61/079,693, filed on Jul. 10, 2008, provisional application No. 61/016,364, filed on Dec. 21, 2007.

(51) Int. Cl.
*A61N 1/37* (2006.01)
*A61N 1/04* (2006.01)

(52) U.S. Cl.
USPC .............................................. 607/63; 607/116

(58) Field of Classification Search
USPC ................................................... 607/2, 9, 63
See application file for complete search history.

(56) References Cited

U.S. PATENT DOCUMENTS

| 3,842,374 A | 10/1974 | Schlicke |
| 4,021,759 A | 5/1977 | Campi |
| 4,440,172 A | 4/1984 | Langer |
| 4,745,923 A | 5/1988 | Wonstrom |
| 5,170,806 A | 12/1992 | Colen |
| 5,217,010 A * | 6/1993 | Tsitlik et al. ...................... 607/9 |
| 5,266,079 A | 11/1993 | Iga |
| 5,336,253 A | 8/1994 | Gordon et al. |
| 5,369,390 A | 11/1994 | Lin et al. |
| 5,475,353 A | 12/1995 | Roshen et al. |
| 5,531,782 A | 7/1996 | Kroll et al. |
| 5,545,183 A | 8/1996 | Altman |
| 5,578,976 A | 11/1996 | Yao |
| 5,772,689 A | 6/1998 | Kroll |
| 5,797,970 A | 8/1998 | Pouvreau |
| 5,836,992 A | 11/1998 | Thompson et al. |
| 5,870,273 A | 2/1999 | Sogabe et al. |

(Continued)

OTHER PUBLICATIONS

Luecke, Gerald. "Analog and Digital Circuits for Electronic Control System Applications: Using the TI MSP430 Microcontroller." Burlington: Newnes, 2005. Print.*

(Continued)

*Primary Examiner* — Allen Porter, Jr.
(74) *Attorney, Agent, or Firm* — Michael F. Scalise

(57) ABSTRACT

An MRI-compatible electronic medical therapy system includes an active medical device connected to a plurality of electrodes. A multiplexer circuit includes at least one circuit protection device in electrical series with the electrodes and the medical device. The circuit protection device is adapted to permit current flow therethrough during normal medical device related therapy, but substantially prevent current flow therethrough in the presence of an induced electromagnetic field.

9 Claims, 32 Drawing Sheets

(56) References Cited

U.S. PATENT DOCUMENTS

| | | | |
|---|---|---|---|
| 5,968,086 | A | 10/1999 | Bonner et al. |
| 5,999,398 | A | 12/1999 | Maki |
| 6,160,230 | A | 12/2000 | McMillan et al. |
| 6,218,911 | B1 | 4/2001 | Kong et al. |
| 6,327,498 | B1 | 12/2001 | Kroll |
| 6,351,368 | B1 | 2/2002 | Kim |
| 6,373,007 | B1 | 4/2002 | Calcatera et al. |
| 6,418,348 | B1 | 7/2002 | Witte |
| 6,459,935 | B1 | 10/2002 | Piersma |
| 6,944,489 | B2 | 9/2005 | Zeijlemaker et al. |
| 6,985,347 | B2 | 1/2006 | Stevenson et al. |
| 6,985,775 | B2 | 1/2006 | Reinke et al. |
| 6,999,818 | B2 | 2/2006 | Stevenson et al. |
| 7,305,270 | B1 | 12/2007 | Kroll et al. |
| 2002/0095187 | A1 | 7/2002 | Thompson et al. |
| 2002/0103523 | A1 | 8/2002 | Helland |
| 2003/0083726 | A1* | 5/2003 | Zeijlemaker et al. ......... 607/122 |
| 2004/0220650 | A1 | 11/2004 | Houben et al. |
| 2005/0043768 | A1* | 2/2005 | Goode ............................ 607/32 |
| 2005/0115811 | A1 | 6/2005 | Receveur et al. |
| 2005/0222657 | A1* | 10/2005 | Wahlstrand et al. .......... 607/116 |
| 2006/0122679 | A1 | 6/2006 | Wengreen et al. |
| 2006/0212096 | A1 | 9/2006 | Stevenson |
| 2006/0247684 | A1 | 11/2006 | Halperin et al. |
| 2007/0112398 | A1 | 5/2007 | Stevenson et al. |
| 2007/0173909 | A1 | 7/2007 | Inman et al. |
| 2007/0255332 | A1 | 11/2007 | Cabelka et al. |
| 2008/0049376 | A1 | 2/2008 | Stevenson et al. |
| 2008/0065181 | A1 | 3/2008 | Stevenson |
| 2008/0116997 | A1 | 5/2008 | Dabney et al. |
| 2008/0132987 | A1 | 6/2008 | Westlund et al. |
| 2008/0183230 | A1 | 7/2008 | Kemmetmueller et al. |
| 2008/0195180 | A1 | 8/2008 | Stevenson et al. |
| 2009/0149906 | A1 | 6/2009 | Ameri et al. |

OTHER PUBLICATIONS

European Patent Office, European Search Report re App. No. EP 09014024.5, Mar. 29, 2010.

Roger Christoph Luchinger, "Safety Aspects of Cardiac Pacemakers in Magnetic Resonance Imaging," dissertation, Swiss Federal Institute of Technology, Zurich, 2002, Zurich, Switzerland.

European Patent Office, Partial European Search Report re App. No. EP 09014027, Feb. 23, 2010.

S. Gabriel, R. W. Lau and C. Gabriel, "The dielectric properties of biological tissues: II. Measurements in the frequency range 10 Hz to 20 GHz," Phys. Med. Biol., 1996, pp. 2251-2269, vol. 41, IOP Publishing Ltd, United Kingdom.

Constantine A. Balanis, "Advanced Engineering Electromagnetics," Arizona State University, John Wiley & Sons, New York.

C. Gabriel, S. Gabriel and E. Corthout, "The dielectric properties of biological tissues: I. Literature survey," Phys. Med. Biol., 1996, pp. 2231-2249, vol. 41, IOP Publishing Ltd., United Kingdom.

S. Gabriel, R.W. Lau and C. Gabriel, "The dielectric properties of biological tissues: III. Parametric models for the dielectric spectrum of tissues," Phys. Med. Biol., 1996, pp. 2271-2293, vol. 41, IOP Publishing Ltd., United Kingdom.

* cited by examiner

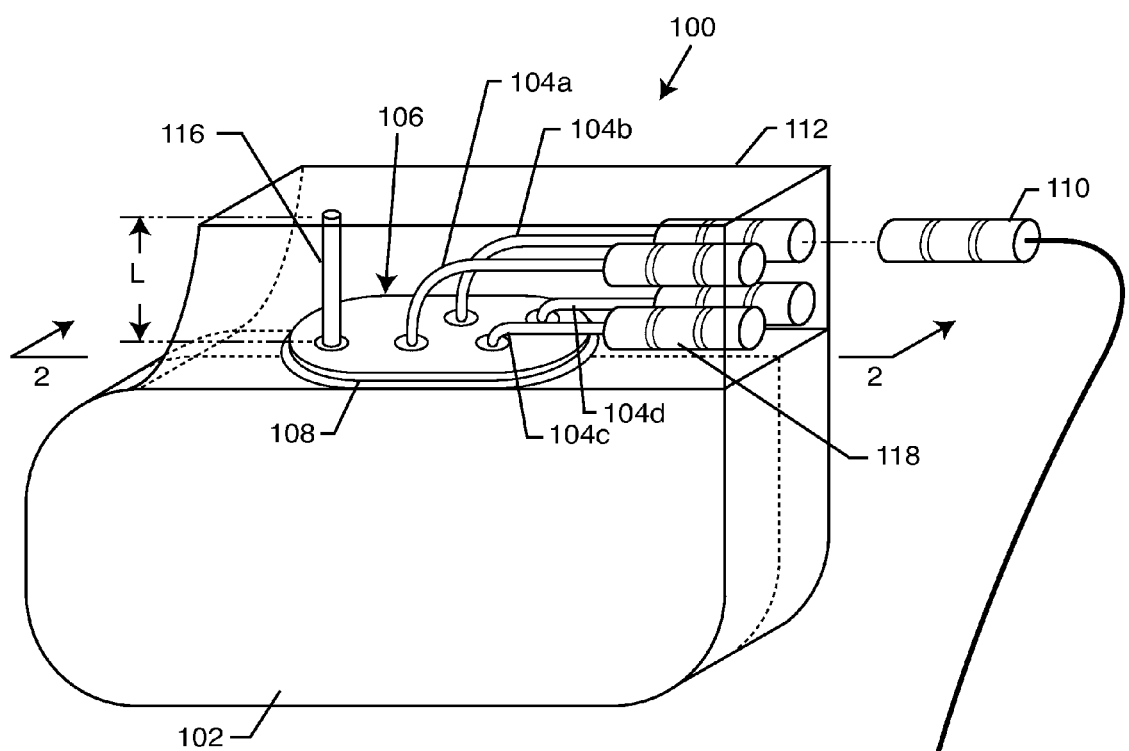
FIG. 2
PRIOR ART
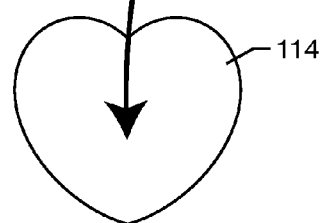

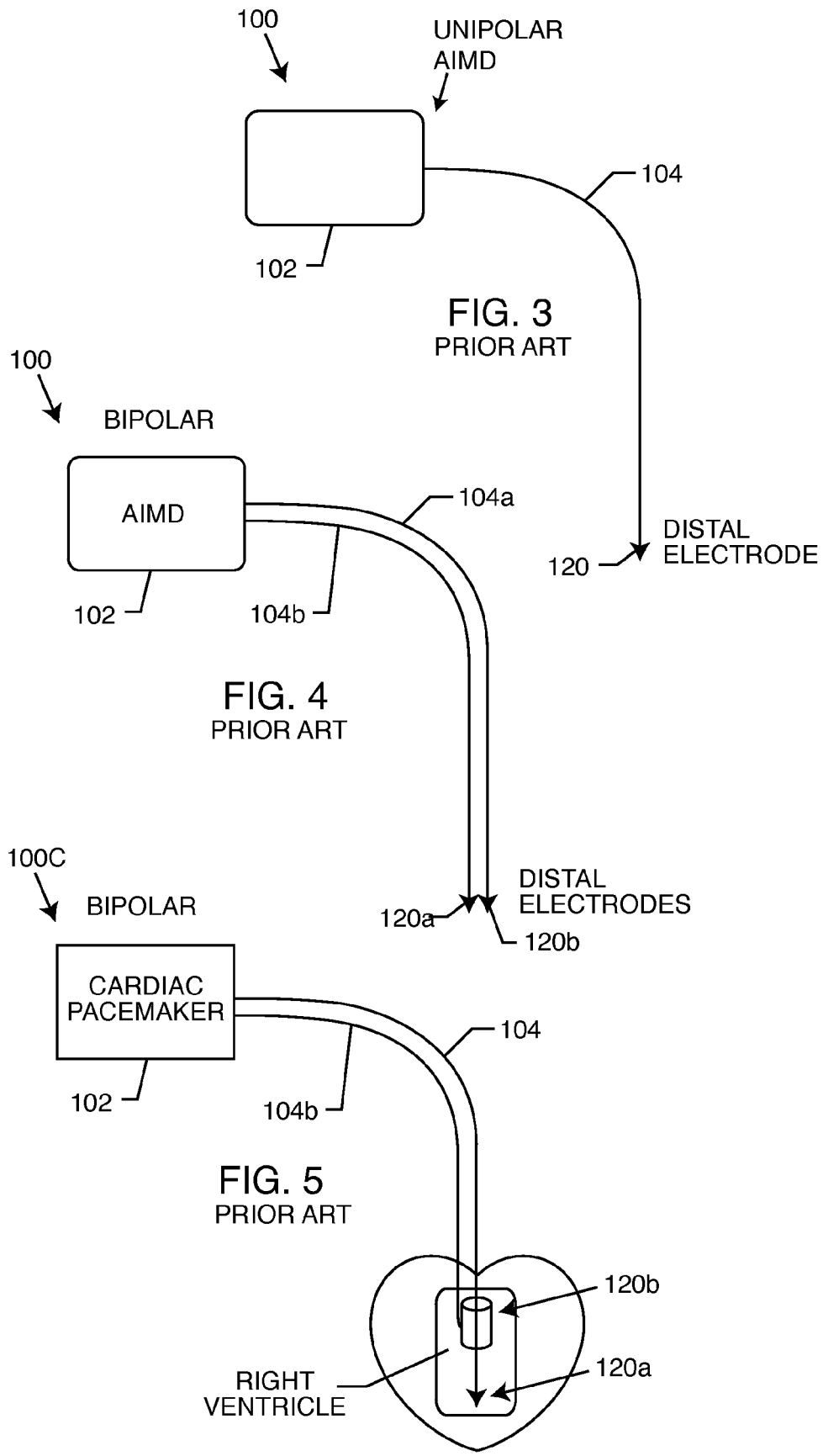

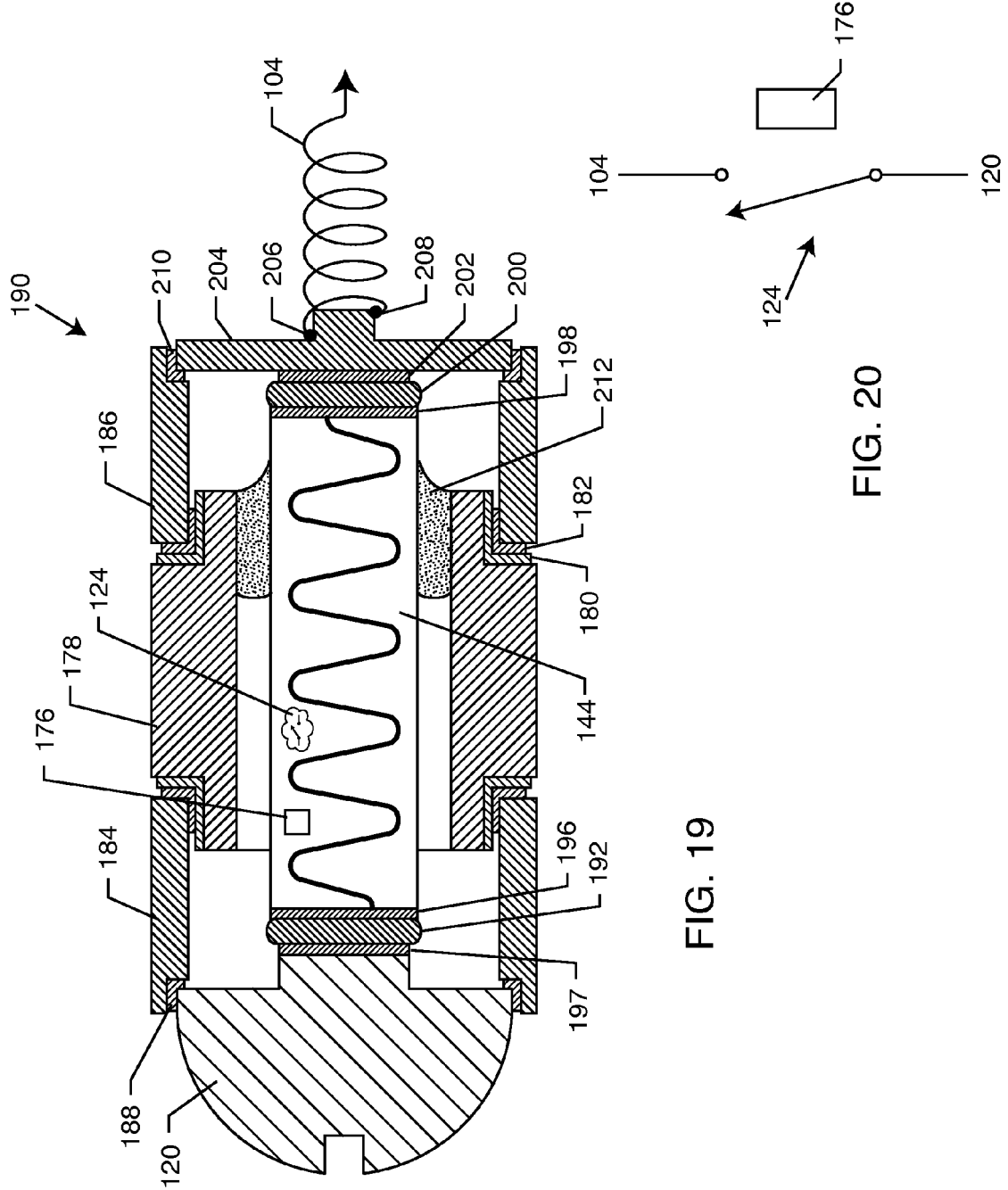

| French Guage | Diameter (mm) | Diameter (inches) |
|---|---|---|
| 3 | 1 | 0.039 |
| 4 | 1.35 | 0.053 |
| 5 | 1.67 | 0.066 |
| 6 | 2 | 0.079 |
| 7 | 2.3 | 0.092 |
| 8 | 2.7 | 0.105 |
| 9 | 3 | 0.118 |
| 10 | 3.3 | 0.131 |
| 11 | 3.7 | 0.144 |
| 12 | 4 | 0.158 |
| 13 | 4.3 | 0.170 |
| 14 | 4.7 | 0.184 |
| 15 | 5 | 0.197 |
| 16 | 5.3 | 0.210 |
| 17 | 5.7 | 0.223 |
| 18 | 6 | 0.236 |
| 19 | 6.3 | 0.249 |
| 20 | 6.7 | 0.263 |
| 22 | 7.3 | 0.288 |
| 24 | 8 | 0.315 |
| 26 | 8.7 | 0.341 |
| 28 | 9.3 | 0.367 |
| 30 | 10 | 0.393 |
| 32 | 10.7 | 0.419 |
| 34 | 11.3 | 0.455 |

FIG. 32

MULTIPLEXER FOR SELECTION OF AN MRI COMPATIBLE BANDSTOP FILTER PLACED IN SERIES WITH A PARTICULAR THERAPY ELECTRODE OF AN ACTIVE IMPLANTABLE MEDICAL DEVICE

BACKGROUND OF THE INVENTION

This invention relates generally to electronic switches and switch assemblies adapted for use in active implantable medical devices (AIMDs) such as cardiac pacemakers, cardioverter defibrillators, neurostimulators and the like. The normally closed electronic switch is designed to be selectively open just prior to and during exposure of the medical device to diagnostic, therapy, electrocautery surgical procedures, or imaging such as magnetic resonance imaging (MRI). Disconnecting a distal tip electrode(s), by opening an electronic switch eliminates the possibility that undesirable RF currents could overheat said distal electrode and undesirably flow into body tissue thereby creating the potential for tissue damage (necrosis). For MRI imaging, opening the electronic switch eliminates problems associated with low frequency gradient fields as well as high frequency pulsed RF fields. The present invention is also applicable to a wide range of external medical devices, including externally worn drug pumps, EKG/ECG electrodes, neurostimulators, ventricular assist devices and the like, as well as a wide range of probes, catheters, monitoring lead wires and the like, that may be temporarily inserted into or onto a patient or that a patient may be wearing or connected to during medical diagnostic procedures such as MRI.

Compatibility of cardiac pacemakers, implantable defibrillators and other types of active implantable medical devices with magnetic resonance imaging (MRI) and other types of hospital diagnostic equipment has become a major issue. If one goes to the websites of major cardiac pacemaker manufacturers in the United States, one will see that the use of MRI is generally contra-indicated with pacemakers and implantable defibrillators. A similar contra-indication is found in the manuals of MRI equipment manufacturers such. See also "Safety Aspects of Cardiac Pacemakers in Magnetic Resonance Imaging", a dissertation submitted to the Swiss Federal Institute of Technology Zurich presented by Roger Christoph Lüchinger. Dielectric Properties of Biological Tissues: I. Literature Survey", by C. Gabriel, S. Gabriel and E. Cortout; "Dielectric Properties of Biological Tissues: II. Measurements and the Frequency Range 0 Hz to 20 GHz", by S. Gabriel, R. W. Lau and C. Gabriel; "Dielectric Properties of Biological Tissues: III. Parametric Models for the Dielectric Spectrum of Tissues", by S. Gabriel, R. W. Lau and C. Gabriel; and "Advanced Engineering Electromagnetics, C. A. Balanis, Wiley, 1989, all of which are incorporated herein by reference.

However, an extensive review of the literature indicates that MRI is indeed often used with pacemaker patients in spite of the contra indications. The safety and feasibility of MRI in patients with cardiac pacemakers is an issue of increasing significance. The effects of MRI on patients' pacemaker systems have only been analyzed retrospectively in some case reports. There are a number of papers that indicate that MRI on new generation pacemakers can be conducted up to 0.5 Tesla (T). Other papers go up to 1.5 T for non-pacemaker dependent patients under highly controlled conditions.

MRI is one of medicine's most valuable diagnostic tools. MRI is, of course, extensively used for imaging, but is also increasingly used for real-time procedures such as interventional medicine (surgery). In addition, MRI is used in real time to guide ablation catheters, neurostimulator tips, deep brain probes and the like. An absolute contra-indication for pacemaker patients means that pacemaker and ICD wearers are excluded from MRI. This is particularly true of scans of the thorax and abdominal areas. However, because of MRI's incredible value as a diagnostic tool for imaging organs and other body tissues, many physicians simply take the risk and go ahead and perform MRI on a pacemaker patient. The literature indicates a number of precautions that physicians should take in this case, including limiting the applied power of the MRI in terms of the specific absorption rate (SAR), programming the pacemaker to fixed or asynchronous pacing mode, having emergency personnel and resuscitation equipment standing by (known as "Level II" protocol), and careful reprogramming and evaluation of the pacemaker and patient after the procedure is complete. There have been reports of latent problems with cardiac pacemakers after an MRI procedure occurring many days later (such as increase in or loss of pacing pulse capture).

There are three types of electromagnetic fields used in an MRI unit. The first type is the main static magnetic field designated $B_0$ which is used to align protons in body tissue. The field strength varies from 0.5 to 3.0 Tesla in most of the currently available MRI units in clinical use. Some of the newer MRI system fields can go as high as 4 to 6 Tesla. At the recent International Society for Magnetic Resonance in Medicine (ISMRIM) conference, which was held on 5 and 6 Nov. 2005, it was reported that certain research systems are going up as high as 11.7 Tesla. A 1.5 T MRI system is over 100,000 times the magnetic field strength of the earth. A static magnetic field of this magnitude can induce powerful magnetomechanical forces on any magnetic materials implanted within the patient, including certain components within the cardiac pacemaker and/or lead wire systems themselves. It is unlikely that the static MRI magnetic field can induce currents (dB/dt) into the pacemaker lead wire system and hence into the pacemaker itself. It is a basic principle of physics that a magnetic field must either be time-varying as it cuts across the conductor (dB/dt), or the conductor itself must move within the magnetic field for currents to be induced (dB/dx).

The second type of field produced by magnetic resonance imaging equipment is the pulsed RF field which is generated by the body coil or head coil, also referred to as $B_1$. This is used to change the energy state of the protons and illicit MRI signals from tissue. The RF field is homogeneous in the central region and has two main components: (1) the magnetic field is circularly polarized in the actual plane; and (2) the electric field is related to the magnetic field by Maxwell's equations. In general, the RF field is switched on and off during measurements and usually has a frequency of 21 MHz to 64 MHz to 128 MHz depending upon the static magnetic field strength. The frequency of the RF pulse varies with the field strength of the main static field, as expressed in the Lamour Equation: RF PULSED FREQUENCY (in MHz)= (42.56) (STATIC FIELD STRENGTH (T); where 42.56 MHz per Tesla is the Lamour constant for H+ protons.

The third type of electromagnetic field is the time-varying magnetic gradient field designated Gx, Gy, Gz which is used for spatial localization. The gradient field changes its strength along different orientations and operating frequencies on the order of 1 to 2.2 kHz. The vectors of the magnetic field gradients in the X, Y and Z directions are produced by three sets of orthogonally positioned coils and are switched on only during the measurements. In some cases, the gradient field has been shown to elevate natural heart rhythms (heart beat). This is not completely understood, but it is a repeatable phenomenon. There have been some reports of gradient field induced ventricular arrhythmias which could be life threatening. The Gz gradient is used to distort the $B_o$ field in the z direction, thereby creating body 'slices' of specific thickness. The Gx and Gy fields are used to introduce phase and frequency 'markers' to specific protons, allowing for an x-y image to be generated.

The gradient fields operate at roughly 1 to 2.2 kHz, and are generated by three distinct, orthogonally oriented coils. These fields are only active during image generation protocols, and have been shown to have adverse effects on human physiology. These effects are largely due to the induced voltages that are generated by the application of a moving magnetic field on a large area. Faraday's Law of Induction is expressed as:

$$V = A\frac{dB}{dt},$$

where A is the area of the loop, and dB/dt is change in magnetic flux with respect to time. It has been shown that the induced voltages generated by the gradient fields, if high enough, can induce peripheral nerve stimulation (PNS). This has been reported in literature as a sensation of pain or other discomfort while running relatively high MRI gradients. In more extreme animal testing, cardiac stimulation has been detected, although this has taken roughly 80 times more energy to achieve than that of PNS. To prevent PNS or cardiac stimulation from occurring, industry standards have limited dB/dt to roughly 20 T/sec. Placing an electronic switch in accordance with the present invention at or near the distal tip electrode eliminates any chance that gradient currents will be able to stimulate or capture body tissues.

Of interest is the effect of the gradient fields on AIMDs, which typically have implanted lead systems. In the case of AIMDs with unipolar lead systems, a circuit loop is formed between the AIMD housing or can, the lead system, the distal TIP, and body tissue (as the return path). An average area created by such a loop is around 225 cm² with the higher limit about 350 cm². When considering this with the 20 T/sec maximum, it can be seen that the maximum induced voltage in the loop is 0.700V. When one looks at the induced voltage at the pacing tip, it is typically an order of magnitude lower than the induced voltage in the loop (due to relatively high lead system and device impedances). This is much lower than the typical pacing threshold required for an AIMD to stimulate heart tissue.

It is instructive to note how voltages and EMI are induced into an implanted or external lead wire system. At very low frequency (VLF), voltages are induced at the input to the cardiac pacemaker as currents circulate throughout the patient's body and create differential voltage drops. In a unipolar system, because of the vector displacement between the pacemaker housing and, for example, the TIP electrode, voltage drop across body tissues may be sensed due to Ohms Law and the circulating RF signal. At higher frequencies, the implanted lead wire systems actually act as antennas where currents are induced along their length. These antennas are not very efficient due to the damping effects of body tissue; however, this can often be offset by extremely high power fields and/or body resonances. At very high frequencies (such as cellular telephone frequencies), electromagnetic interference (EMI) signals are induced only into the first area of the lead wire system (for example, at the header block of a cardiac pacemaker). This has to do with the wavelength of the signals involved and where they couple efficiently into the system.

Placing an electronic switch in accordance with the present invention inside or near the housing of the AIMD eliminates any possibility that the EMI from Gradient fields may disrupt or interfere with AIMD electronic circuits. An added benefit is that MRI RF currents are also eliminated in the area near the AIMD which, for example, in a pacemaker application eliminates the risk of esophageal ablation due to overheating of adjacent lead wires.

Magnetic field coupling into an implanted lead wire system is based on loop areas. For example, in a cardiac pacemaker, there is a loop formed by the lead wire as it comes from the cardiac pacemaker housing to its distal TIP located in the right ventricle. The return path is through body fluid and tissue generally straight from the TIP electrode in the right ventricle back up to the pacemaker casing or housing. This forms an enclosed area which can be measured from patient X-rays in square centimeters. The average loop area is 200 to 225 cm. This is an average and is subject to great statistical variation. For example, in a large adult patient with an abdominal implant, the implanted loop area is much larger (greater than 450 cm²).

Relating now to the specific case of MRI, the magnetic gradient fields would be induced through enclosed loop areas. However, the pulsed RF fields, which are generated by the body coil, would be primarily induced into the lead wire system by antenna action. By careful placement of the novel electronic switch of the present invention, both MRI gradient and RF currents are eliminated.

There are a number of other potential problems with MRI, including:

(1) Closure of the pacemaker reed switch. A pacemaker reed switch, which can also be a Hall Effect device, is designed to detect a permanent magnet held close to the patient's chest. This magnet placement allows a physician or even the patient to put the implantable medical device into what is known as the "magnet mode response." The "magnet mode response" varies from one manufacturer to another, however, in general, this puts the pacemaker into a fixed rate or asynchronous pacing mode. This is normally done for short times and is very useful for diagnostic purposes. However, when a pacemaker is brought close to the MRI scanner, the MRI static field can make the pacemaker's internal reed switch close, which puts the pacemaker into a fixed rate or asynchronous pacing mode. Worse yet, the reed switch may bounce or oscillate. Asynchronous pacing may compete with the patient's underlying cardiac rhythm. This is one reason why pacemaker/ICD patients have generally been advised not to undergo MRI. Fixed rate or asynchronous pacing for most patients is not an issue. However, in patients with unstable conditions, such as myocardial ischemia, there is a substantial risk for life threatening ventricular fibrillation during asynchronous pacing. In most modern pacemakers the magnetic reed switch (or Hall Effect device) function is programmable. If the magnetic reed switch response is switched off, then synchronous pacing is still possible even in strong magnetic fields. The possibility to open and re-close the reed switch in the main magnetic field by the gradient field cannot be excluded. However, it is generally felt that the reed switch will remain closed due to the powerful static magnetic field. It is theoretically possible for certain reed switch orientations at the gradient field to be capable of repeatedly closing and re-opening the reed switch. Careful placement of the novel electronic switches of the present invention disconnect AIMD therapy delivery. Accordingly, it will not matter what the AIMD reed or Hall effect switch does during MRI scans as the intermittent synchronous/asynchronous pacing effects will not be able to reach body tissue. This is another important advantage of the present invention.

(2) Reed switch damage. Direct damage to the reed switch is theoretically possible, but has not been reported in any of the known literature. In an article written by Roger Christoph Lüchinger of Zurich, he reports on testing in which reed switches were exposed to the static magnetic field of MRI equipment. After extended exposure to these static magnetic fields, the reed switches functioned normally at close to the same field strength as before the test. However, it is still important for the physician to check the proper operation of the reed switch and the AIMD after MRI scans are complete.

(3) Pacemaker displacement. Some parts of pacemakers, such as the batteries and reed switches, contain ferrous magnetic materials and are thus subject to mechanical forces during MRI (testing is done to ASTM Standards). Pacemaker displacement may occur in response to magnetic force or magnetic torque (newer pacemakers and ICDs have less ferrous materials and are less susceptible to this). With the much smaller sizes of modern AIMDS, most experts now report that force and torques due to MRI are now negligible.

(4) Radio frequency field. At the pulsed RF frequencies of interest in MRI, RF energy can be absorbed and converted to heat. The power deposited by RF pulses during MRI is complex and is dependent upon the power, duration and shape of the RF pulse, the relative long term time averages of the pulses, the transmitted frequency, the number of RF pulses applied per unit time, and the type of configuration of the RF transmitter coil used. Specific absorption rate (SAR) is a measure of how much energy is induced into body tissues. The amount of heating also depends upon the volume of the various tissue (i.e. muscle, fat, etc.) imaged, the electrical resistivity of tissue and the configuration of the anatomical region imaged. There are also a number of other variables that depend on the placement in the human body of the AIMD and its associated lead wire(s). For example, it will make a difference how much current is induced into a pacemaker lead wire system as to whether it is a left or right pectoral implant. In addition, the routing of the lead and the lead length are also very critical as to the amount of induced current and heating that would occur. Also, distal TIP design is very important as the distal TIP itself can act as its own antenna. Location within the MRI bore is also important since the electric fields required to generate the RF increase exponentially as the patient is moved away from MRI bore center-line (ISO center). The cause of heating in an MRI environment is two fold: (a) RF field coupling to the lead can occur which induces significant local heating; and (b) currents induced during the RF transmission can flow into body tissue and cause local Ohm's Law heating next to the distal TIP electrode of the implanted lead. The RF field in an MRI scanner can produce enough energy to induce lead wire currents sufficient to destroy some of the adjacent myocardial tissue. Tissue ablation has also been observed. The effects of this heating are not readily detectable during the MRI. Indications that heating has occurred would include an increase in pacing threshold, venous ablation, Larynx ablation, myocardial perforation and lead penetration, or even arrhythmias caused by scar tissue. Such long term heating effects of MRI have not been well studied yet. Placing an electronic switch in accordance with the present invention at or near the distal electrode stops the flow of MRI RF currents and therefore minimizes or altogether eliminates the above concerns.

(5) Alterations of pacing rate due to the applied radio frequency field. It has been observed that the RF field may induce undesirable fast cardiac pacing (QRS complex) rates. There are various mechanisms which have been proposed to explain rapid pacing: direct tissue stimulation, interference with pacemaker electronics or pacemaker reprogramming (or reset). In all of these cases, placing an electronic switch in accordance with the present invention at or near the distal electrode and at or near the AIMD stops the flow of MRI RF currents and therefore eliminates all of the above concerns. Placing electronic switches in accordance with present invention in series with the leads at the points of lead wire ingress and egress into the AIMD housing (at the device feedthrough EMI filter) prevents MRI RF fields from entering the AIMD housing and therefore provides a very high degree of protection to AIMD electronics. When used in combination with the AIMD EMI filters, this will make alterations in pacemaker pacing rate and/or pacemaker reprogramming much more unlikely.

(6) Time-varying magnetic gradient fields. The contribution of the time-varying gradient to the total strength of the MRI magnetic field is negligible; however, pacemaker systems could be affected because these fields are rapidly applied and removed. The time rate of change of the magnetic field is directly related to how much electromagnetic force (EMF) and hence current can be induced into a lead wire system. Lüchinger reports that even using today's gradient systems with a time-varying field up to 60 Tesla per second, the induced currents are likely to stay below the biological thresholds for cardiac fibrillation. A theoretical upper limit for the induced voltage by the time-varying magnetic gradient field is 20 volts. Such a voltage during more than 0.1 milliseconds could be enough energy to directly pace the heart. The placement of an electronic switch in accordance with the present invention at or near the distal electrode eliminates such concerns.

(7) Heating. Currents induced by time-varying magnetic gradient fields may lead to local heating. Researchers feel that the calculated heating effect of the gradient field is much less as compared to that caused by the RF field and therefore may be neglected.

There are additional problems possible with implantable cardioverter defibrillators (ICDs), another type of AIMD. ICDs use different and larger batteries which could cause higher magnetic forces. The programmable sensitivity in ICDs is normally much higher than it is for pacemakers; therefore, ICDs may falsely detect a ventricular tachyarrhythmia and inappropriately deliver therapy. In this case, therapy might include anti-tachycardia pacing, cardioversion or defibrillation (high voltage shock) therapies. MRI magnetic fields may prevent detection of a dangerous ventricular arrhythmia or fibrillation. There can also be heating problems of ICD leads which are expected to be comparable to those of pacemaker leads. Ablation of vascular walls is another concern. There have also been reports of older model ICDs being severely effected by the MRI pulsed RF field. In these cases, there have been multiple microprocessor resets and even cases of permanent damage where the ICD failed to function after the MRI procedure. In addition, ICDs have exhibited a different type of problem when exposed to MRI fields. That is, during an MRI exposure, the ICD might inappropriately sense the MRI RF field or gradient fields as a dangerous ventricular arrhythmia. In this case, the ICD will attempt to charge its high energy storage capacitor and deliver a high voltage shock to the heart. However, within this charging circuit, there is a transformer that is necessary to function in order to fully charge up the high energy storage capacitor. In the presence of the main static field ($B_O$) field, the ferrite core of this transformer tends to saturate thereby reducing its efficiency. This means the high energy storage capacitor cannot fully charge. Reports of repeated low voltage shocks are in the literature. These repeated shocks and this inefficient attempt to charge the battery can cause premature battery depletion of the ICD. Shortening of battery life is, of course, a highly undesirable condition. Placing electronic switches in accordance with the present invention at or near the distal electrodes and in series with the lead wires at the ICD housing turns off both sensing and therapy delivery which eliminates all of the above concerns.

In summary, there are a number of studies that have shown that MRI patients with active implantable medical devices, such as cardiac pacemakers, can be at risk for potential hazardous effects. However, there are a number of anecdotal reports that MRI can be safe for extremity imaging of pacemaker patients (i.e. the AIMD is outside the bore). These anecdotal reports are of interest; however, they are certainly not scientifically convincing that all MRI can be safe. As previously mentioned, just variations in the pacemaker lead wire length can significantly affect how much heat is generated.

From the layman's point of view, this can be easily explained by observing the typical length of the antenna on a cellular telephone compared to the vertical rod antenna more common on older automobiles. The relatively short antenna on the cell phone is designed to efficiently couple with the very high frequency wavelengths (approximately 950 MHz) of cellular telephone signals. In a typical AM and FM radio in an automobile, these wavelength signals would not efficiently couple to the relatively short antenna of a cell phone. This is why the antenna on the automobile is relatively longer.

An analogous situation exists on the MRI system. If one assumes, for example, a 3.0 Tesla MRI system, which would have an RF pulsed frequency of 128 MHz, there are certain exact implanted lead lengths that would couple efficiently as fractions of the 128 MHz wavelength. Ignoring the effects of body tissue, as an example, the basic wavelength equation (in air) in meters is 300 divided by the frequency in MHz. Accordingly, for a 3.0 Tesla MRI system, the wavelength is 2.34 meters or 234 centimeters. An exact ¼ wavelength antenna then would be ¼ of this which is 58.59 centimeters. Both ¼ wave and ½ wave antennas are very efficient energy couplers. When the shorter wavelengths in body tissue are accounted for, this falls right into the range for the length of certain pacemaker lead wire implants.

It is typical that a hospital will maintain an inventory of various leads and that the implanting physician will make a selection depending on the size of the patient, implant location and other factors. Accordingly, the implanted or effective lead wire length can vary considerably.

Another variable has to do with excess lead wire. It is typical that the physician, after doing a pacemaker lead wire insertion, will wrap up any excess lead wire in the pectoral pocket. This can form one, two or even three turns of excess lead. This forms a loop in that specific area, however, the resulting longer length of wire that goes down into the right ventricle, is what would then couple efficiently with the MRI RF pulsed frequency. As one can see, the amount of unwound up lead length is considerably variable depending upon patient geometry.

There are certain implanted lead wire lengths that just do not couple efficiently with the MRI frequency and there are others that would couple very efficiently and thereby produce the worst case for heating. The actual situation for an implanted lead wire is far more complex due to the varying permittivity and dielectric properties of body tissues, and the accompanying shifts in wavelengths.

The effect of an MRI system on the function of pacemakers, ICDs, neurostimulators and other AMDs depends on various factors, including the strength of the static magnetic field, the pulse sequence (gradient and RF field used), the anatomic region being imaged, and many other factors. Further complicating this is the fact that each manufacturer's pacemaker and ICD designs behave differently. Most experts still conclude that MRI for the pacemaker patient should not be considered safe. Paradoxically, this also does not mean that the patient should not receive MRI. The physician must make an evaluation given the pacemaker patient's condition and weigh the potential risks of MRI against the benefits of this powerful diagnostic tool. As MRI technology progresses, including higher field gradient changes over time applied to thinner tissue slices at more rapid imagery, the situation will continue to evolve and become more complex. An example of this paradox is a pacemaker patient who is suspected to have a cancer of the lung. RF ablation treatment of such a tumor may require stereotactic imaging only made possible through real time fine focus MRI. With the patient's life literally at risk, and with informed patient consent, the physician may make the decision to perform MRI in spite of all of the previously described attendant risks to the pacemaker system.

Insulin drug pump systems do not seem to be of a major current concern due to the fact that they have no significant antenna components (such as implanted lead wires). However, implantable pumps presently work on magneto-peristaltic systems, and must be deactivated prior to MRI. There are newer (unreleased) systems that would be based on solenoid systems which will have similar problems.

It is clear that MRI will continue to be used in patients with an active implantable medical device. There are a number of other hospital procedures, including electrocautery surgery, lithotripsy, etc., to which a pacemaker patient may also be exposed. Accordingly, there is a need for circuit protection devices which will improve the immunity of active implantable medical device systems to diagnostic procedures such as MRI.

As one can see, many of the undesirable effects in an implanted lead wire system from MRI and other medical diagnostic procedures are related to undesirable induced currents in the lead wire system. This can lead to overheating either in the lead wire or at the tissue interface at the distal TIP. At the 2006 SMIT Conference, the United States Food and Drug Administration (FDA) reported on a neurostimulator patient whose implanted leads were sufficiently heated that severe burns occurred resulting in the need for multiple amputations. In pacemaker patients, these currents can also directly stimulate the heart into sometimes dangerous arrhythmias. The above descriptions of problems that a pacemaker, ICD or neurostimulator patient may encounter during MRI or similar medical diagnostic procedures are only examples of a general need. A patient wearing external devices, such as an external drug pump, an external neurostimulator, EKG leads, (skin patches) or ventricular assist devices, may also encounter problems during an MRI procedure. All of the above descriptions regarding overheating of lead wires, overheating of distal tips or electromagnetic interference are of concern. The novel electronic switch of the present invention is applicable to all of these other devices. It is also applicable to probes and catheters that are used during certain real time medical imaging procedures such as MRI. The present invention is applicable to a wide range of both implanted and external medical device systems.

Accordingly, there is a need for a circuit protection device that protects a patient undergoing high RF power medical diagnostic procedures, such as an electronic switch placed either at the device, in the lead wire system or at or near the distal tip electrodes. Various methodologies are also needed wherein the electronic switch can be preferentially opened and closed either by a medical doctor or the radiologist just prior to medical procedures such as magnetic resonance imaging. The present invention fulfills these needs and provides other related advantages.

SUMMARY OF THE INVENTION

The present invention comprises novel electronic switches to be placed at the distal tip and/or various locations along the medical device, lead wires or circuits. These switches prevent current from circulating that could be induced by a medical therapeutic diagnostic device.

For example, for an MRI system operating at 1.5 Tesla, the pulsed RF frequency is 64 MHz, as described by the Lamour Equation. The novel electronic switches of the present invention, when placed at the distal tip of a pacemaker lead wire, will stop RF currents from flowing through the distal tip (or ring electrode) and then into body tissue. The electronic switch of the present invention stops RF currents from flowing across the entire frequency spectrum. This means that the RF fields and gradient fields that could be induced from MRI imaging equipment cannot flow, for example, into myocardial or other human tissues. This stops the problems associated with overheating of lead wires, tissue damage and excessive currents or temperatures, and also the potential for gradient field capture of the heart which can lead to dangerous arrhythmias.

The novel electronic switch can also reduce EMI or RF currents or electromagnetic interference from flowing in the lead wire system into the input of an active implantable medical device (AIMD) such as a pacemaker. This provides added protection to sensitive electronic circuits of the AIMD. It will be obvious to those skilled in the art that all of the embodiments described herein are equally applicable to a wide range of other implantable and external medical devices, including deep brain stimulators, spinal cord stimulators, drug pumps, probes, catheters and the like.

Thus, in accordance with the present invention, an MRI-compatible electronic medical therapy system comprises an active medical device (AMD), having an electronic circuit and a power supply. A plurality of electrodes are electrically connected to the electronic circuit of the AMD and adapted for insertion into or connection with biological tissue. A multiplexer circuit, including at least one, but fewer than a plurality of electrodes, circuit protection devices are in electrical series with the plurality of electrodes and the AMD electronic circuit. The at least one circuit protection device is adapted to permit current flow therethrough during normal AMD-related therapy, but substantially prevent current flow therethrough in the presence of an induced electromagnetic field.

The medical device (AMD) may comprise a cochlear implant, a piezoelectric sound bridge transducer, a neurostimulator, a brain stimulator, a cardiac pacemaker, a ventricular assist device, an artificial heart, a drug pump, a bond growth stimulator, a bone growth stimulator, a bone fusion stimulator, a urinary incontinence device, a pain relief spinal cord stimulator, an anti-tremor stimulator, a gastric stimulator, an implantable cardioverter defibrillator, a pH probe, a congestive heart failure device, a pill camera, a neuromodulator, a cardiovascular stent, an orthopedic implant, an external insulin pump, an external drug pump, an external neurostimulator, a Holter monitor, an external probe, or a catheter.

The induced electromagnetic field comprises a radio frequency, magnetic or static field. The switch comprises a normally closed switching element creating a closed circuit between the electrode and the AMD, and which is automatically moved to an open position to create an open circuit in the presence of the induced radio frequency, electrostatic or magnetic field. The switching element automatically closes on removal of the induced radio frequency, electrostatic or magnetic field.

In a preferred form of the invention, an MRI-compatible electronic medical therapy system is provided which comprises (1) an active medical device (AMD) having an electronic circuit and a power supply; (2) a plurality of electrodes electrically connected to the electronic circuit of the AMD and adapted for insertion into or into contact with biological tissue; and (3) a multiplexer circuit including at least one, but fewer than the plurality of electrodes, circuit protection device in electrical series with the plurality of electrodes and the AMD electronic circuit, the at least one circuit protection device being adapted to permit current flow therethrough during normal AMD-related therapy, but substantially prevent current flow therethrough in the presence of an induced electromagnetic field. A circuit protection device comprises a bandstop filter including a capacitor in parallel with a resistor, wherein the levels of capacitance and resistance are selected for a predetermined frequency range of the electromagnetic field.

The electromagnetic field may comprise a radio frequency, magnetic or static field, or an MRI field. The bandstop filter is closed during normal AMD-related therapy, but opens in the presence of the electromagnetic field. The bandstop filter has a Q so as to resonate with a 3 dB bandwidth over a range of MRI frequencies in the megahertz range. The multiplexer circuit comprises a switch assembly having multiple switches or switch relays.

In another form, the present invention comprises an MRI-compatible implantable electronic medical therapy system, comprising: (1) an active medical device (AMD) having an electronic circuit and a power supply disposed within a housing, and a lead extending exteriorly of the housing; (2) a plurality of electrodes electrically connected to the electronic circuit of the AMD and adapted for insertion into or into contact with biological tissue; and (3) a multiplexer circuit disposed within the lead and including at least one, but fewer than the plurality of electrodes, bandstop filter switch in electrical series with the plurality of electrodes and the AMD electronic circuit. The at least one switch is normally closed to permit flow therethrough during normal AMD-related therapy, but opens to prevent current flow therethrough in the presence of an induced radio frequency, magnetic or static electromagnetic field.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 2 is a perspective and somewhat schematic view of a prior art active implantable medical device (AIMD) including a lead wire directed to the heart of a patient;

FIG. 3 is a diagram of a unipolar active implantable medical device (AIMD);

FIG. 4 is a diagram similar to FIG. 3, illustrating a bipolar AIMD system;

FIG. 5 is a diagram similar to FIGS. 3 and 4, illustrating a bipolar lead wire system with a distal TIP and RING electrode, typically used in a cardiac pacemaker;

FIG. 19 is a sectional view which is very similar to FIG. 18, illustrating an alternative embodiment for an electronic switch which can be optionally associated with radio frequency (RFID) activation;

FIG. 20 is a schematic diagram of the hermetically sealed electronic switch of FIG. 19;

FIG. 32 is a table showing the relationship between the medical French gauge converted to diameter in millimeters and inches;

DETAILED DESCRIPTION OF THE PREFERRED EMBODIMENTS

Figure 1:
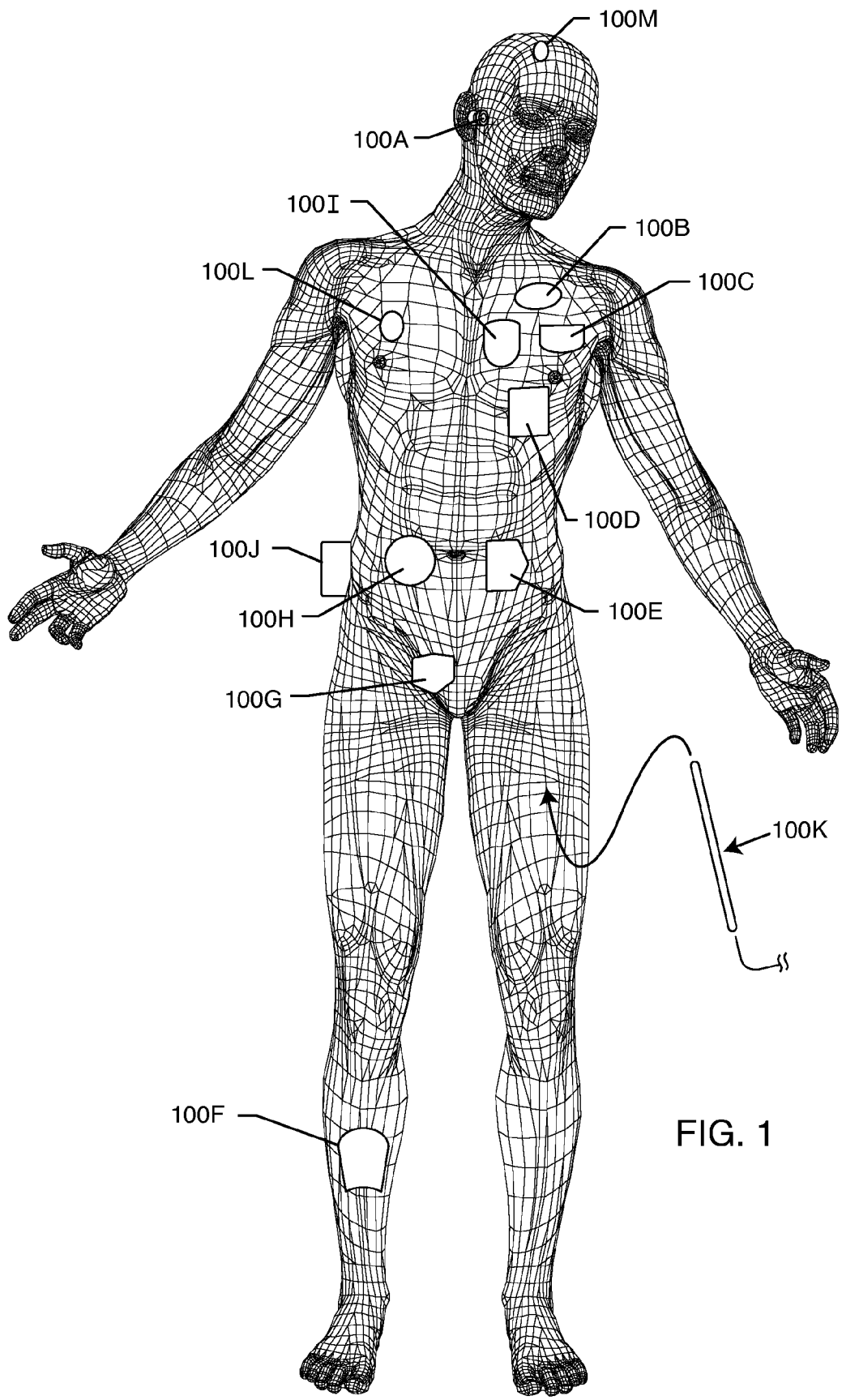
FIG. 1 is a wire-form diagram of a generic human body showing a number of active medical devices (AMD) and associated internal and external lead wires.

As shown in the drawings for purposes of illustration, the present invention resides in the placement of electronically activated switches in series with lead wires or circuits of active medical devices to protect the patient and/or medical device from undesirable electromagnetic interference signals, such as those generated during MRI and other medical procedures. The present invention also resides in the design, manufacturing, and installation of such electronic switches to be used in the lead wires, inside the active implantable medical device itself or at or in conjunction with a distal tip electrode of AIMDs. As will be explained more fully herein, the invention is applicable to a wide range of external medical devices, probes, catheters, monitoring lead wires and the like that may be temporarily inserted onto a patient or that a patient may be wearing or connected to during medical diagnostic procedures, such as MRI.

Another need which resides primarily within the neuromodulation community is the need to perform real time MRI guided placement of deep brain stimulator electrodes, spinal cord stimulator electrodes and the like. Currently, because of the fear of overheating such electrodes, surgical guidance of these electrodes is quite difficult. What typically happens is the patient is exposed to various MRI scans that are correlated with marks that are placed on the patient's skull. There is a stereotactic mechanical device that is then either affixed or literally screwed to the patient's skull which guides the surgical fixture. There is really no imaging done during this type of surgical procedure. Everything relies upon the mechanical alignment of the aforementioned tools. At the recent Neuromodulation Society Conference held in December of 2007 in Acapulco, Mexico a number of neurosurgeons mentioned the need for real time MRI guidance of such electrodes. The present invention makes this very feasible. With a novel electronic switch of the present invention in the open position, real time MRI imaging can be conducted without any fear of overheating the electrodes. Then, after the electrode is accurately guided and placed in the correct location in the brain or spinal cord tissue, the electronic switch can be closed so that the surgeon can perform various tests of the patient to select the appropriate electrode pairs. Advantages of real time MR guided placement of electrodes include more accurate placement, less discomfort to the patient by the elimination of the stereotactic mechanical means for placement and the ability to reach small and delicate physiologic areas that were previously too difficult.

Another application is in ablation catheters and ablation probes. For example, an ablation catheter could be placed up through the venous system and into one of the atria of the heart. Currently such ablation procedures, for example to try to eliminate atrial fibrillation, are done blind and require a great deal of skill by the physician. It would be extremely desirable to have this procedure real time MRI guided. In the present invention the electronic switch could be open during the MRI guidance and then closed at the moment the ablation pulse is applied. In fact, the ablation pulse itself could create sufficient electrostatic forces to close a MEMS switch and thereby, at the same time, close the circuit and deliver the therapy to the appropriate location.

Yet another need resides in common surgical procedures. Electrocautery is a very common surgical technique. The surgeon often works with an instrument such as the Bovi knife that cauterizes blood vessels as it cuts. However, the intense RF energy from such electrocautery equipment can damage the sensitive electronic circuitry of AIMDs. It is a particular advantage of the present invention to incorporate electronic switches such that the AIMD is disconnected during such procedures so that the AIMD is well protected.

In an illustrated embodiment, the electronic switch is a Micro-Electromechanical System (MEMS) type of electrostatic switch device. The electronic switch would be preferentially opened just prior to the patient receiving a therapeutic or diagnostic medical procedure which has the potential to induce high currents or other undesirable electromagnetic interference into the AIMD system. A downside of opening the switch is that the therapy electrode(s) will be disconnected. In other words, during the medical therapy or diagnostic procedure, it will not be possible for the patient to receive therapy from the AIMD. In general, this is not a problem for most deep brain stimulator (DBS), spinal cord stimulator (SCS), cochlear implant patients, urinary incontinence, diabetics, people suffering from depression, people suffering from Parkinson's tremor and the like. In other words, it is not a disadvantage for these types of patients to be without therapy for the relatively short time of the medical diagnostic imaging or therapeutic procedure. There is a concern for patients who depend on each electrical pace of the implanted pacemaker so that their heart will function properly. For a pacemaker dependent patient, lack of a pacing pulse is, of course, life threatening. However, there is still a way around this and to still provide for safe medical diagnostic imagine procedures. For this type of patient, it will be necessary to place MRI compatible skin electrodes in conjunction with an external pacemaker during the time that the medical procedure is performed. In this case, the electronic switch in the patient's lead wire systems would be open thereby making therapy from the AIMD not possible. However, by properly externally pacing, one can get around this without any threat to the patient. A novel electronic switch structure as described herein also has a broad application to other medical procedures and even procedures involving telecommunications, military, space and the like.

In the present invention, the microelectronic switch and/or MEMS switches ideally are of a type that do not require power other than during the actual switching event. This is why a MEMS switch is ideal. There are other types of RF switches that are also mechanically functioning switches. These are electrically controlled two-state switches that open and close contacts to effect operation in the electrical system. When the switch is open, this prevents therapeutic and sensing signals from passing, but also prevents unwanted induced RF signals from passing which can cause overheating or undesirable tissue effect. The present invention includes many mechanical and solid state types of switching. The preferred embodiment includes a MEMS switch which, in general, includes micro-electrostatic and micro-magnetic relays (open and closed switches). MEMS switches are termed electrostatic MEMS switches if they are actuated or controlled during electrostatic force which turns such switches on and off. Electrostatic MEMS switches are advantageous due to their extremely low power consumption because they can be actuated using electrostatic force induced by the application of a voltage with virtually no current. Some switches that are well known in the art are used in a number of applications include variable RF phase switches, RF switching signal arrays, switching tunable elements as well as gang switching of voltage control oscillators. MEMS switches are important building blocks in many wireless communications systems. RF switches, including MEMS switches, are found in many different communication devices such as cellular telephones, wireless pagers, wireless infrastructure equipment, satellite communications equipment, and cable vision equipment. The most basic type of electronic switch, including certain MEMS switches, is a single pole single throw (SPST), which contains a single input and a single output. Other switches are available which come in single pole multiple throw (SPMT) configurations. The typical switch in accordance with the present invention will contain two parts including an input and an output which are controlled together (or may be separately controlled). In one embodiment, the switch of the present invention is located at the distal electrode and integrated within. As an alternative, it may be placed close to the electrode. Alternatively, the electronic switches could be placed anywhere in the AIMD lead wire system or within the AIMD itself. Because of the way the RF field couples from, for example, an MRI system, it is often advantageous to have the switch as near the distal tip electrode(s) as possible. This is because EMFs from the pulsed RF field of an MRI machine tend to be distributed along the entire length of the lead system. These EMFs are separated by the transmission line impedances of the lead wire system. In lay terms, one can place such a switch within the AIMD itself but still have substantial RF currents, overheating of distal tip electrodes and tissue damage still occur. This is because the distal tip is electrically isolated from the AIMD itself at high frequencies. Alternative electronic switches could consist of a number of solid state devices such as diodes and field effect transistors (FETs). These types of devices are typically fabricated using Gallium Arsenide (GaAs) technology. Solid state RF switches are generally made using GaAs processes. All of these would be acceptable in the present application, but not necessarily ideal. The problem with GaAs devices are that they do require a certain amount of power to operate. An advantage of the MEMS technology is that other than during the actual switching, they require no power at all from the system. This is extremely important in an AIMD where power consumption is of utmost concern. PIN diodes are semiconductor devices which can also be used in switching applications. They have a high or very low resistance value depending on the value of the biasing characteristics. PIN diodes are typically fabricated in Si and GaAs technologies. One of the more serious drawbacks of these switches is the necessity to provide a constant DC current. This becomes impractical at the distal tip electrodes of an AIMD because more lead wires would generally be required. Again, this is why MEMS technology is an advantage. In addition, using discrete PIN diodes would increase both the size and the cost of the distal tip electrode assembly. This is also why transistor type junctions are generally not the preferred embodiment, but can definitely be used in switching applications.

As stated, MEMS technology is the preferred embodiment for fabrication of the electronic switches of the present invention. These are miniature devices that can be manufactured in a wide variety of mechanical forms. MEMS devices are inherently both mechanical and electrical devices that are subject to wear and contamination and can suffer from limited lifetimes. However, in accordance with the present invention, this is not particularly important. Patients will only undergo typically a few therapeutic or diagnostic procedures in their lifetime. They will certainly not undergo millions of such procedures which starts to approach the lifetime of a typical MEMS device. A MEMS system is typically fabricated using a semiconductor integrated circuit type of fabrication technology. MEMS switches tend to be ultra-small type devices. MEMS switches in the present application are ideal in that they have a very high off impedance with a very low off capacitance and a relatively low on impedance with a high on capacitance. These are important advantages for use in the lead wire system in an active implantable medical device. When the MEMS switch is on, it is very important that the impedance be low so that there is no degradation of biological sensing signals or therapeutic signals such as a pacemaker pacing pulse. A resistive type MEMS switch is preferred. In a capacitive type MEMS switch, a dielectric layer is deposited on the first conductor in an area opposite to the underside of the two-movable bridge, with this area on the conductor acting as the pull down electrode. With this arrangement, the full pull down voltage appears across the dielectric area resulting in a relatively high electric field across the dielectric. The problem with this, for active implantable medical devices, is that a relatively high impedance would occur across this capacitive layer at low frequencies. Because of this, in the present invention, a resistive type MEMS switch is preferred.

MEMS switches can be activated through the application of a static field or when they include ferrite materials by the activation of a magnetic field. The present invention includes MEMS switches that would automatically activate in the presence of the very powerful fixed magnetic field ($B_0$) of an MRI scanning system.

Another advantage of MEMS switches is that they are very cost effective and can be built in very small geometries. This makes them ideal for packaging within a hermetic distal tip.

In the present invention, it is preferable that the MEMS switch or equivalent electronic switch be designed such that it does not require additional lead wires in the implanted AIMD lead wire system. That is, the MEMS switch will be placed in series with the electrode delivery lead wire(s). It is therefore important that the MEMS switch not be inadvertently activated by the application of therapy (for example, pacemaker pacing pulses). For example, for an electrostatic type MEMS switch, it will be important that a voltage be applied in the AIMD lead wire systems sufficient to create an electrostatic field to activate the MEMS switch and cause it to switch from its normally closed to its open position. The voltage that is applied is typically at a higher voltage than those of normal therapeutic pacing pulses. However, this voltage should be at a level below which will it have a deleterious effect on body tissues. Accordingly, it is a feature of the present invention that the voltages and/or pulses required to activate the electronic switch be desirably below a therapeutic or tissue stimulation threshold voltage. What is more important is that the switch activation voltages and currents be below a threshold which would cause dangerous tissue stimulation or damage. Fortunately, there is a considerable window between the relatively low therapeutic neuromodulation thresholds and the threshold where actual tissue damage would occur.

As mentioned, the preferred embodiment is a MEMS switch which is electrostatically activated. This approach is ultra low power because typically only a nano-joule of power is required for each switching event and no power is consumed when the switch is either in the closed or open state. This approach is far better suited to power sensitive applications such as those for AIMDs than the more power hungry magnetic switch activation approach that is traditionally used in mechanical relays. This is also superior to other electronic switches such as diodes or FETs which also require a constant supply of energy. The switching alternative products that are most similar to MEMS switches and who have very high reliability, are high density interconnect (HDI) switches and conventional electro-mechanical relays. As previously mentioned, negatives to these approaches are that they are relatively large in size and they also consume energy. When properly designed, MEMS switches operate with much lower forces and much lower power consumption with much longer lifetimes. Off-the-shelf electronic switches or MEMS switches are ideal for a variety of low voltage neurostimulator, pacemaker and cochlear implant applications. However, there are certain high voltage and high power applications such as implantable cardioverter defibrillator (ICD) applications which require a special type of electronic switch. Fortunately, high power RF MEMS switches can be designed and fabricated. In general, these switches are composed of a matrix of ohmic contact cantilevers and bridges. The fabrication processes have been developed to improve planarization on the MEMS switch contact surfaces and thereby reduce residual stresses in switch beams, which ensure that a very flat and smooth surface results. This is important so that the MEMS switch can operate at high power and low activation voltage.

The two major suppliers in the MEMS switch market are Microlab and Teravicta, although there are other suppliers. An ideal switch for the present invention is Teravicta's TT612 switch which is a MEMS device with a micromachined cantilever that rapidly bends like a diving board from an on to an off position in response to an electrostatic signal. The present invention includes existing RF switches which are really solid-state semiconductor devices that turn on and off electronically. However, as previously explained, the MEMS type of switch has performance advantages and power consumption advantages over the solid-state type devices. There are other types of MEMS switches other than the ones that use electrostatic actuation. The most common one is one that uses a magnetic latching and switching mechanism that eliminates the need for the static power supply and that can latch on or off with zero power required to hold this state. The switch is nonvolatile and bi-stable. Because of the long range magnetic forces, the switch requires very low operation voltage. Such a switch, in accordance with the present invention, is designed to be automatically activated when placed in the presence of the powerful static magnetic field of a magnetic resonance imaging system. Such a switch can operate at 0.5 Tesla, 1.5 Tesla, 3 Tesla and the like. Multiple magnetically activated MEMS devices can be placed in various x, y and z geometries so that it does not matter what their orientation is within the bore of the MRI system. In other words, by using multiple MEMS devices, it will always be assured that at least one or more of them switches.

The principle behind the latching characteristics is the preferential magnetization of a cantilever made of soft magnetic material (for example, permalloy). In a nearly perpendicular magnetic field, a cantilever can have a clockwise or counter clockwise torque depending on the angle between the cantilever in the magnetic field, which leads to the bi-stability. To switch the relay, a second magnetic field, in this case generated by a short current pulse through a coil, realigns the magnetization of the cantilever causing it to flip. A static external magnetic field, such as that from an MRI scanner, instantly latches the switch in the closed or open position (whichever is desired), respectively. The switch maintains this state until the next switching signal realigns the cantilever. The relay consumes no power to maintain the latched state. Accordingly, with such a magnetically activated MEMS switch, the physician or the radiology technician can apply an external magnet or coil over the AIMD electrode to switch the switch back into the desired therapy delivery state. Whereas previously noted, this can be done automatically by placement of the patient into the powerful static field of the MRI scanner. Once the scanning sequence is completed and the patient is removed, then it is a relatively easy matter to apply an opposite torque using a simple device consisting of a coil which will apply the opposite magnetic effect.

There are also electronic switches in a particular MEMS technology that will suppress high voltage arc phenomena. Arc suppressors can be put across the MEMS switch, for example, to make them more resistant to external defibrillation. In addition, this will make them more robust and able to withstand undesirable electrostatic discharge (ESD). Accordingly, it is a feature of the present invention that any of the electronic, electromechanical or MEMS switches that can be used in the present invention could also be combined with various forms of arc suppression (including zener diode, Transorb technology, and the like) in order to protect them. The types of switches that can be used in accordance with the present invention include micromachined electromagnetic switches such as those described in U.S. Pat. No. 5,475,353; micro electromechanical RF switches as defined in U.S. Pat. No. 5,578,976; micro electromechanical switches as described in U.S. Pat. No. 6,160,230; and MEMS switches as described in U.S. Pat. No. 6,218,911. There are also a number of other switches that can be used that are cited in the referenced patents on the first page of this application. In general, in the present invention, a method of performing electrical switching in the lead wire or distal tip electrode of the AIMD is included such that it would be disconnected from body tissue in the presence of powerful emitters such as those used in medical diagnostic, therapy or imaging equipment. In the preferred embodiment, the method of performing electrical switching resides in a MEMS type device where either a static, magnetic field, or RF field (RFID) is used to change the switch state. Other than during switching, such devices require little to no power.

In another embodiment, the MEMS type switch or other electronic switch can be activated from the field, for example, of an MRI machine, through an antenna. This is very similar to the type of antennas used in the RFID industry. Passive RFID tags require no battery or no power source. They obtain all of their power to activate their microcircuit from the external electromagnetic field. For an RFID device, the external magnetic field is provided by the RFID reader. In the present application, this can certainly be done, however, for an MRI device, the external electromagnetic field can be provided by the MRI machine itself. In a preferred embodiment for a MEMS type switch, the preferred movable metallic conductor, inclusive electrical switching element would be of a cantilever type configuration. Maintaining an electromechanical type switch or MEMS switch in the open position can be accomplished through the action of a spring tension resident in the movable arm portion. Such normally closed type switches are known in the prior art (see U.S. Pat. No. 6,373,007).

FIG. 1 illustrates various types of active implantable and external medical devices 100 that are currently in use. FIG. 1 is a wire formed diagram of a generic human body showing a number of implanted medical devices. 100A represents a family of hearing devices which can include the group of cochlear implants, piezoelectric sound bridge transducers and the like. 100B represents a variety of neurostimulators, neuromodulators and brain stimulators. Neurostimulators are used to stimulate the Vagus nerve, for example, to treat epilepsy, obesity and depression. Brain stimulators are pacemaker-like devices and include electrodes implanted deep into the brain for sensing the onset of the seizure and also providing electrical stimulation to brain tissue to prevent the seizure from actually occurring. As noted above, it would be a significant improvement in surgical technique if the lead wires associated with a deep brain stimulator could be placed using real time MRI imaging. 100C shows a cardiac pacemaker which is well-known in the art. 100D includes the family of left ventricular assist devices (LVAD's), and artificial hearts, including the recently introduced artificial heart known as the Abiocor. 100E includes an entire family of drug pumps which can be used for dispensing of insulin, chemotherapy drugs, pain medications and the like. Insulin pumps are evolving from passive devices to ones that have sensors and closed loop systems. That is, real time monitoring of blood sugar levels will occur. These devices tend to be more sensitive to EMI than passive pumps that have no sense circuitry or externally implanted lead wires. 100F includes a variety of bone growth stimulators for rapid healing of fractures. 100G includes urinary incontinence devices. 100H includes the family of pain relief spinal cord stimulators and anti-tremor stimulators. 100H also includes an entire family of other types of neurostimulators used to block pain. 100L includes a family of implantable cardioverter defibrillators (ICD) devices and also includes the family of congestive heart failure devices (CHF). This is also known in the art as cardio resynchronization therapy devices, otherwise known as CRT devices. 100J illustrates an externally worn pack. This pack could be an external insulin pump, an external drug pump, an external neurostimulator or even a ventricular assist device. 100K illustrates the insertion of an external probe or catheter. These probes can be inserted into the femoral artery, for example, or in any other number of locations in the human body. 100L illustrates one of various types of EKG/ECG external skin electrodes which can be placed at various locations. 100M are external EEG electrodes placed on the head.

FIG. 2 illustrates a prior art active implantable medical device (AIMD) 100. In general, the AIMD 100 could, for example, be a cardiac pacemaker 100C which is enclosed by a titanium housing 102 as indicated. The titanium housing is hermetically sealed, however, there is a point where lead wires 104 must ingress and egress the hermetic seal. This is accomplished by providing a hermetic terminal assembly 106. Hermetic terminal assemblies are well known and generally consist of a ferrule 108 which is laser welded to the titanium housing 102 of the AIMD 100. Referring once again to FIG. 2, four lead wires are shown consisting of lead wire pair 104a and 104b and lead wire pair 104c and 104d. This is typical of what's known as a dual chamber bipolar cardiac pacemaker.

The IS1 connectors 110 that are designed to plug into the header block 112, such as in ports 118, are low voltage (pacemaker) connectors covered by an ANSI/AAMI standard IS-1. Higher voltage devices, such as implantable cardioverter defibrillators (ICDs), are covered by a standard known as the ANSI/AAMI DF-1. There is a new standard under development which will integrate both high voltage and low voltage connectors into a new miniature connector series known as the IS-4 series. These connectors are typically routed in a pacemaker application down into the right ventricle and right atrium of the heart 114. There are also new generation devices that have been introduced to the market that couple lead wires to the outside of the left ventricle. These are known as biventricular devices and are very effective in cardiac resynchronization and treating congestive heart failure (CHF).

Referring once again to FIG. 2, the bipolar lead wires 104a and 104b could be routed, for example, into the right ventricle. The bipolar lead wires 104c and 104d could be routed to the right atrium. There is also an RF telemetry pin antenna 116 which is not connected to the IS-1 or DS-1 connector block. This acts as a short stub antenna for picking up telemetry (programming) signals that are transmitted from the outside of the device 100.

It should also be obvious to those skilled in the art that all of the descriptions herein are equally applicable to other types of AIMDs. These include implantable cardioverter defibrillators (using the aforementioned DF-1 connectors), neurostimulators (including deep brain stimulators, spinal cord stimulators, cochlear implants, incontinence stimulators and the like), and drug pumps. The present invention is also applicable to a wide variety of minimally invasive AIMDs. For example, in certain hospital catheter lab procedures, one can insert an AIMD for temporary use such as an ICD. Ventricular assist devices also can fall into this type of category. This list is not meant to be limiting, but is only an example of the applications of the novel technology currently described herein.

FIG. 3 is a general diagram of a unipolar active implantable medical device system 100. The housing 102 of the active implantable medical device 100 is typically titanium, stainless steel or the like, and acts as one conductive electrode. Inside of the device housing are the AIMD electronics. Usually AIMDs include a battery, but that is not always the case. For example, a Bion may receive its energy from an external pulsing magnetic field. A lead wire 104 is routed in insulative relationship with the AIMD housing to a point 120 where it is embedded in body tissue. In the case of a spinal cord stimulator 100H, the distal TIP 120 could be in the spinal cord. In the case of a deep brain stimulator 100B, the distal electrode 120 would be placed deep into the brain tissue, etc. In the case of a cardiac pacemaker 100C, the unipolar distal electrode 120 would typically be placed in the cardiac right ventricle.

FIG. 4 is very similar to FIG. 3 except that it is a bipolar system. In this case, the return path is between the two distal electrodes 120a and 120b. In the case of a cardiac pacemaker 100C, this would be known as a bipolar lead wire system with one of the electrodes known as the distal TIP 120a and the other electrode which would float in the blood pool known as the RING 120b (see FIG. 5). In contrast, the return path in FIG. 3 is between the distal electrode 120 through body tissue to the conductive housing 102 of the implantable medical device 100.

FIG. 5 further illustrates a bipolar lead wire system with a distal TIP 120a and RING 120b typically as used in a cardiac pacemaker 100C. In all of these applications, the patient could be exposed to the fields of an MRI scanner or other powerful emitter used during a medical diagnostic procedure. RF currents that are directly induced in the lead wire system 104 can cause heating by Ohmic ($I^2R$) losses in the lead wire system or by heating caused by current flowing in body tissue. If these currents become excessive, the associated heating can cause damage or even destructive ablation to body tissue.

The distal TIP 120a is designed to be implanted adjacent to or affixed into the actual myocardial tissue of the heart. The RING 120*b* is designed to float in the blood pool. In a pacemaker cardiac chamber, the blood is flowing (i.e. perfusion) and is thermally conductive, therefore RING 120*b* structure is substantially cooled. However, the distal TIP 120*a* is thermally insulated by surrounding body tissue and can readily heat up due to the RF pulsed currents of an MRI field.

Accordingly, for a cardiac pacemaker application, the novel electronic switch concepts of the present invention will be more directed to the distal TIP 120*a* as opposed to the RING 120*b* electrode (although the concepts of the present invention can be applied to both). For poorly perfused areas, such as is typical in neurostimulator electrodes, then both TIP and RING electrodes must have an electronic switch circuit of the present invention.

Figure 6:
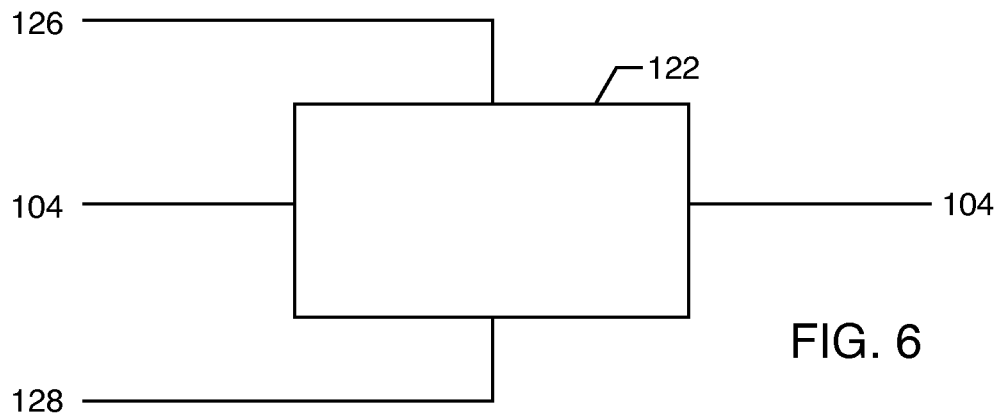
FIG. 6 is a line drawing showing an electronically controlled switch module in series with a unipolar lead wire system.
Figure 7:
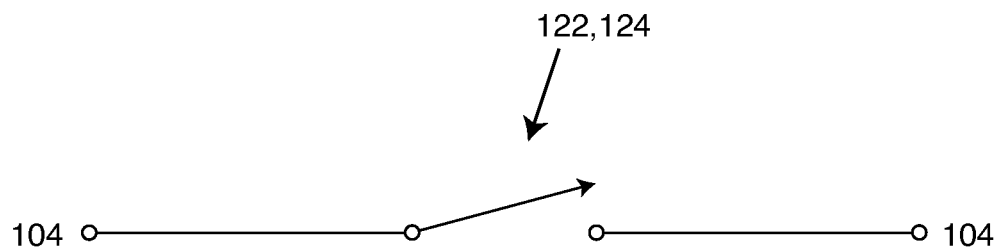
FIG. 7 is the schematic of the electronically controlled switch of FIG. 6.

FIG. 6 shows an electronic filter module 122 shown in series with the lead wire 104 of any of the unipolar or bipolar AIMD systems as previously illustrated in FIGS. 3, 4 and 5. One can see that there are control leads 126 and 128 where power can be supplied to the electronic switch module 122. Also, by varying the power or adding electronic pulses, the switch module 122 can be opened and closed. FIG. 7 gives a schematic diagram of the equivalent circuit of the switch 122.

Figure 8:
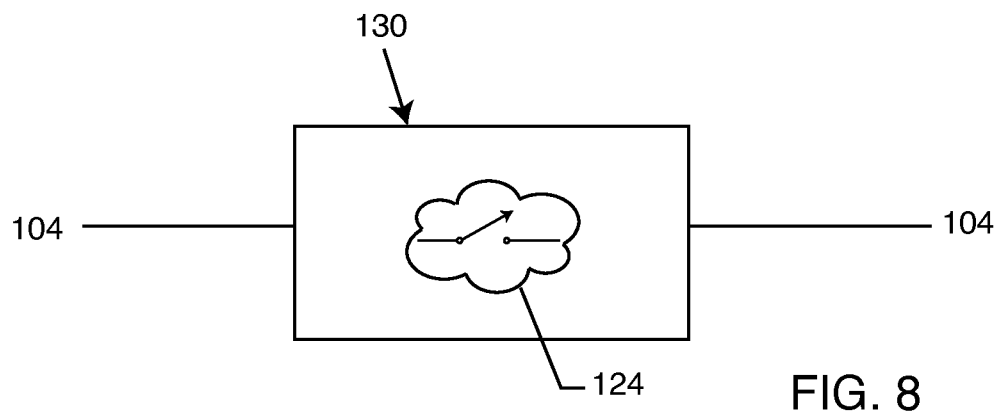
FIG. 8 is similar to FIG. 6 except that the switch module has been replaced by a micro-electromechanical system (MEMS) technology switch.

FIG. 8 is an improved switch module 130 which incorporates a MEMS technology switch 124 in accordance with the present invention. In this case, the power and control lead wires 126 and 128 are no longer needed. Again, FIG. 7 is the equivalent circuit model for the MEMS switch of FIG. 8.

Figure 9:
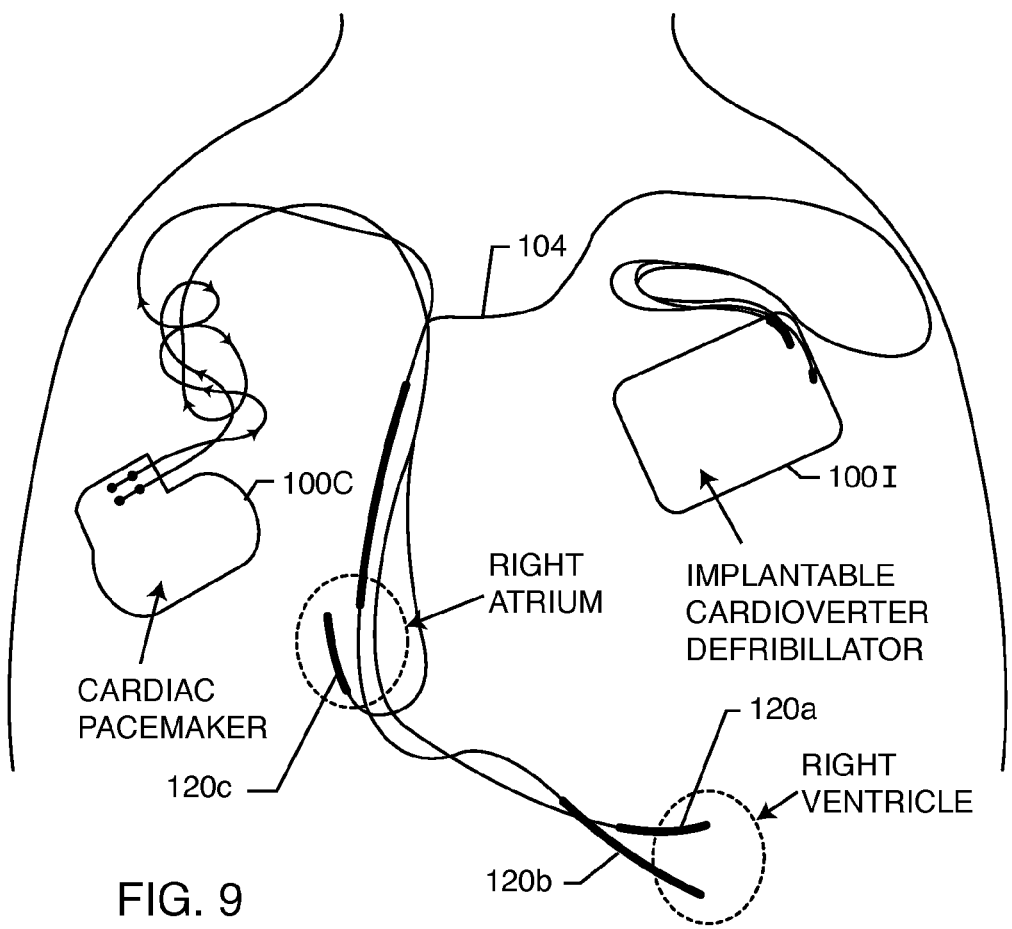
FIG. 9 is a tracing of an exemplary patient X-ray showing an implanted cardiac pacemaker and cardioverter defibrillator and corresponding lead wire system.

FIG. 9 is a tracing of an actual patient X-ray from the Association for the Advancement of Medical Instrumentation (AAMI) PC69 Pacemaker EMC Task Force. This particular patient required both a cardiac pacemaker 100C and an implantable cardioverter defibrillator 100I. The corresponding lead wire system 104, as one can see, makes for a very complicated antenna and loop coupling situation. The reader is referred to the article entitled, "Estimation of Effective Lead Loop Area for Implantable Pulse Generator and Implantable Cardioverter Defibrillators" provided by the AAMI Pacemaker EMC Task Force.

Referring again to FIG. 9, one can see that from the pacemaker 100C, there are electrodes 120*a-c* in both the right atrium and in the right ventricle. Both these involve a TIP and RING electrode. In the industry, this is known as a dual chamber bipolar lead wire system. Accordingly, at a minimum the electronic switches 124 of the present invention should be placed at the distal TIP 120*c* in the right atrium and the distal TIP 120*a* in the right ventricle from the cardiac pacemaker. The implantable cardioverter defibrillator (ICD) 100I is typically implanted directly into the right ventricle. Its shocking TIP and sense electrodes 120 would incorporate an electronic switch 124 either into the electrode 120 or preferably placed adjacent to the electrode 120 and in series with the lead wire 104 so that MRI exposure cannot induce excessive currents in that lead wire system. Modern implantable cardioverter defibrillators (ICDs) incorporate both pacing and cardioverting (shock) features. Accordingly, it is becoming quite rare for a patient to have two discrete AIMD systems, as shown in FIG. 9. However, the number of electrodes remains the same. There are also newer combined pacemaker/ICD systems which include biventricular pacemakers (pacing of the left ventricle). These systems can have as many as nine to even twelve lead wires.

Figure 10:
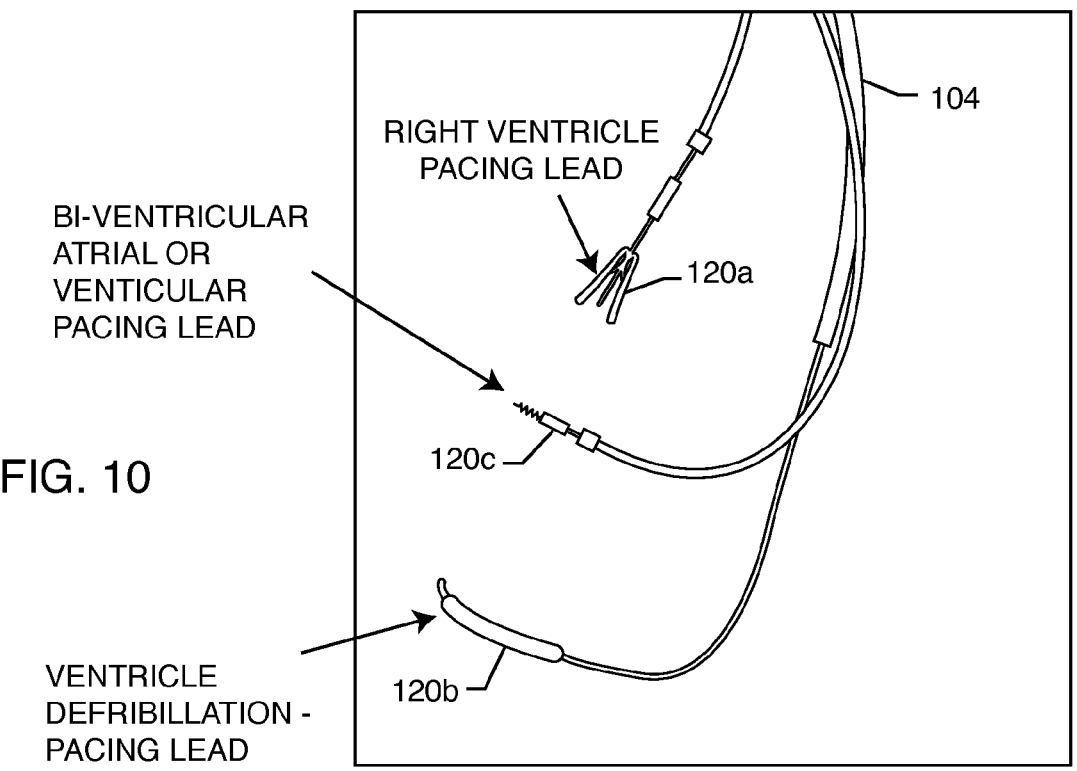
FIG. 10 is a line drawing of an exemplary patient cardiac X-ray of a bi-ventricular lead wire system.

FIG. 10 is a line drawing of an actual patient cardiac X-ray of one of the newer bi-ventricular lead wire systems. The new bi-ventricular systems are being used to treat congestive heart failure, and make it possible to implant leads outside of the left ventricle. This makes for a very efficient pacing system; however, the lead wire system 104 is quite complex. When a lead wire system 104, such as those described in FIGS. 3, 4 and 5, are exposed to RF fields, electric currents can be induced into such lead wire systems. For the biventricular system, electronic switches 124 would be incorporated at each of the three distal TIPs 120*a-c* so as to be in series with the respective lead wire.

Figure 11:
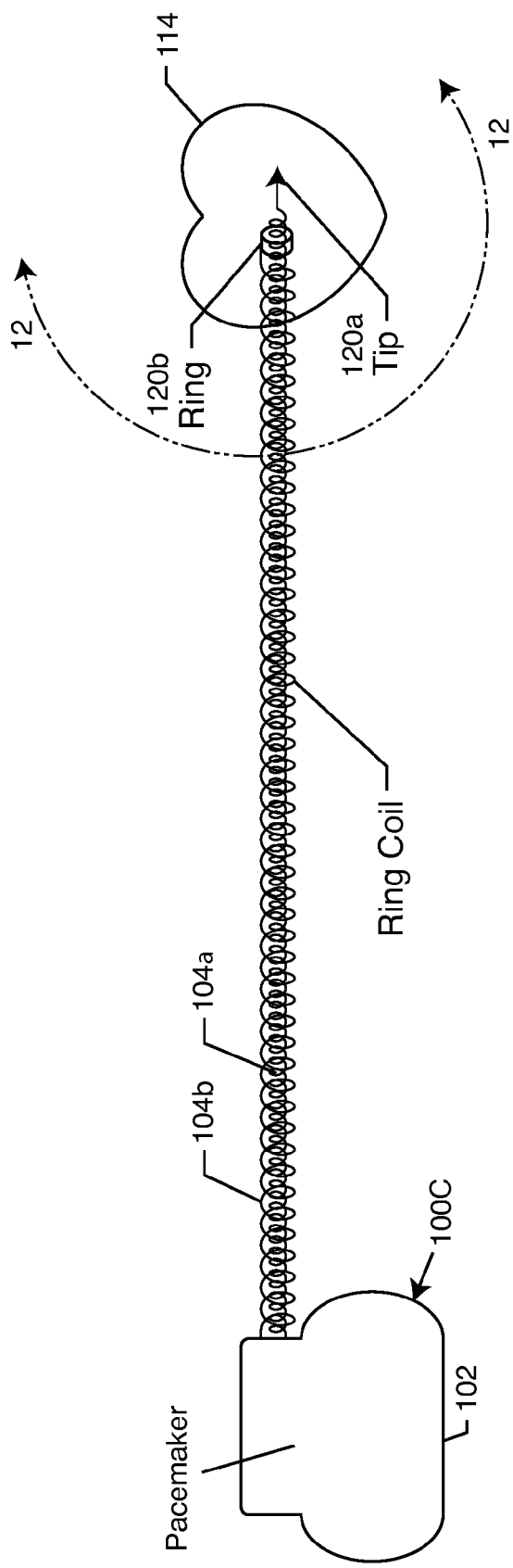
FIG. 11 illustrates a bipolar cardiac pacemaker lead wire showing the distal TIP and distal RING electrodes.

FIG. 11 illustrates a single chamber bipolar cardiac pacemaker lead wire showing the distal TIP 120*a* and the distal RING 120*b* electrodes. This is a spiral wound (coaxial) system where the RING coil 104*b* is wrapped around the TIP coil 104*a*. There are other types of pacemaker lead wire systems in which these two leads lay parallel to one another (known as a bifilar lead system).

Figure 12:
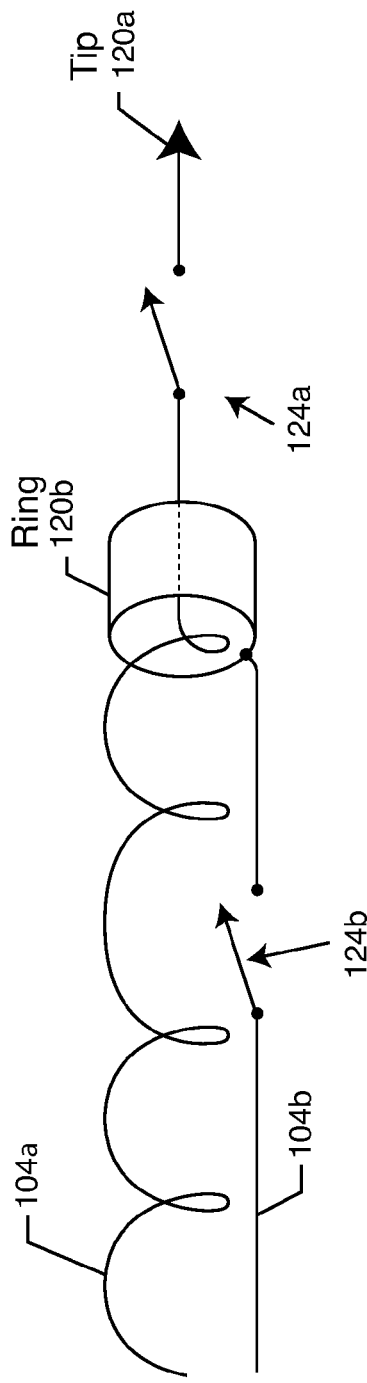
FIG. 12 is an enlarged, fragmented schematic illustration of the area illustrated by the line 12-12 in FIG. 11 with the electronic switches of the present invention shown in series with both the distal TIP and the RING electrodes.

FIG. 12 is a schematic illustration of the area 12-12 in FIG. 11 which incorporates the features of the present invention. In the area of the distal TIP 120*a* and RING 120*b* electrodes, electronic switches 124*a* and 124*b* have been placed in series with each of the respective RING and TIP circuits. The RING circuit wire 104*b* has been drawn straight instead of coiled for simplicity. Accordingly, at an MRI pulsed RF frequency, an open circuit will be presented thereby stopping the flow of undesirable MRI induced RF or gradient currents. The TIP 120*a* is designed to be inserted into intimate contact with myocardial tissue. Over time it becomes encapsulated and fully embedded or buried within such tissue. However, the RING 120*b* is designed to float within the blood pool, for example, in the ventricle or atrium. With the constant blood perfusion, the RING 120*b* is somewhat cooled during medical diagnostic procedures, such as MRI. However, the TIP 120*a* which is embedded in the myocardial tissue, is thermally insulated in comparison. It can't always be assumed that a RING electrode that is floating in the blood pool will be adequately cooled by the flow of blood. There are certain types of patients that have illnesses that lead to very low blood flow rates and perfusion issues. Accordingly, the operation of the novel electronic switch 124 is more important in the TIP 120*a* than it is in the RING 120*b* in order to prevent distal TIP heating and associated tissue damage. In most cardiac applications, only a TIP electronic switch 124*a* is required for MRI compatibility.

Figure 13:
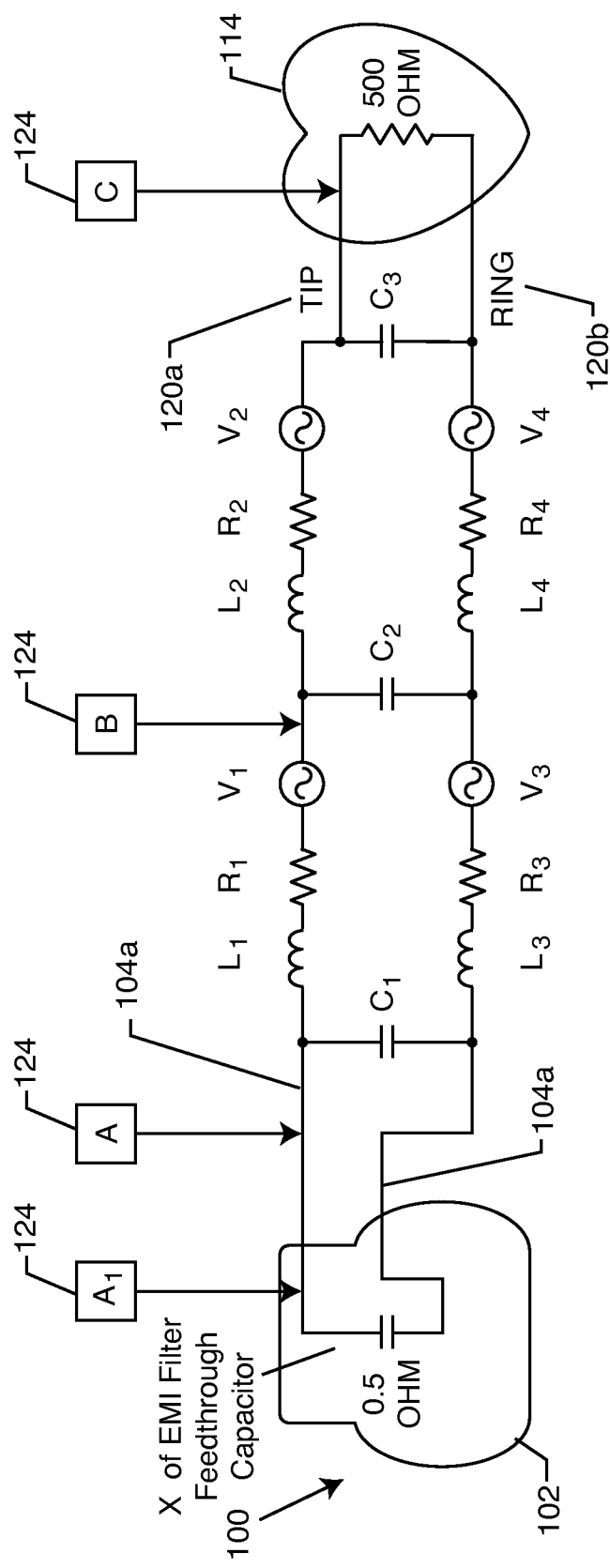
FIG. 13 is a schematic diagram showing the distributed electrical resistance and reactance components which make up the impedance of a pacemaker bipolar lead wire system with switch placement locations.

FIG. 13 illustrates an equivalent circuit diagram for a bipolar pacemaker lead wire system. On the left is the housing 102 of the pacemaker 100. The 0.5 ohm impedance represents the approximate reactance of a typical filtered feedthrough capacitor at high frequencies (around 128 MHz). As one can see, there are distributed inductances and resistances along the length of each lead wire 104*a* and 104*b* shown as $L_1$, $R_1$ and $L_2$, $R_2$. There are actually an infinite number of these as the lead wire system forms a transmission line. One can also see similar reactances $L_3$, $R_3$ and $L_4$, $R_4$ in the return path of the RING circuit. There is also distributive capacitance $C_1$, $C_2$ and $C_3$ between the closely wound or closely routed TIP and RING wiring 104*a* and 104*b*. One can see also that there are voltages $V_1$, $V_2$, $V_3$ and $V_4$ which represent electromotive forces (EMFs) induced by the gradient and RF pulsed fields of an MRI imaging machine, or similar imaging equipment or similar therapeutic equipment.

There are a number of choices for placement of the novel electronic switch 124 of the present invention. Choice $A_1$ would put the electronic switch 124 inside the housing 102 of the cardiac pacemaker 100. This would certainly be advantageous in order to protect the electronic switch 124 circuitry from body fluids. However, as one can see, the impedances of the lead wire system 104 isolate the pacemaker 100 from many of the induced voltages. In other words, it really doesn't matter if you have an open switch 124 at location $A_1$. The voltages induced in the MRI field at $V_2$ could still cause unacceptable heating or gradient currents to flow into body tissue. In this case, body tissue is myocardial tissue of a human heart 114. A better approach would be to put a switch 124 at locations A or B. However, the really optimal location that makes sure currents do not flow into body tissue or the human heart 114 in this example, would be location C. Accordingly, a preferred embodiment is to place the electronic switches 124 of the present invention either at or close to the distal TIP electrode 120.

Figure 14:
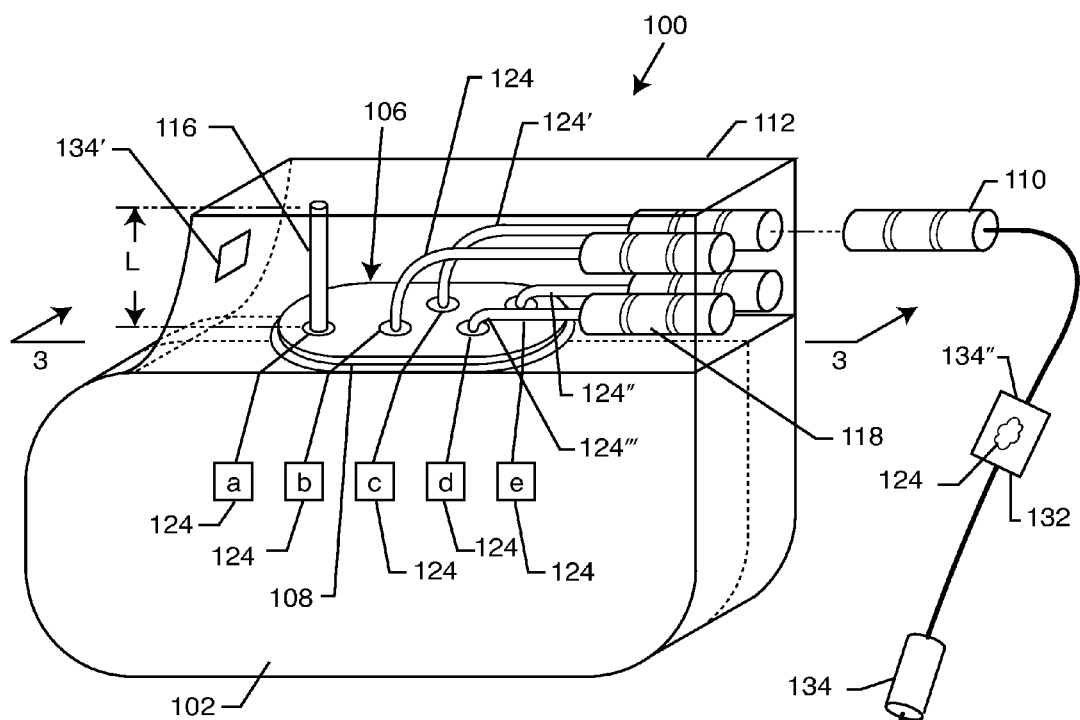
FIG. 14 is very similar to FIG. 2 and is a perspective and somewhat schematic view of an AIMD including electronic switches of the present invention, and optional RFID chips for identification of therapeutic imaging compatible AMDs and/or associated lead wire systems.

FIG. 14 is similar to FIG. 2 and shows locations where electronic switches 124 may be placed. First of all, the electronic switches 124, 124', 124" and 124'" could be placed in the header block 112 of the AIMD 110 which is outside the titanium shield 102. Location here allows for convenient activation by RF radio frequencies (such as RFID pulses). Another location would be inside of the AIMD housing 102 shown as locations 124A, B, C, D or E. Locations B, C, D and E are in series with the pacing and sensing outputs of the cardiac pacemaker. In order that the RF telemetry 116 circuits not be interfered with during MRI, or that electromagnetic interference from MRI not undesirably enter through the RF telemetry channel, it is also optional to have an electronic switch 124 in accordance with the present invention located at position A. This would have the effect of turning off pacemaker telemetry during the MRI procedure. Older pacemakers and older implantable medical devices often incorporate internal or external low frequency magnetic loop telemetry antennas. It will be obvious to those skilled in the art that an electronic switch 124A could also be placed in such a telemetry loop to defeat the possibility that it could carry on telemetry while in an MRI or similar imaging or therapeutic environment.

Referring once again to FIG. 14, one can see that there is an optional adapter 132 which would plug into the ports 118 and have electronic switches 124 in accordance with the present invention. Prior art lead wires, including their plugs 110, could then plug into the adapter. This would allow for convenient retrofitting of any prior art active implantable medical device and any prior art lead system to incorporate features of the present invention. Additional information can be learned from U.S. Patent Application Publication No. US 2008/0195180 A1 entitled LOW LOSS BAND PASS FILTER FOR RF DISTANCE TELEMETRY PIN ANTENNAS OF ACTIVE IMPLANTABLE MEDICAL DEVICES, the contents of which are incorporated by reference herein, which describes in more detail the operation of RF telemetry pin 116 circuits.

When placing the novel electronic switch filters 124 in a module 132 such as shown in FIG. 14, there are two options. One is to encapsulate the electronic switches 124 in a hermetic structure such that they are not exposed to body fluids. Another option is to make all of the materials and design of the electronic switches or MEMS switches 124 biocompatible. A discussion of this can be found in U.S. Pat. No. 6,985,347, the contents of which are incorporated by reference herein. In general, MEMS switches are the preferred embodiment which would utilize platinum or gold contacts and associated biocompatible structures.

Referring once again to FIG. 14, one can see that there are RFID chips 134, 134', and 134" that may be placed at different locations. It is noted that an RFID chip 134 is not shown inside of the shield housing 102 because it would not be possible for an RF interrogator to send signals to said RFID chip. RFID chips are well known in the prior art. They can be either powered (with a battery) or externally powered. The externally powered RFID chip is the preferred embodiment for the present invention. In this case, the electromagnetic field which is sent by the reader couples through an embedded antenna to power the microcircuit in the RFID chip. The RFID chip 134 can be affixed anywhere along the lead wire system 104 or the lead pocket. The RFID chip 134' can be incorporated within the header block 102 of an AIMD 100. Or the chip 134" can be included within a lead wire adapter 132 as shown. The purpose of the RFID chip 134 would be to disclose the presence of the MRI compatible electronic switches 124. In this way, a physician or radiology technician could very quickly determine if the patient's AIMD 100 and/or associated lead wire system 104 is outfitted with the electronic switches 124 and is therefore suitable for conducting an MRI examination. One is directed to U.S. Patent Application Publication No. US 2006/0212096 A1, entitled RFID DETECTION AND IDENTIFICATION SYSTEM FOR IMPLANTABLE MEDICAL DEVICES, the contents of which are incorporated by reference herein, for a more thorough explanation of these concepts. One is also directed to U.S. Patent Application Publication No. US 2008/0065181 A1, entitled RFID DETECTION AND IDENTIFICATION SYSTEM FOR IMPLANTABLE MEDICAL LEAD SYSTEMS, the contents of which are incorporated by reference herein.

Figure 15:
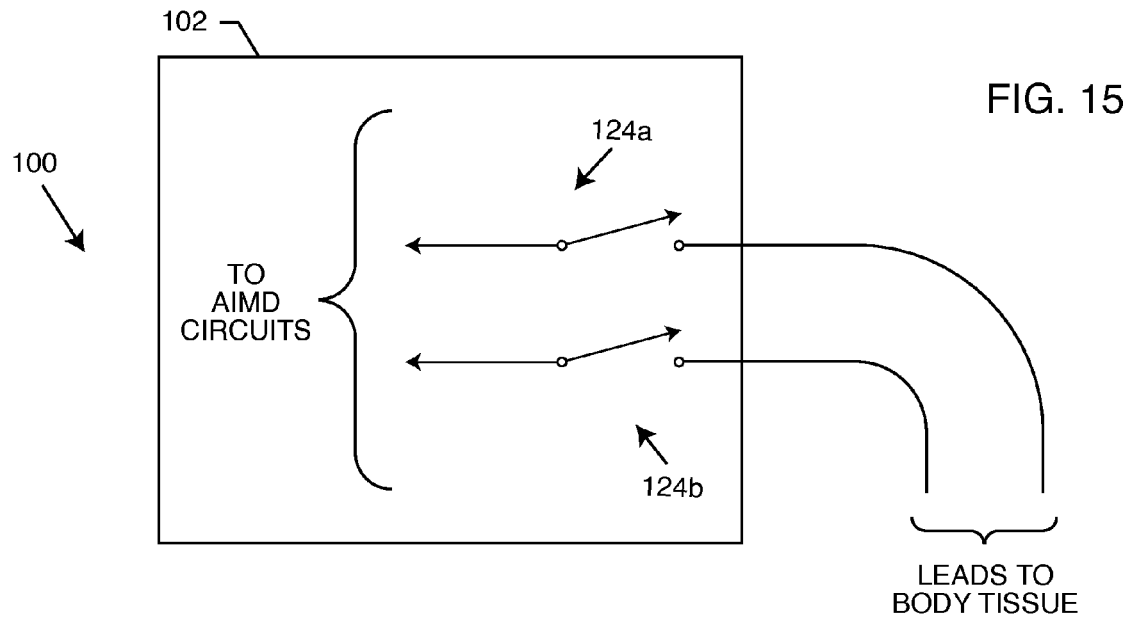
FIG. 15 is a line drawing of an AIMD showing electronic switches of the present invention.

FIG. 15 is an illustration of placing electronic switches 124a and 124b inside of housing 102 of an active implantable medical device 100. In this case, the switches 124a and 124b would be activated through the external programmer which is used to communicate with the active implantable medical device 100. Drop-down menus could be incorporated into the software of the external programmer in order to put the AIMD into an MRI conditional or MRI safe mode. This would be done prior to the patient's exposure to a medical diagnostic or therapeutic procedure such as MRI.

Figure 16:
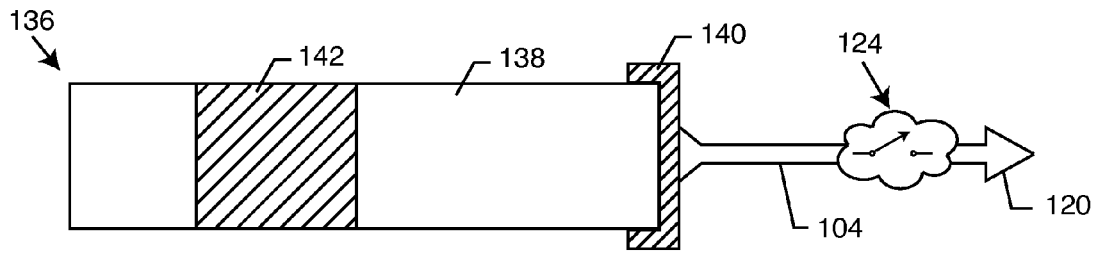
FIG. 16 is a side perspective view of a prior art neurostimulator known in the art as a bion having a lead incorporating a switch in accordance with the invention.

FIG. 16 illustrates an active implantable medical device 136 that may or may not incorporate implanted lead wires. This is known in the industry as a Bion. Bions generally come in two different categories. That is, certain Bions have an internal battery and are a stand-alone stimulation device used for urinary incontinence and other applications. These are generally large needle injectable systems. The Bion 136 generally is encased in a ceramic tube 138 that has an end cap electrode 140. The end cap electrode 140, for example, could be titanium or platinum and is generally welded or brazed to the ceramic tube 138 to make a hermetic seal thereby protecting the sensitive electronics that are inside of the ceramic tube 138 from damage due to body fluid. There is also an opposite polarity RING electrode 142 as shown. This particular device stimulates body tissue between the cap electrode 140 and the RING electrode 142.

Other types of Bions have no battery, but instead have a resonant coil. The device picks up its energy from an externally worn or externally placed pulsing magnetic field pack. A patient can wear some sort of a device around his or her waist or shoulder, for example, with a large battery and circuit coil that produces this field. The Bion would get its energy by coupling with this field. No matter whether the Bion 136 is passive or has an internal battery, it is still important to protect the internal circuits of the Bion from temporary or permanent malfunction due to the RF pulse frequency of MRI systems. There are also cases where the diameter of the Bion 136 is too large for it to effectively make contact with a precise location within a nerve or muscle. In this case, the Bion 136 may have an associated lead wire 104 with a distal TIP 120, as shown in FIG. 16. In this case, the end cap 140 and the lead wire 104 would be insulative wherein the electrical connection to body tissue would occur at distal TIP 120. A small diameter of lead wire 104 and distal TIP 120 allows the surgeon to tunnel the lead wire 104 into a precise location and have the Bion TIP 120 placed at a location within muscle, nerve or other body tissue where its location can be precise. However, lead wire 104 can act very much like pacemaker lead wires, in that it could act as an antenna and pick up undesirable RF fields from MRI. Accordingly, overheating of lead wire 104, in conjunction with the distal TIP 120, and/or coupling of electromagnetic interference into the circuits of the Bion 136 are a concern. Accordingly, electronic switches 124 could be placed in series with lead wire 104, as shown in FIG. 16, and/or be placed internal to the Bion 136, as shown in FIG. 17.

Figure 17:
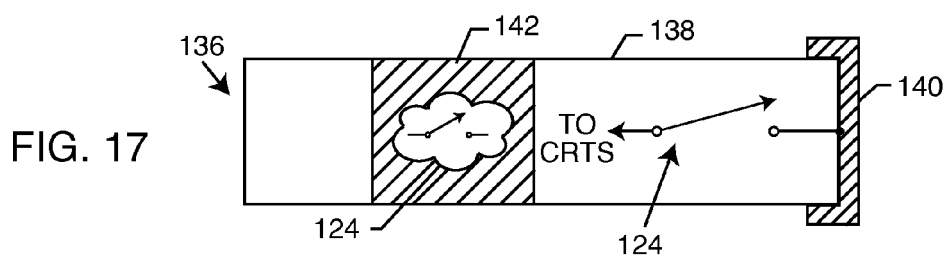
FIG. 17 is very similar to FIG. 16 with the addition of an electronic switch of the present invention into the bion itself.

Referring to FIG. 17, one can see an application of the present invention where inside of the Bion device 136 a novel electronic switch circuit 124 can be placed at the end cap electrode 140. This would prevent selected pulse RF frequencies, for example, those from a 3 Tesla MRI system from entering into and disrupting or damaging the sensitive electronics of the Bion 136. This placement is the preferred embodiment for the electronic switch 124 because not only will it protect the internal circuits, but it will also prevent MRI pulsed currents from flowing into the associated body tissues, or in the case of an external lead wire 104, it would prevent RF currents from flowing in that lead wire 104 as well.

Alternatively, the novel electronic switch circuit 124 of the present invention could also be placed at the ground electrode 142. One could also place electronic or mechanical switch circuits 124 at both the cap 140 and the ground 142 electrodes. This would make the Bion 136 resistant to 0.5 Tesla, 1.5 Tesla, 3 Tesla and even other MRI systems. This also eliminates currents from MRI low frequency gradient fields as well as the pulsed RF frequencies. The Bion 136 is just one example of an AIMD that may or may not have implanted lead wires. Other examples include drug pumps and the like. Accordingly, the present invention is very useful to protect the electronic circuits of active medical devices that do not have associated lead wires, from the high fields involved with certain hospital and other medical diagnostic procedures such as MRI.

Figure 18:
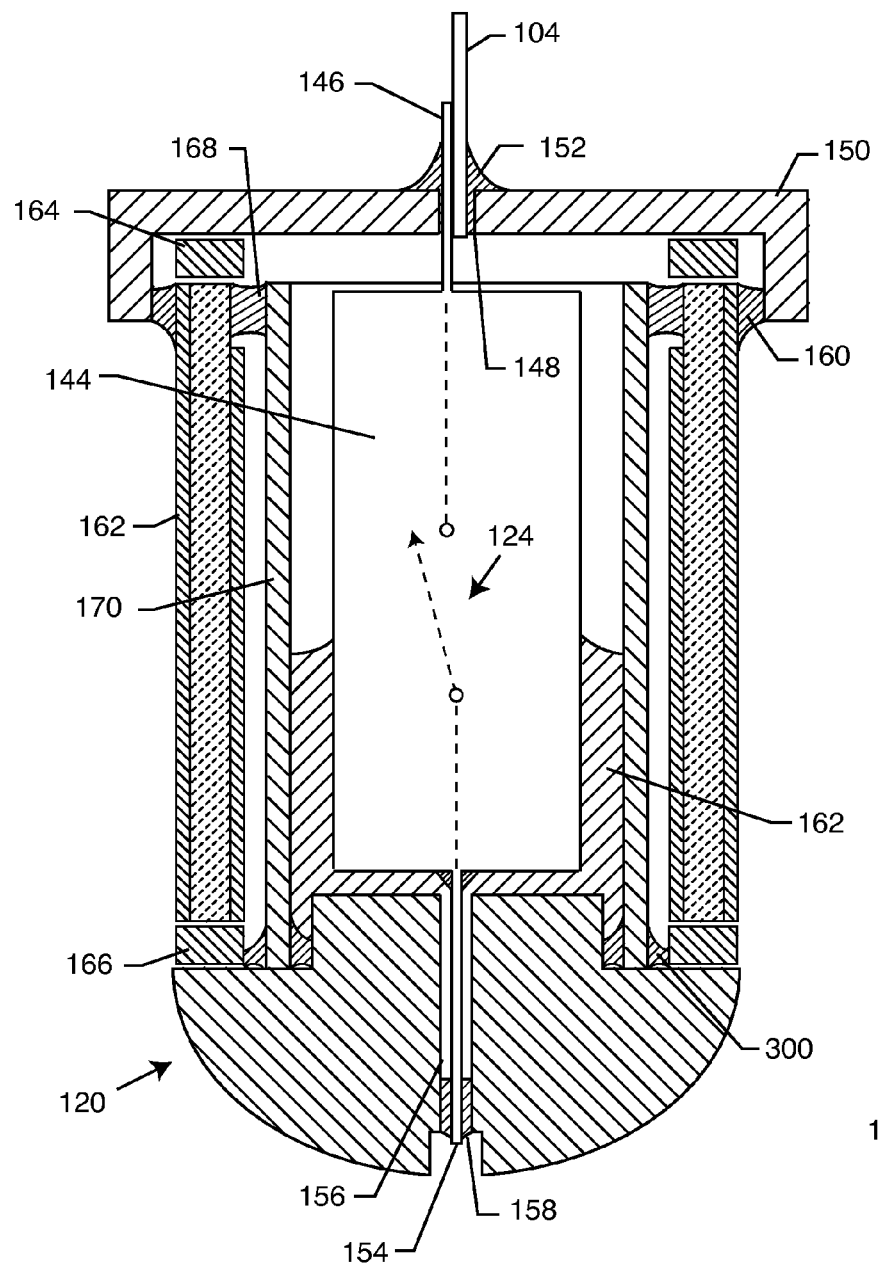
FIG. 18 is a sectional view illustrating an electronic switch module which has been hermetically sealed for protection against body fluids.

FIG. 18 illustrates a hermetic package incorporating a distal TIP electrode 120 into which an electronic switch module 144 having a switch 124 is placed. This package is extremely convenient as it places the electronic switch module 144 literally at the distal TIP electrode 120. This is optimal to prevent any current flow at all into body tissue. It also eliminates currents in this location such that overheating at the distal TIP 120 is prevented.

With reference to FIG. 18, in one embodiment, the lead wire 104 from the AIMD 100 is conductively coupled to a lead wire 146 extending from the switch module 144. This can be accomplished, for example, by having both lead wires 104 and 146 extending through one or more apertures 148 of an end cap 150, and conductively coupling either the lead wires 104 and 146 to one another, and/or to the end cap 150, such as by a laser weld 152, gold braze or the like. Another lead wire 154 extends, typically generally opposite the lead wire 146, through a passageway 156 of the TIP electrode 120 and is conductively coupled, such as by laser weld 158 thereto, although other means of conductively coupling the switch module 144 to the AIMD lead wire 104 and TIP 120 are within the scope of the invention. In this manner, the switch 124 of the switch module 144 can be selectively opened to prevent transmission of current and electrical signals between the distal TIP electrode 120 and the AIMD 100. The electronic switch module 144 is preferably a MEMS ohmic switch, although it could be a MEMS capacitive switch, or other type of electronic switch. Another alternative would be a mechanical switch which is externally activated.

Typically, the invention is embedded or inserted into bodily fluids or tissue. For example, the lead wire 104 could be part of a bipolar lead wire from a cardiac pacemaker. In this case, this would be the lead wire 104 to connect the distal TIP 120 (fixation clips not shown) which would contact myocardial tissue. In such cases, it is preferable to hermetically seal the switch module 144 from bodily fluids. This is done by encasing the module 144 in a hermetically sealing material, tube, or the like. FIG. 18 illustrates one possible hermetic seal arrangement. The end cap 150 could be laser welded or gold brazed 160 to an outer tube or cylinder 162. So as to electrically isolate the connection between the end cap 150 and the exterior cylinder 162, insulative washers 164 and 166 could be used. The outer cylinder 162 could then be coupled, such as by adhesion, laser weld, or the like 168 to an inner cylinder or sleeve 170, which would contain the switch module 144. A thermosetting polymer or the like could be used to mechanically hold the electronic switch module 144 in place within the inner cylinder or sleeve 170. Of course, it will be understood that a single cylinder or tube could be used to form a hermetic connection and seal between the end cap 150 and the tip 120. Alternatively, all of the materials used to construct the switch module 144 could be comprised of biocompatible materials, although this increases the cost of the switch module 144. It will be appreciate that the distal TIP 120, end cap 150, and outer cylinder 162 would need to be comprised of, or coated with, a biocompatible material.

Figure 18A:
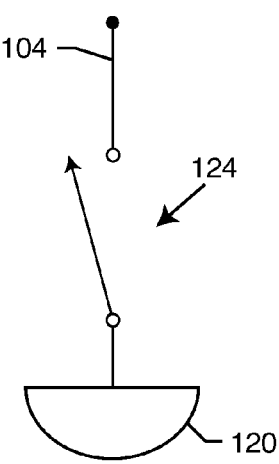
FIG. 18A is the schematic diagram of the circuit from FIG. 18.

FIG. 18A is a schematic drawing of the hermetically sealed electronic switch module previously described in FIG. 18.

FIG. 19 describes an alternative method of forming a hermetically sealed enclosure for the electronic module 144. In this case, the electronic switch module 190 incorporates an antenna structure 174 which activates an RFID circuit 176. The pulse from the RFID circuit 176 is sufficient to cause a MEMS switch 124 to activate. In this case, there is a distal TIP electrode 120 which is designed to intimately contact body tissue. An insulative cylinder 178 is preferably of either machined or pressed alumina ceramic, and includes sputtering 180 (such as a titanium-molybdenum layer) suitable for receiving a gold braze preform 182. The cylinder 178 is attached to biocompatible electrically conductive (preferably metallic) RINGS 184 and 186 as shown. Since RINGS 184 and 186 will be exposed to body fluid, they must be biocompatible and made of materials such as titanium, platinum or the like. The distal TIP 120 is laser-welded at 188 to the electrically conducting RING 184. The hermetic package shown by FIG. 19 is best suited for a rectilinear electronic switch module 150. Electrical attachment is made between the distal TIP 120 and the termination surface of the module 190 by means of a solder or thermal setting conductive adhesive 192. A gold sputter layer 194 or equivalent makes good electrical contact between the conductive attachment material 192 and the distal TIP 120. The electronic switch module 190 end terminations are shown at 196 and 198. A thermal setting conductive adhesive, solder, braze or the like 200 is used to form an electrical connection between the electronic switch termination 198 and a sputtered layer 202 on the back side of metallic end plate 204. The typically titanium or platinum end plate 204 has attachments 206 and 208 to lead wire 104. The end plate 204 is designed to be laser-welded at 210 to the biocompatible electrically conductive housing piece or RING 184. Material 212 is a non-conductive thermosetting polymer or adhesive. Its purpose is to provide mechanical support to the switch module 190. It can fill the entire space inside the hermetically sealed container or only a portion, as illustrated. A schematic diagram for the structure of FIG. 19 is shown in FIG. 20, wherein the electronic switch 124 is shown to be activated by RFID chip 176.

Referring to FIG. 20, one can see that the lead wire from the AIMD 104 enters into the switch 124. In this case, the switch 124 is an electrostatic MEMS switch. The electrostatic MEMS switch is activated from a signal or pulse from the RFID chip circuitry 176 which causes it as a cantilever to flip from a normally closed to an open position. The other end of this switch arrangement is connected to the distal TIP electrode 120. One can see that the MEMS switch 124 is shown open after it has received an electrostatic signal from the RFID chip 176. As previously mentioned, this could also be a magnetically activated MEMS switch in accordance with the present invention. In the case of magnetically activated MEMS switch, the antenna structure 174 and associated RFID chip 176 would not be needed. However, the MEMS switch components would include ferrite material such that they became sensitive to switching in a magnetic field.

Figure 21:
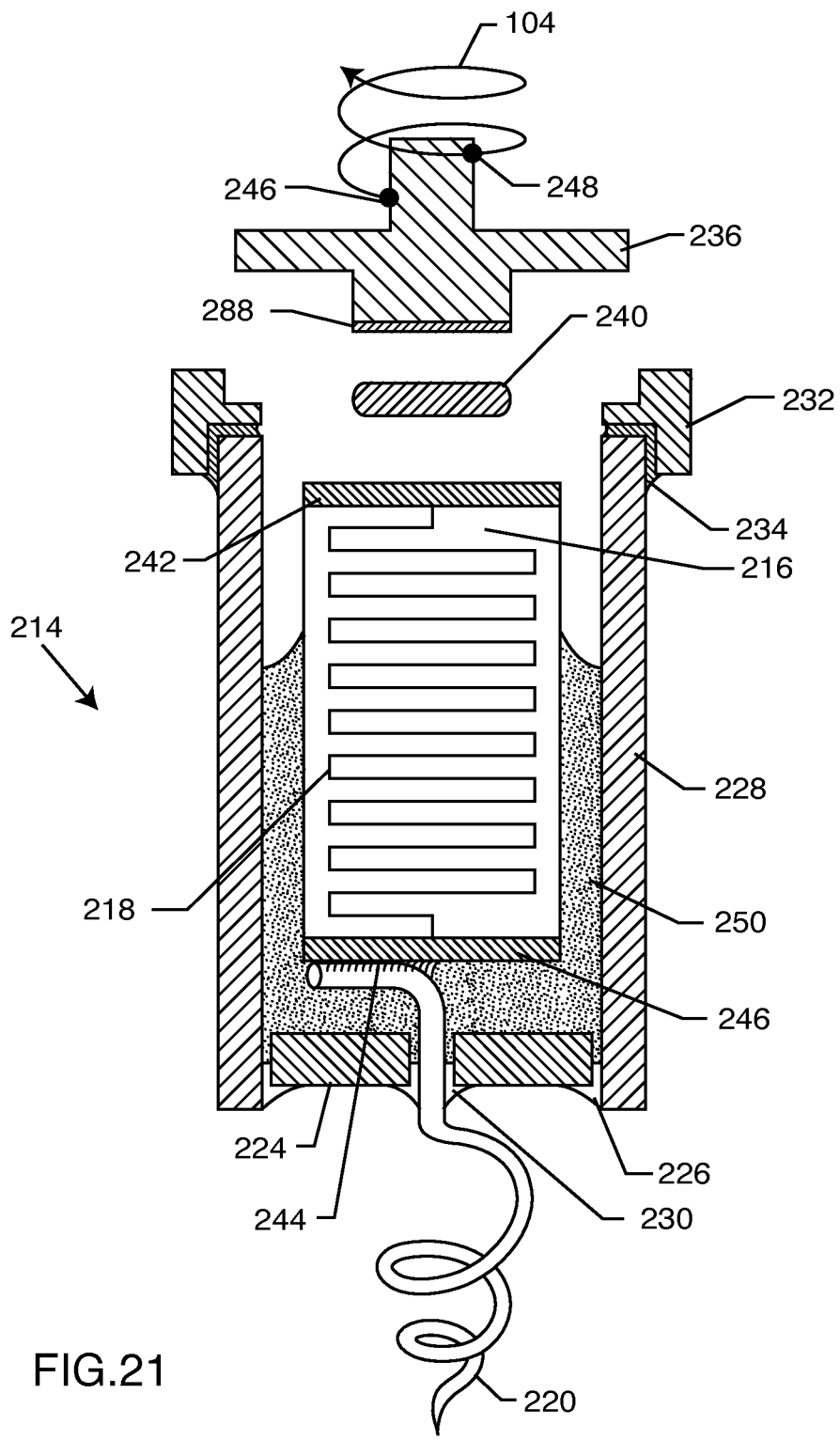
FIG. 21 is a sectional and partially exploded view of yet another hermetically sealed package containing the novel electronic switch which is RFID activated in accordance with the present invention.

FIG. 21 illustrates an alternative hermetically sealed package 214 that contains a novel electronic switch module 216 incorporating a switch 124 and RFID circuit 176, similar to that of FIG. 19. In this case, the electronic switch module 216 has a different type of RFID antenna configuration 218 as shown. In this case, there is a helix active fixation electrode 220 which is designed to be screwed into body tissue. This type of electrode 220 is well known in the prior art and is used to firmly affix a distal TIP, for example, into myocardial tissue. There is a biocompatible metallic end plate 224 which has been laser welded at 226 to the insulative tube 228 and also laser welded at 230 to the helix tip lead wire 220. At the opposite biocompatible metallic end RING 232 has been pre-attached by hermetic brazing or laser welding at 234 to the insulative tube 228. Biocompatible metallic end plate 236 is typically made of titanium, platinum or the like. It will be obvious to those skilled in the art for any of the inventions herein, that other biocompatible materials, such as tantalum, niobium and the like could also be used. Referring once again to end plate 236, one can see that there is a sputter area 238 in order to provide a highly conductive and oxide free surface. This sputter layer 238 would typically be gold, platinum or the like. Instead of sputter, this could also be applied by gold brazing, plating or other techniques. A solder or thermosetting conductive adhesive preform 240 is used for the seating of end plate 236. The end plate 236 is seated against this perform 240 and is then cured such that an electrical connection is made between the end plate 236 and the end metallization surface 242 of the module 216. The helix TIP 220 has an electrical attachment 244 to the opposite end metallization surface 246 of the module 216. The end plate 236 is designed to be laser welded into the inside diameter (counter-bore) of the mating RING 232 forming a hermetic seal. The lead wire 104 coming from the implantable medical device is then attached by laser welding to a stub on the end plate 236 at point 246 and optionally at point 248. Additional attachment points can be added for additional mechanical strength. Material 250 is typically a non-conductive thermo setting polymer or adhesive, which provides mechanical support to the switch module 216. The polymer or adhesive can fill the entire space inside the hermetically sealed container 214, or only a portion, as illustrated.

Figure 22:
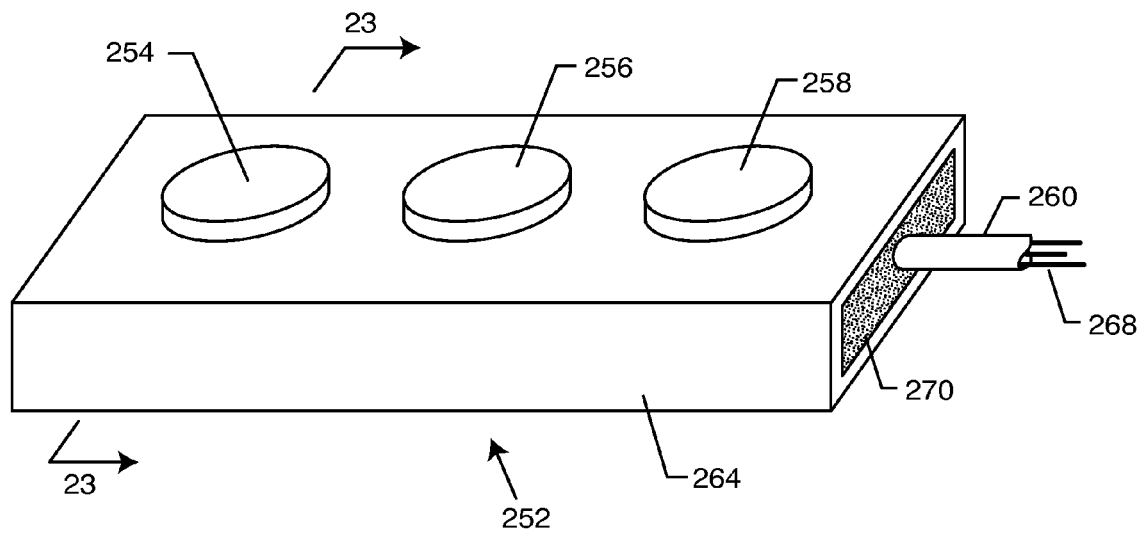
FIG. 22 is a perspective view of a distal electrode pad applicable to a wide variety of neurostimulator and neuromodulator applications.

FIG. 22 illustrates a distal electrode pad 252 applicable to a wide variety of neurostimulator applications. Neurostimulators include cochlear implants, deep brain stimulators, spinal cord stimulators, incontinence stimulators, general pain control stimulators, Vagus nerve stimulators, Parkinson's tremor control stimulators and the like. Typical prior art stimulators often come with a variety of pads such as that shown in FIG. 22. Three neurostimulation electrodes 254, 256 and 258 are shown, however, these can vary anywhere from one, ten or even 20 or more neurostimulation electrodes. For example, in cochlear neurostimulators, there are commonly sixteen wires, which are inserted in a bundle of electrodes to make contact to the auditory nerves. Referring back to FIG. 22, one can see that there is a lead wire bundle 260 which contains three wires that are connected to an external or implanted active medical device 252.

Figure 23:
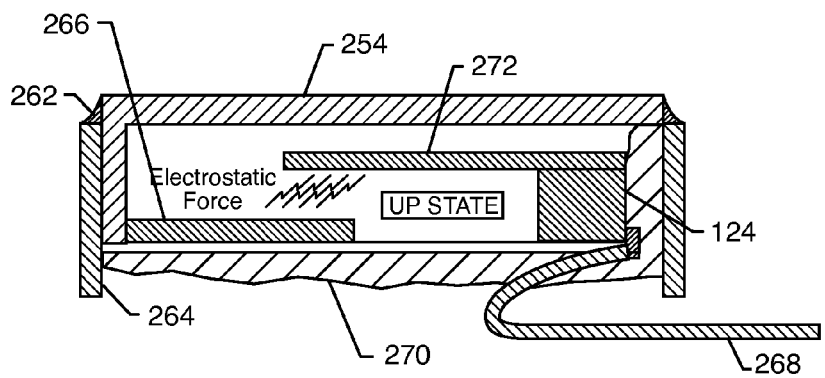
FIG. 23 is a sectional view taken generally along the line 23-23 of FIG. 22 showing the embedded switch in the open position

FIG. 23 is a cross-sectional view taken generally along line 23-23 of FIG. 22, and illustrating one form of the novel electronic switch 124 of the present invention. One can see that there is an electronic MEMS switch 124 located within the electrode assembly 254. The electronic switch 124 can be a prior art electronic or MEMS switch or equivalent. In this case, the distal TIP electrode pad 254 has a laser weld or equivalent biocompatible electrical attachment 262 to the surrounding metallization 264 of the cylindrical ceramic insulator structure 254. The electrode pad 254 is electrically connected to the cathodic contact 266 of the MEMS switch 124. The cathodic contact 266 is rigid in this case and is not free to move. Lead wire 268 is then routed through the flexible neurostimulator pad insulation/encapsulant 270 (also as shown in FIG. 22) and is electrically connected to the anodic MEMs contact cantilever 272 as shown. In FIG. 23, the MEMS switch 124 is shown in the up or open state wherein no currents can flow through it. This is the ideal position for MRI imaging or other procedures such as surgical electrocautery (Bovi knife for example) requiring high RF energy.

Figure 23A:
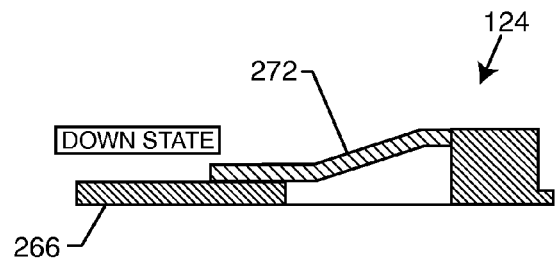
FIG. 23A is a view of the switch of FIG. 23 now shown in the closed position after application of electrostatic or external magnetic force.

FIG. 23A shows the MEMS switch 124 of FIG. 23 in the down or closed state. In this position, biological sensing and therapy signals freely pass through the switch 124.

Figure 24:
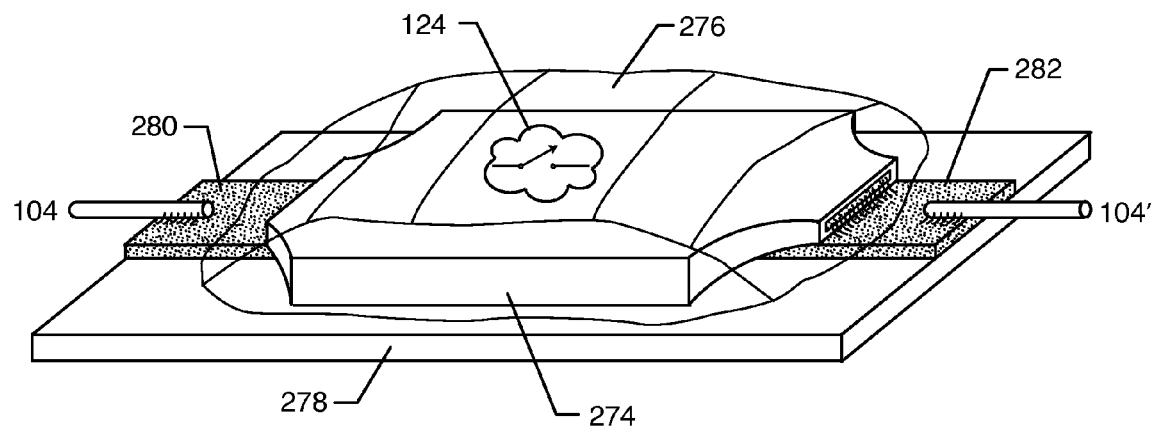
FIG. 24 is a perspective view of a novel electronic switch which has been embedded on a substrate with a hermetic seal or encapsulant for protection against body fluids.

FIG. 24 illustrates the novel electronic switch assembly 124 of the present invention shown in an encapsulated switch assembly or module 274 convenient for location anywhere in the lead wire 104 circuit. In this case, the entire module 274 has been overlaid with a suitable glass seal 276. This glass 276 can be deposited as a frit or molten and then sintered at high temperature. The glass 276 is designed to adhere to the substrate 278 and the wire bond pads 280 and 282 such that it forms a hermetic seal over the entire switching circuitry 274 of the present invention. Material 276 can be any number of borosilicate or compression glasses or even polymer sealants such as silicone and the like.

Figure 25:
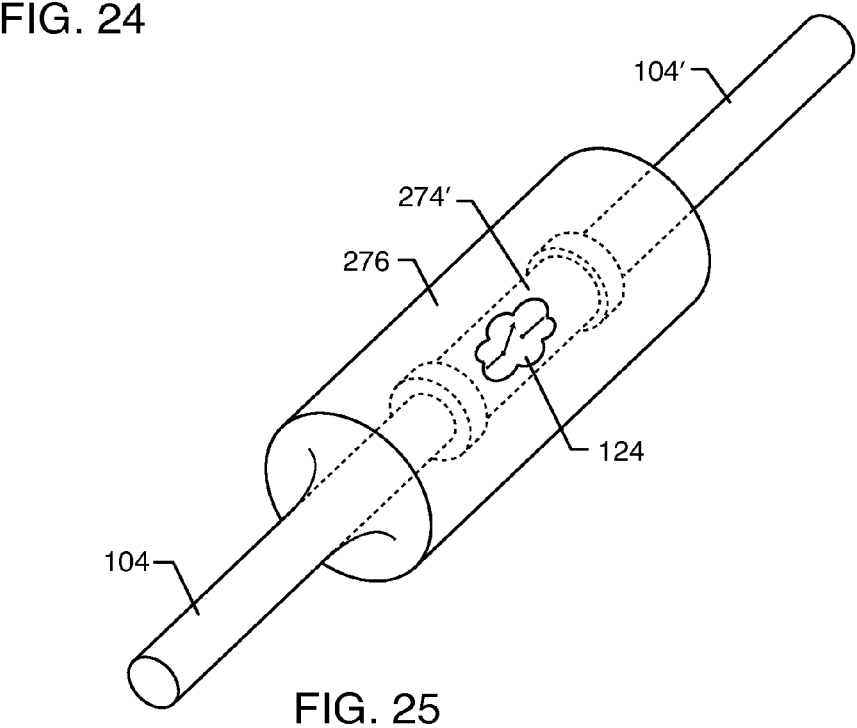
FIG. 25 is an alternate cylindrical encapsulation of an electronic switch which is very similar in principle to FIG. 24.

FIG. 25 is a representation of how one could also glass hermetically seal 276 any of the novel switch assemblies 274' incorporating electronic switches 124 of the present invention. It will be obvious to those skilled in the art that the hermetic seal 276 could be of ceramic, sapphire, glass and can be sealed in a variety of ways to prevent the intrusion of body fluids into the sensitive capacitor or inductor element embedded therein. The hermetic seal structure 276 shown in FIG. 25 is easiest done by glass. There are a number of prior art glass sealing processes that are used for capacitors and diodes and the like. In the art, many of these are known as DAP sealers.

Figure 26:
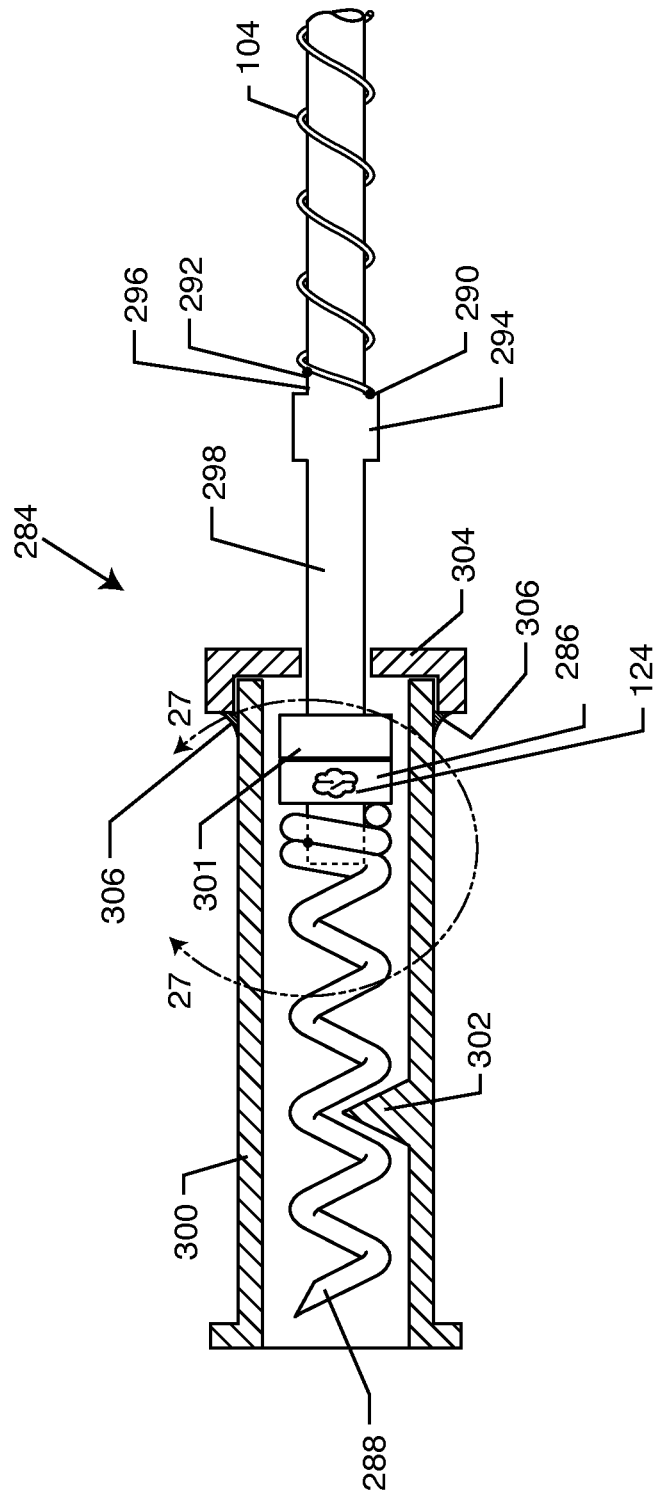
FIG. 26 is a cross-section of an active fixation cardiac electrode tip incorporating an electronic switch of the present invention.

FIG. 26 shows a prior art pacemaker active fixation distal TIP 284. A novel electronic switch module 286 is shown in close proximity to the helix tip 288. By having the electronic switch 286 in immediate proximity to the distal TIP 282, one can prevent the flow of MRI induced gradient and RF pulsed currents into myocardial tissue. One can see the lead wire 104 is routed from the output of the implantable medical device. Typically, this lead wire 104 would be constructed of biocompatible alloy MP-35N and laser welded at points 290 and 292 as shown. Optional stop 294 is shown and can be laser welded 296 in place on the spline 298. This would typically be done after assembly. The entire electronic switch 286 can be done with the helix 288 outside of its housing 300. This allows for easier electrical and mechanical connections (assembly), and enables high reliability screening of the switch 286, such as thermal shock, burn in, and the like. This is very important so that the electronic switch 286 will be highly reliable in the patient application. Once all of this testing has been done, the entire assembly consisting of helix 288, electronic switch 286, spline pedestal 314 and spline 298 can be inserted by screwing it past guide 302 and into the cylinder 300 from the right side. Then, end cap 304 is placed over the spline shaft 298 and laser welded 306 in place. It is not necessary that laser weld 306 be 360 degrees (only spot attachments are required). Subsequently, stop 294 can be laser welded 296 in place onto the shaft 298 as shown. Then the lead wire 104 consisting of MP-35N alloy can be laser welded at points 290 and 292 as shown, which completes the assembly.

Figure 27:
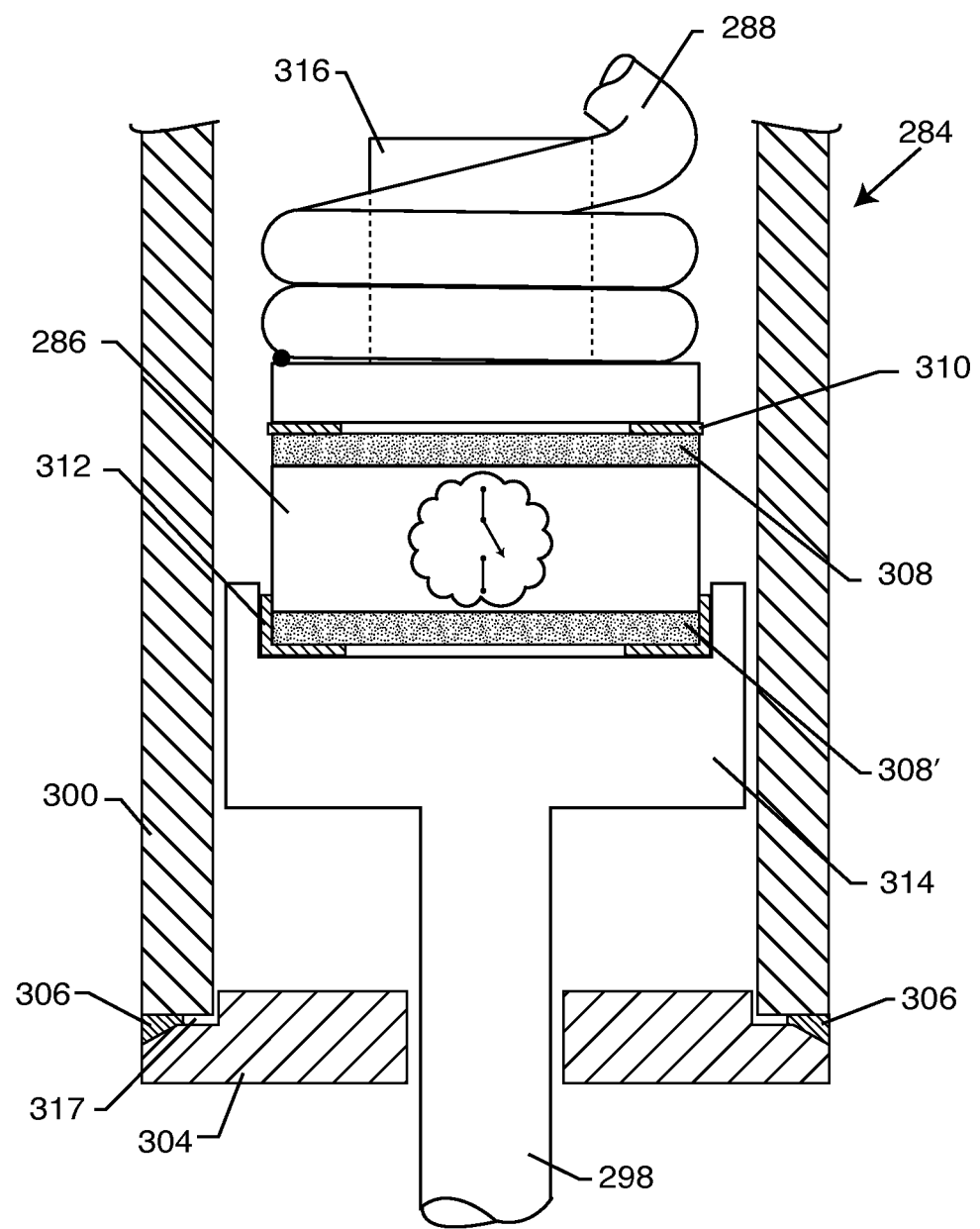
FIG. 27 is a sectional view of a cardiac active fixation tip electrode embodying the novel electronic switch which has been gold brazed to provide torsional strength.

FIG. 27 illustrates applying the novel electronic switch assembly 286 to a prior art active fixation distal TIP 284 previously described in FIG. 26. In this case, the electronic switches are MEMS switches in package 286 such that it has convenient external gold metallization surfaces 308. This is convenient because this entire assembly 286 can be directly brazed via braze preforms 310 and 312 into the active fixation assembly. This protects the relatively sensitive MEMS switch within the hermetically sealed package 286. As the physician applies torque along the shaft 298, this entire assembly and its associated helix tip 288 is designed to be screwed into body tissue. The hermetic package 286 is very strong and robust thereby protecting the sensitive electronic switches from the torsion during insertion into body tissues.

Referring once again to FIG. 27, one can see the attachment from the metallization 308' of novel electronic switch module 286 shown attached to the spline and spline pedestal 298 and 314. This is typically accomplished by the gold braze preform 312. In this case, the pedestal 314 has been counterbored to receive the end of the electronic switch assembly package 286. This allows the gold braze material 312 to angle up along the sides of the electronic switch package 286, thereby adding sheer strength to the overall assembly. This same counterbore could also be applied to the helix pedestal post assembly 316. This would allow gold braze material 310 to also come around the sides of the electronic switch module 286 to provide sheer strength in that area also. A similar gold braze preform 310 is used to attach a distal TIP helix pedestal 316 to the metallization 308 of the electronic switch 286. Of particular advantage is that the electronic switch 286 substrate can be constructed entirely of low k, very high strength ceramics. In this case, pure alumina or porcelain would be preferred embodiments. These have the advantage of being mechanically very rugged and also very rugged to thermal shock such that it would take pure gold brazing. By use of all biocompatible materials, the assembly is greatly simplified in that it need not be hermetic. It would also be possible to replace the gold brazes 310 and 312 with equivalent laser welds.

Referring once again to FIG. 27, one can see that the end cap 304 has been modified to make it flush with the outside diameter of the active fixation TIP assembly 300. This allows one to increase the inside diameter allowing room for the counterbore as previously described. The metallic end cap 304 has been stepped so that it is seated for convenient fixturing and also provides a countersink 317 for convenient gold brazing or laser weld material 306.

Figure 28:
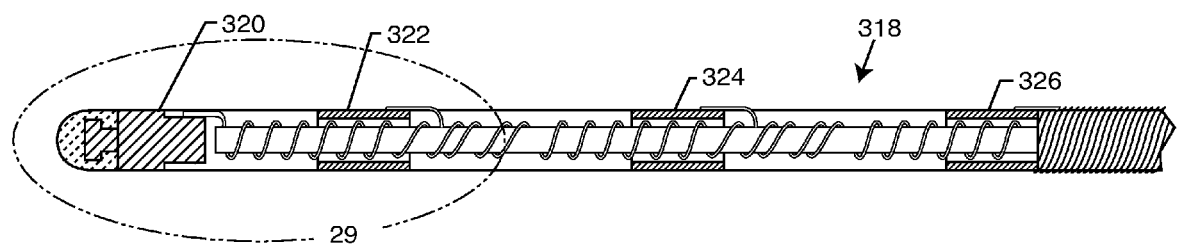
FIG. 28 is a fragmented sectional view of a prior art neurostimulation electrode probe.

FIG. 28 shows a prior art deep brain stimulator or other type of neuromodulation electrode 318. There are electrode RING assemblies shown at locations 320, 322, 324 and 326.

Figure 29:
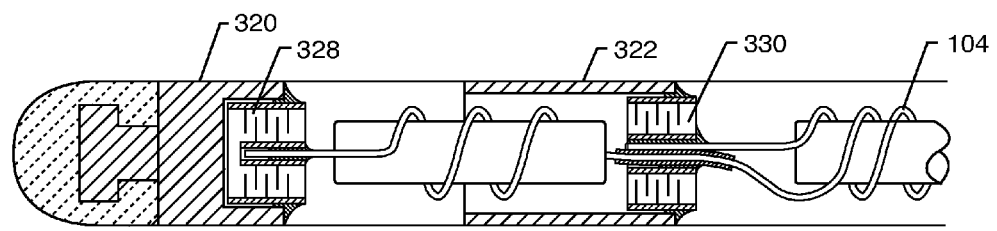
FIG. 29 is an enlarged sectional view of the area 29 in FIG. 28 illustrating the addition of electronic switches in accordance with the present invention.

FIG. 29 is an enlarged view of an electrode embodying the present invention and similar to area 29-29 from FIG. 28. One can see that there are MEMS electronic switches 328 and 330 that are placed in a position to put them in series with the lead wire 104 before it contacts the electrode surfaces 320 and 322. These switches, of course, can be any electronic switch in accordance with the present invention. In this case a matrix of multiple MEMS cantilevers are used to facilitate higher currents.

Figure 30:
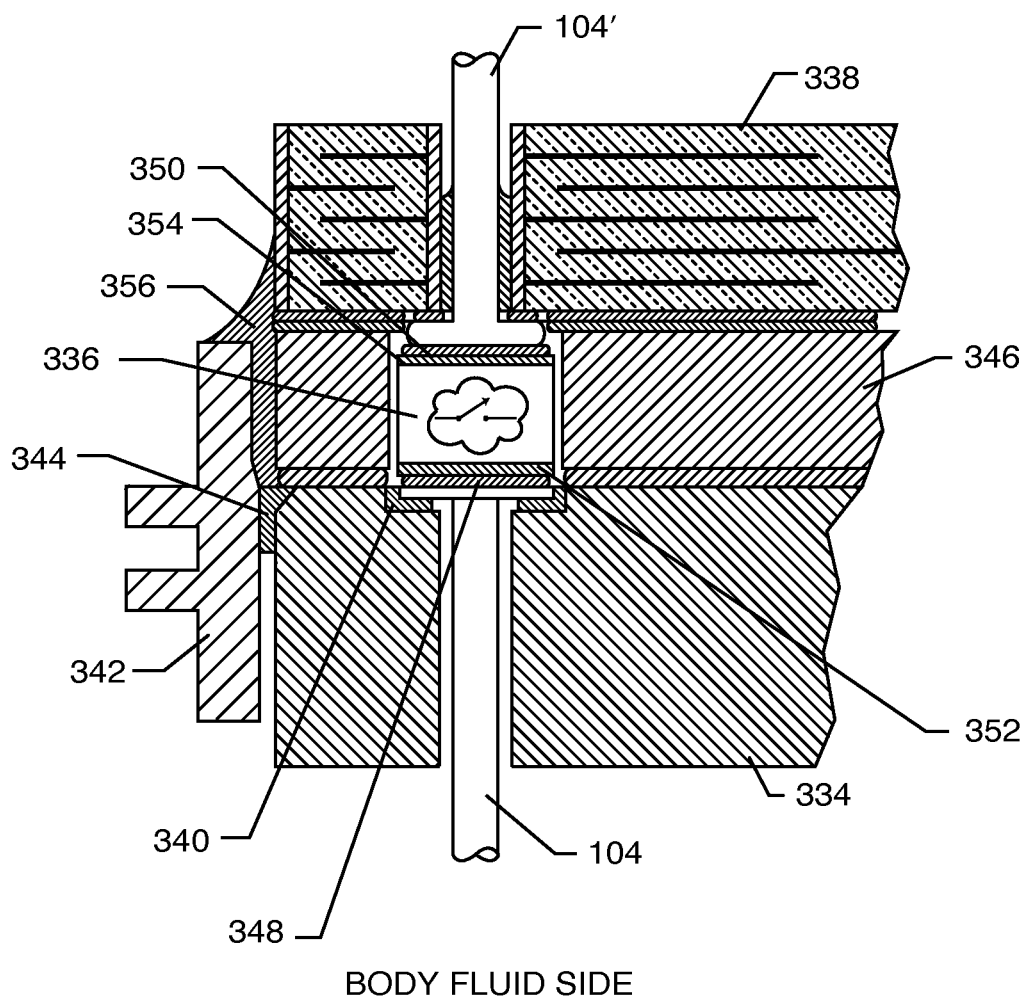
FIG. 30 is a fragmented sectional view of a prior art broadband low pass filter capacitor illustrating how an electronic switch in accordance with the present invention is incorporated therein.

FIG. 30 illustrates the hermetic seal of an AIMD. Lead wires 104 are typically routed from the outside (body fluid side) through the hermetic seal to the inside. In this case, lead wire 104 has been broken into discontinuous nail head segments 104 and 104'. Lead wire 104 extends through an alumina ceramic 334 which is fixed to the end of lead wire 104 at location 340, such as by laser weld, gold braze or the like. The alumina ceramic 334 is also attached to a ferrule 342 at location 344, by gold braze or the like. Although not shown, the housing of the AIMD is typically welded to the ferrule 342, so as to create a hermetic seal therewith. The switch assembly 336 is electrically connected to the lead wire segments 104 and 104'. It may be disposed within a plate or substrate 346, which can be an alumina ceramic, plastic or any other insulative material suitable for placing the switch assembly 336 therein. The plate 346 could also be an inductor slab as described in U.S. Pat. No. 6,999,818. The electrical attachment between the lead wire segments 104 and 104' to the switch assembly 336 is made by electrical connection material 348 and 350. Typically, the ends of the switch assembly 336 are metalized at 352 and 354 so as to create an electrical connection therebetween. The plate or slab 346 and a feedthrough capacitor 338 are coupled to the ferrule 342 at location 356. Typically, the adhesive 356 is a conductive adhesive such that the grounding electrodes are conductively coupled to the metallic ferrule 342, as is well known in the art. The electronic switch 336' has been placed between the lead wire 104 and the typical prior art EMI feedthrough capacitor 338. The electronic switch 336" could also be placed in other locations within the AIMD. However, referring back to FIG. 30, this particular location is the preferred embodiment as when the switch is open it then becomes impossible for high frequency RF signals from medical diagnostic or therapeutic equipment, such as MRI, from entering into the shielded housing of the AIMD. Once such EMI is inside, it can readily cross couple or re-radiate to adjacent sensitive circuits, such as pacemaker sensing circuits. This can cause disruption or even the delivery of inappropriate therapy. There have been cases of inadvertent ICD discharge during MRI procedures, for example. Accordingly, the electronic switch can be placed at or near the input or point of ingress or egress of lead wires 104 to the AIMD. As previously described, it would also be preferable to place an electronic switch near the distal TIP electrode 120 to prevent induced currents from flowing into body tissue.

Figure 31:
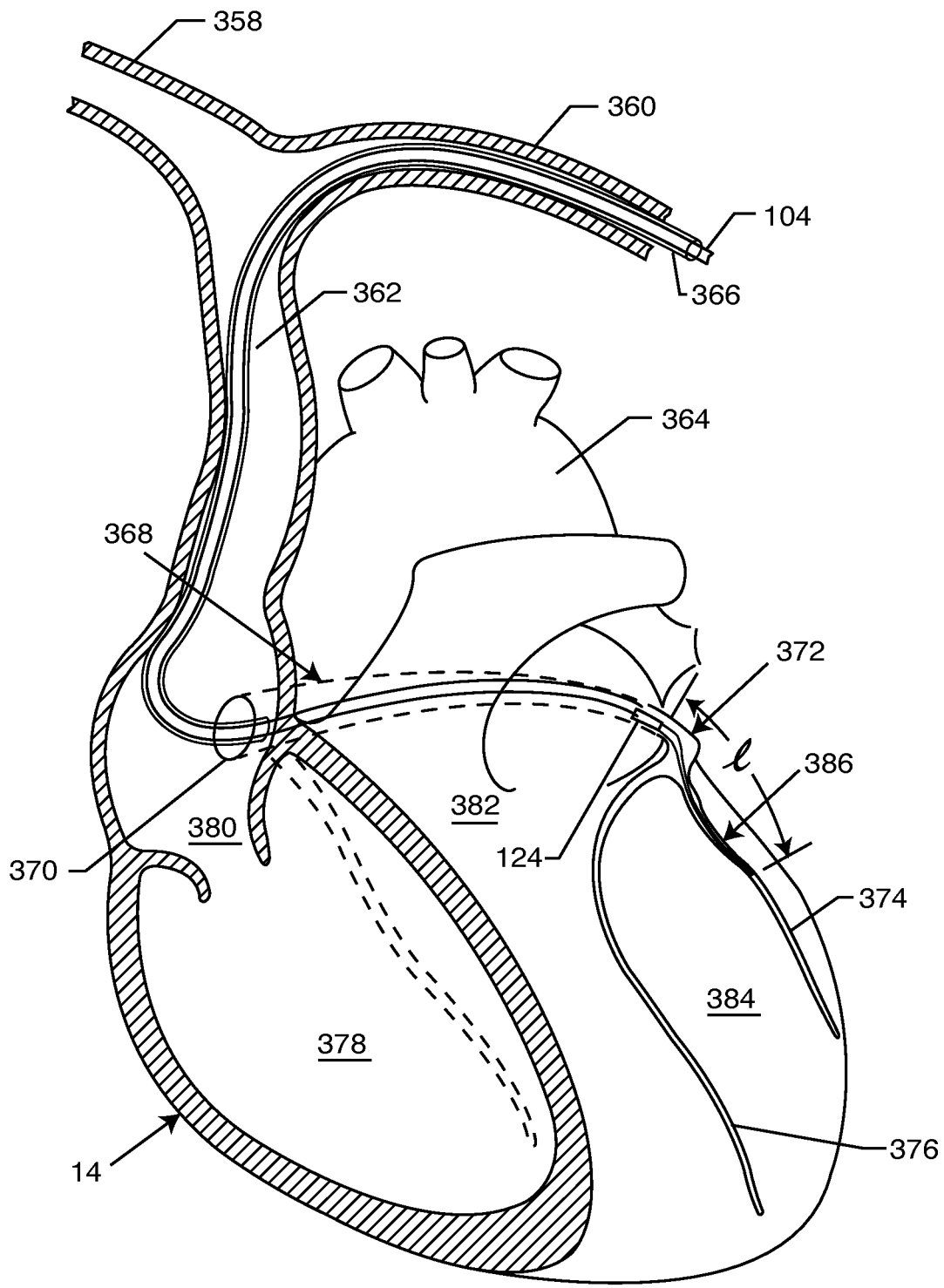
FIG. 31 is a diagrammatic representation of the human heart, showing a left ventricular (LV) endocardial lead system embodying the present invention.

FIG. 31 is a diagrammatic representation of a human heart 14 which includes right and left subclavian veins 358 and 360 respectively, the superior vena cava 362 and the aorta 364. A lead wire 104, which is typically routed from a biventricular cardiac pacemaker or a biventricular implantable cardioverter defibrillator (ICD) (which are not shown), is routed through a catheter 366 and directed, in this case, through the left subclavian vein 360 and then down through the superior vena cava 362 and into the coronary sinus 368. The lead wire 104 must first enter the coronary sinus ostium 370 where the implanting physician selects the correct location. The coronary sinus 368 is actually divided into two zones: the first part (on the left) is known as the coronary sinus 368; and the second part (on the right) is called the great cardiac vein 372. The great cardiac vein 372 wraps around the back of the left ventricle. The novel electronic switch 124 of the present invention is intended to be placed ideally near the end of the great cardiac vein 372 where it breaks into several venous branches 374 and 376.

Referring once again to FIG. 31, one can also see the right ventricle 378 and the right atrium 380, and the left atrium 382 and the left ventricle 384. The ideal location for a proximal electronic switch 124 is shown. An ideal length for the proximal electronic switch 124 would be between 5 and 7.5 mm in length. At this particular location, at the end of the great cardiac vein 372, cardiac motion is relatively small and fibrotic tissue will tend to encapsulate the electronic switch 124 and its lead wires 104 and thereby attach it/fixate it in position in this relatively low motion region. This is a particular advantage to the present invention, in that the lead 104 will remain highly reliable and resistant to breakage. Because of the relatively large diameter of the coronary sinus 368 and the great cardiac vein 372, this portion of the lead wire system, including the electronic switch 124, can be of much larger diameter (for example, 7 or 8 French). Beyond this point, where the great cardiac vein 372 branches, the venous systems become much smaller. In general, these branches are below 6 French in diameter and ideal electrode sizes go all the way down to 3 French.

FIG. 32 shows the relationship between French size, millimeters and inches. Since left ventricular pacing is important for cardiac resynchronization and treatment of congestive heart failure, it is a feature of the present invention that a lead wire reduction occurs at the point of egress of the electronic switch 124 allowing insertion of electrodes into the small diameter venous system in the proper position outside the left ventricle 384.

The primary benefit of locating the electronic switch 124 in the coronary sinus 368 and/or great cardiac vein 372 is that the diameter of the electronic switch 124 itself can be larger making it much easier to manufacture. The distal portion 386 of the lead 104 from the electronic switch 124 is smaller (3 to 6 French size) for easier employment and navigation into the branch veins of the left ventricle 384. Secondary benefits beyond the diameter of the electronic switch 124 include the length of the electronic switch. Entering into and navigating the coronary sinus 368 and great cardiac vein 372 generally involve larger bend radii compared to accessing and navigating the branch vessels. Therefore the portion of the lead 386 that traverses through and resides in the branch vessels must be very small and very flexible, not having a stiff section longer than approximately 1.5 mm as a rule of thumb. Rigid sections of the lead 104 measuring longer than 1.5 mm can impede the ability to navigate around the tight corners and bends of the branch vessels. In the coronary sinus 368 and great cardiac vein 372, however, there is substantially more latitude, and stiff sections of the lead could approach 5 mm or even 7.5 mm without drastically impeding deliverability. A secondary benefit of locating the electronic switch 124 in the coronary sinus 368 or the great cardiac vein 372 has to do with MRI image artifacts. Although the image artifact will be quite small due to avoiding the use of ferromagnetic materials, it is still beneficial to locate the electronic switch 124 away from the coronary arteries, ventricular wall motion or other anatomies/physiologies/pathologies of most interest. Location of this area is particularly important for example for a magnetically activated MEMS switch. By definition a magnetically activated MEMS switch incorporates ferrite materials in its cantilever beam system. The presence of ferrite materials will introduce a certain amount of image artifact. Therefore by locating the switch away from the anatomies of most interest, imaging of the left ventricle can still be accomplished. If the electronic switch 124 is located in the coronary sinus 368, however, it could generate small artifact in the vicinity of the valves. Another benefit of having the electronic switch 124 located in the coronary sinus 368 or the great cardiac vein 372 is that its rigidness provides a foundation on which fixation fixtures may be more strategically utilized. For example, one or more tines could originate from the region of the lead where the electronic switch 124 resides. Additionally, rigidness of the electronic switch 124 makes the tines more effective in their engagement of the vessel walls. Alternatively, a rigid portion of the lead 104, skillfully navigated beyond a corner or bifurcation, can function as a fixation mechanism that proves difficult or requires skill to track the lead.

Figure 33:
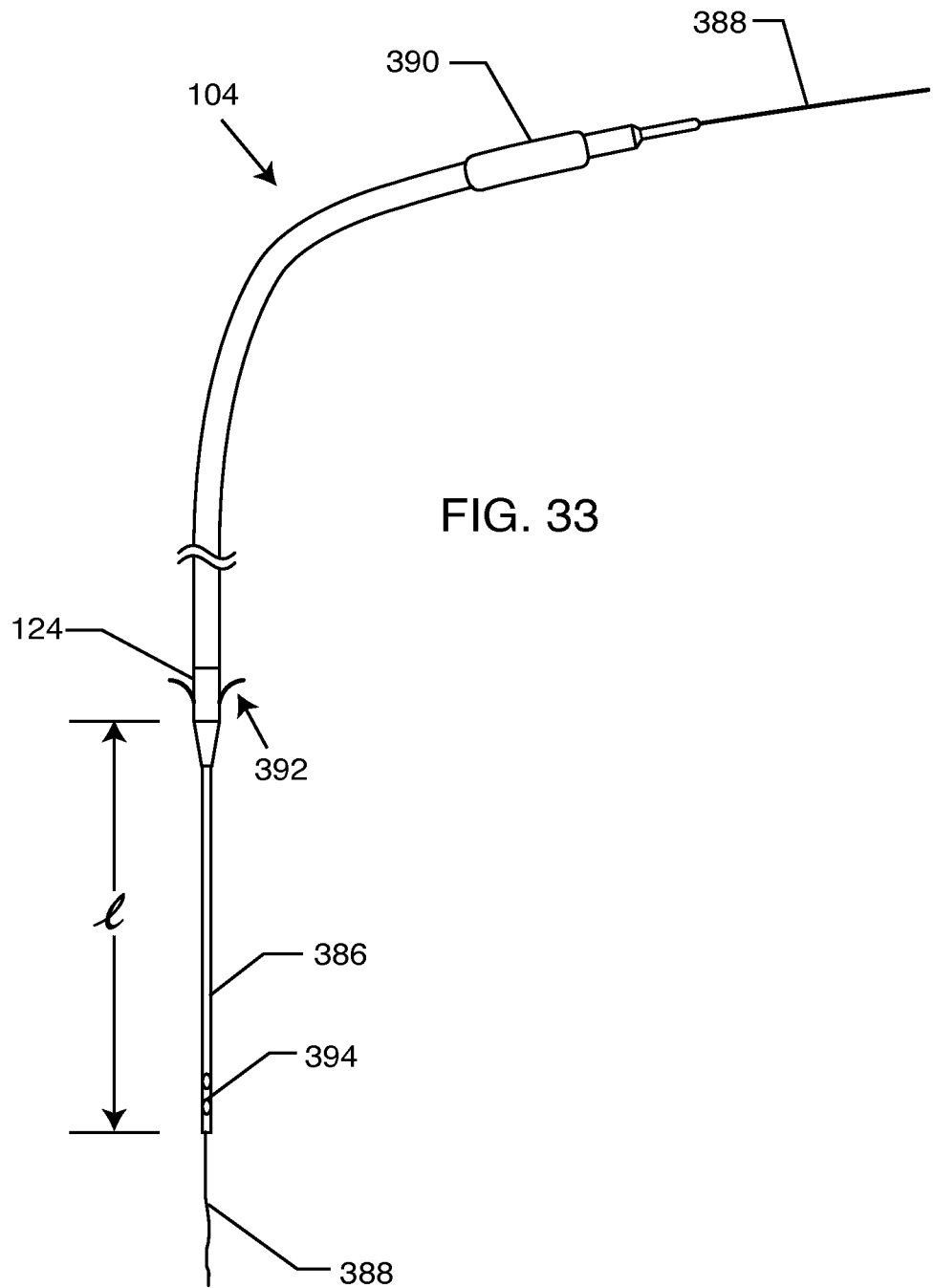
FIG. 33 is an enlarged perspective view of the lead system of FIG. 31.

FIG. 33 is an enlarged perspective view of the lead wire system 104 of FIG. 31. One can see that there is a guide wire 388 which is common in the prior art for inserting into position prior to sliding the lead wire system 104 down over it. A terminal pin 390 is designed to plug into the implantable medical device, such as a pacemaker or ICD. The electronic switch 124 is shown at the point where the lead wire 104 would be reduced from 6-9 French down to 3-6 French. Optional fixation tines 392 are shown which may be affixed to the electronic switch 124. By way of reference, the French scale is related to both diameter in millimeters (mm) or inches. For example, 7 French is 2.3 mm (0.092 inch) in diameter and 3 French is only 1 mm in diameter (0.039 inch). The length (l) of the reduced diameter lead wire section 386 can be adjusted in accordance with the branch vein into which the lead system is being inserted in the desired location of the electrodes 394. Below the electrodes 394 is the other end of the guide wire 388. Once the electrodes 394 are in the proper position and the system has been tested, the guide wire 388 is typically removed. A particular advantage of the lead system 104 as shown in FIGS. 32 and 33 is that no new deployment instruments or catheters are required. In other words, this system that includes the novel electronic switch 124 is backwards compatible with all known deployment systems. It is also very important that the lead wire system 104 is designed to be extracted in the case of a broken lead, defective lead or infected lead. The lead wire system illustrated in FIG. 33, is also backwards compatible with current (prior art) mechanical and laser lead extraction technologies.

Figure 34:
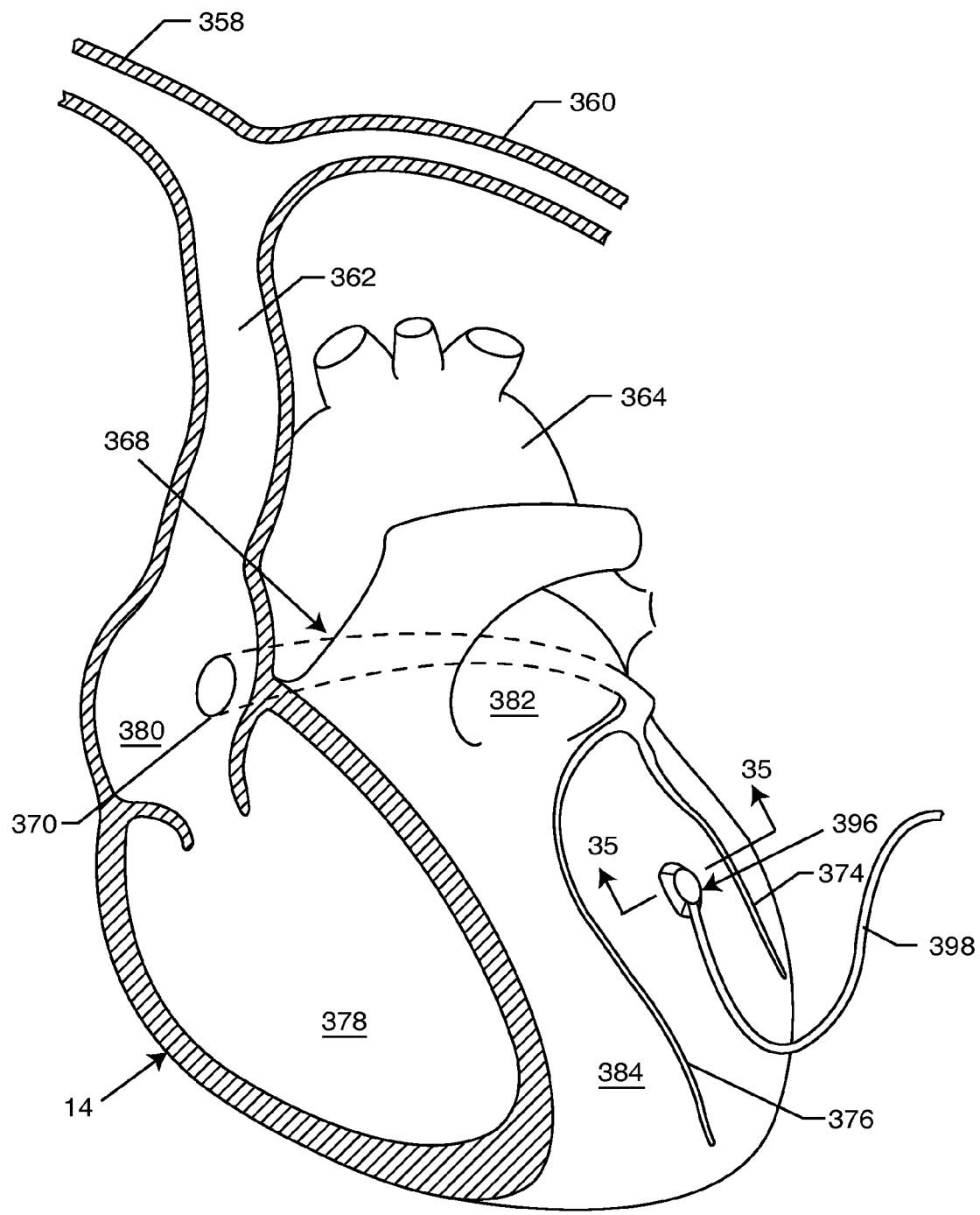
FIG. 34 is a diagrammatic representation of the human heart, showing epicardial lead wire attachment to the outside of the left ventricle in accordance with the present invention.

FIG. 34 is a diagrammatic representation of the human heart 14 similar to that illustrated in FIG. 31. However, in this case, external (epicardial) electrodes 396 are attached outside and to the left ventricle 384 by means of epicardial leads 398. A sutureless myocardial lead 398 is shown affixed to the outside of the left ventricle 384. This methodology is well known and generally involves an insertion between the ribs outside of the heart and a screwdriver type feature to affix the sutureless epicardial lead tip electrode 396 in place. Epicardial leads may also have a suture feature which is also well known in the art, which can have a helical or other configuration type tip. It will be obvious to those skilled in the art that the present invention can be extended to any type of external (epicardial) electrode or satellite pacer affixed to the outside of the heart, particularly outside of the left ventricle.

Figure 35:
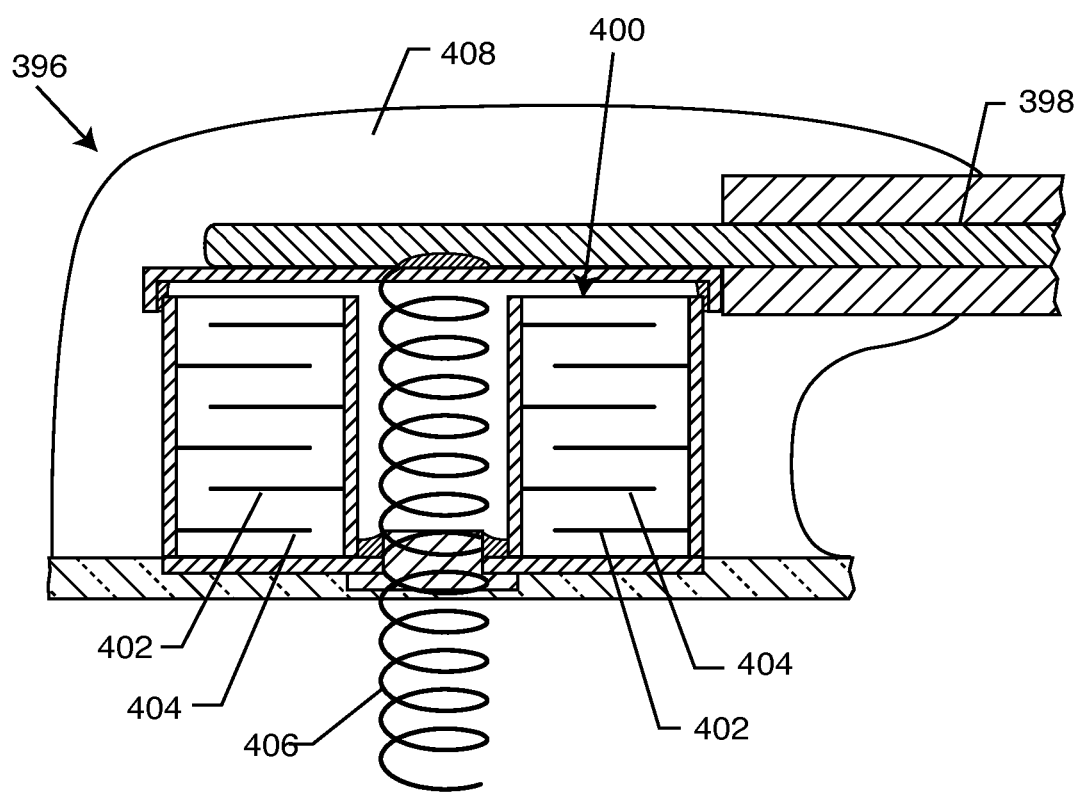
FIG. 35 is a cross-sectional view of an epicardial lead incorporating the electronic switch of the present invention taken generally along the line 35-35 in FIG. 34.

FIG. 35 is a cross-sectional view taken generally along line 35-35 of FIG. 34, illustrating an epicardial lead electrode assembly 396 which includes an electronic switch 400. In this case, the electronic switch is shown in a MEMS coaxial structure with multiple cantilevers 402 and 404 as shown. This will be useful in high voltage or high current applications such as for an ICD. Other types of MEMS switches or electronic switches can be easily adapted to this device. The electrode 396 includes a helix electrode 406 designed for insertion into body tissue. In the prior art, the epicardial lead electrode assembly 396 is typically over-molded with silicone rubber 408. The assembly shown in FIG. 35 is self-affixing to the myocardial tissue by a helical electrode structure 406. Typically this electrode is affixed into the myocardium by 3½ mechanical turns and is made of platinum-iridium alloy or equivalent biocompatible material. The helical electrode tip 406 is affixed into the myocardial tissue by a screwdriver type turning surgical tool. It can be seen that the helical electrode 406 is electrically connected to both the anode cantilevers as well as the cathode cantilevers 404 so as to be in electrical series therewith.

Figure 36:
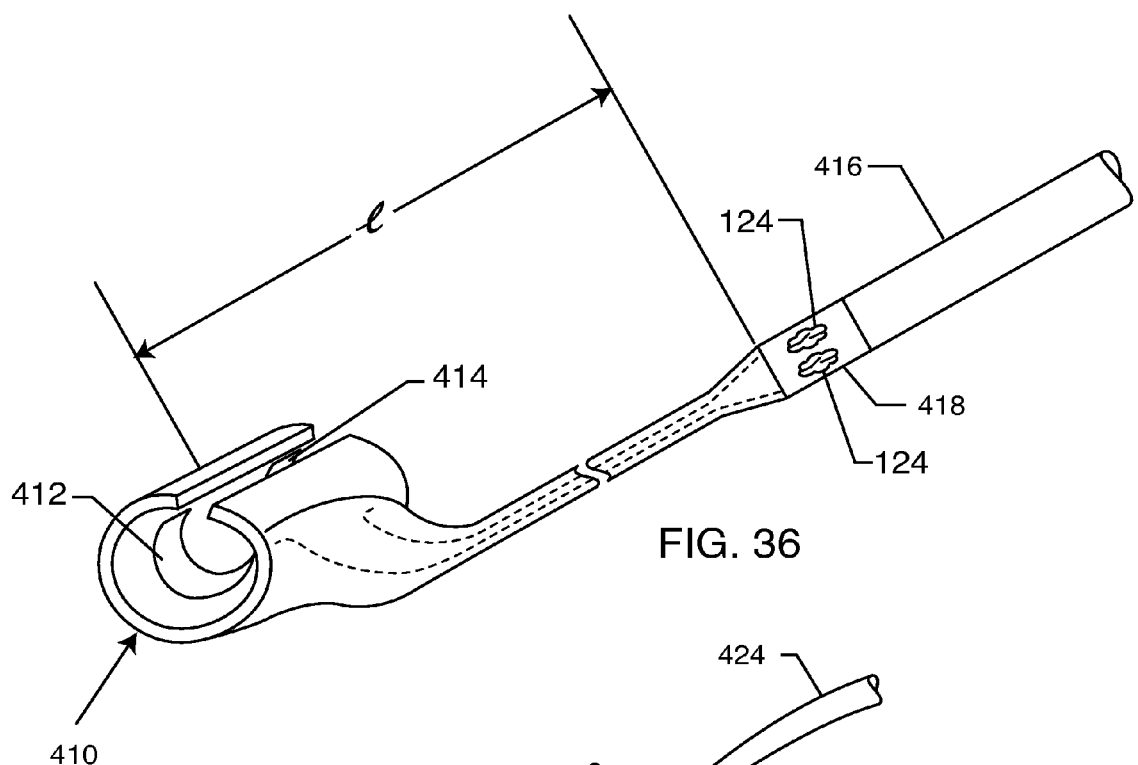
FIG. 36 illustrates a split cylinder cuff electrode designed to wrap around a nerve which incorporates electronic switches of the present invention.

FIG. 36 illustrates a split cylinder cuff electrode 410 embodying two electrodes, anode 412 and cathode 414. This is designed to be inserted by a physician around a nerve. It is a bipolar system typically consisting of a 6 to 8 French diameter lead body 416. A double electronic switch module 418 (two discrete electronic switches 124 in parallel) otherwise known in the art as a double pole-single throw switch (DPST) is used in accordance with the present invention is located as shown. In general, the cuff 410 is sized to match the diameter of the nerve which passes through its center. The lead body 416, after the double electronic switch 418, is of a reduced diameter, generally in the 3 to 4 French range. Not shown is a closing suture which is typically used to draw the cuff together after it's installed.

Figure 37:
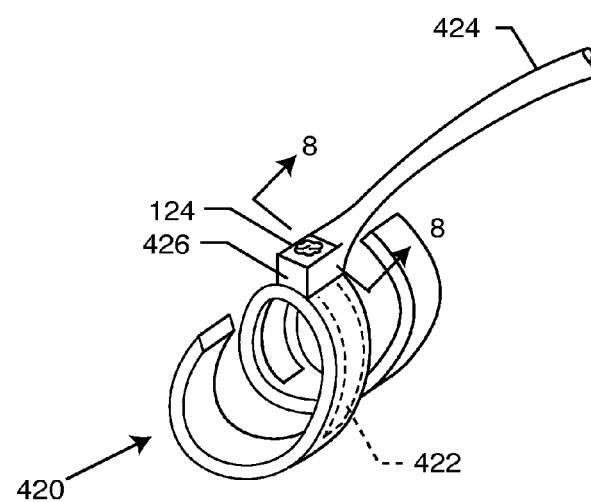
FIG. 37 illustrates a self-sizing helical cuff coil incorporating one or more electronic switches, in accordance with the present invention.

FIG. 37 illustrates helical nerve cuffs 420 which are self-sizing. These incorporate electrode foils 422 which are well known in the prior art. The lead body 424 is attached to an electronic switch module 426 of the present invention. This can be unipolar or bipolar. The electrode foil 422 can either be etched or stamped and then the termination point where the conductor attaches to the foil is either prepared or fabricated. This is the location to where the electronic switch 426 is electrically attached and incorporated. The conductors and the foil 422 on the electronic switch 426 are laid into a split mold and assembled and then silicone is injected into the mold. FIG. 37 illustrates one leg of a bipolar or multipolar lead. Obviously, an electronic switch 124 would be required for each electrode foil 422 in the multipolar configuration.

Figure 38:
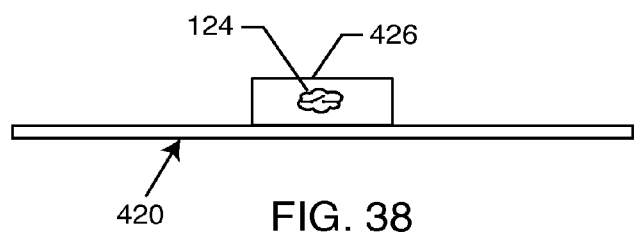
FIG. 38 is a sectional view taken generally along the line 38-38 in FIG. 37.

FIG. 38 is an enlarged sectional view taken generally along line 38-38 of FIG. 37.

Figure 39:
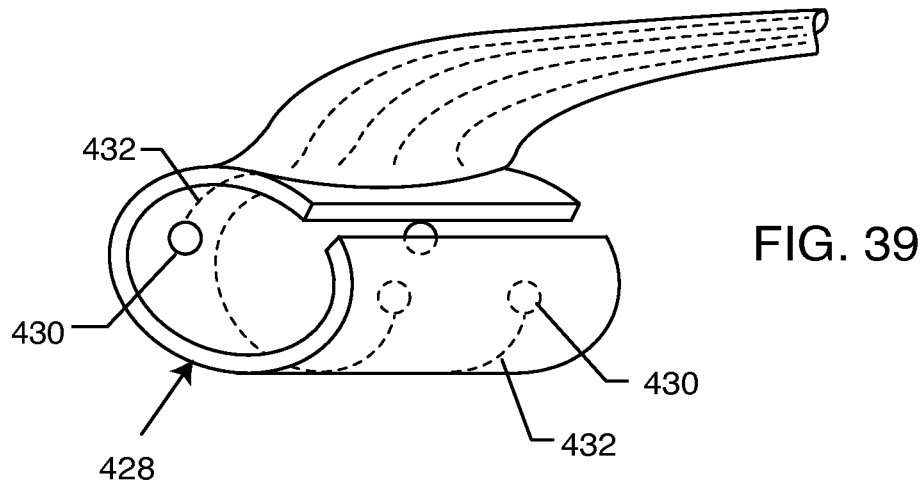
FIG. 39 illustrates a nerve cuff employing a multiplicity of electrodes and electronic switches for a large nerve trunk, in accordance with the present invention.

FIG. 39 illustrates a larger multiple cuff nerve electrode 428 for current steering in a large nerve trunk. Various electrodes can be stimulated by trial and error to obtain the optimal result. For example, for pain control, one can try various electrodes and various types of electrical stimulation by trial and error until pain is minimized or eliminated. The multiple parallel electronic switches 430, similar to that described previously, can be placed in conjunction with each one of the electrodes 432 as shown.

Figure 40:
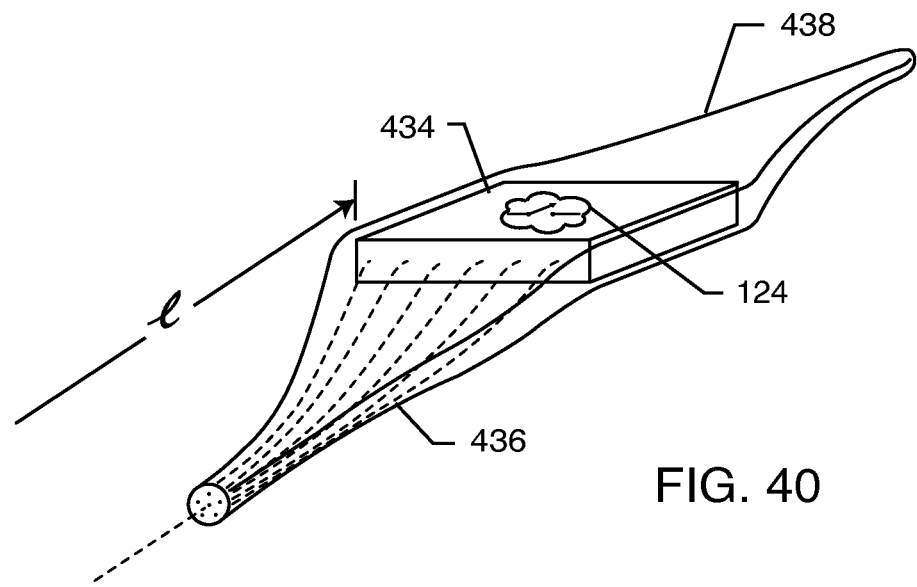
FIG. 40 illustrates one methodology of putting multiple electronic switches in series with each of the lead wires of the multiple cuff electrode of FIG. 39.
Figure 41:
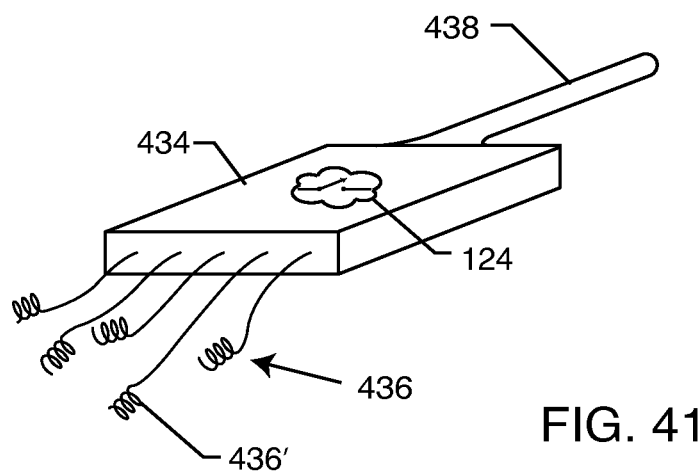
FIG. 41 illustrates a multi-conductor lead body connected to a multiple electronic switch array that has multiple electrodes, in accordance with the present invention.

FIG. 40 illustrates an alternative in that a multiple electronic switch array 434 is shown in series with the lead bodies 436 and 438. This can be built as an integrated circuit, hermetic package or other technologies which are well known in the prior art. This can in turn be connected to the cuff electrode 428 as previously described in FIG. 39 or to the multiple cuff electrodes 410 and 420 as previously illustrated in FIGS. 36 and 37. It can also be adapted to the multiple single electrodes 436 as illustrated in FIG. 41. The multiple electronic switches 434 as illustrated in FIGS. 40 and 41 can be made in a variety of ways from any of the technologies that are known in the prior art. This is accomplished by putting the devices on a substrate next to each other and arranged so that they are in series with each lead wire. The structures as illustrated in FIGS. 40 and 41 can be over-molded with silicone, glass or the like to provide reliable protection against body fluid and mechanical attachment.

Figure 42:
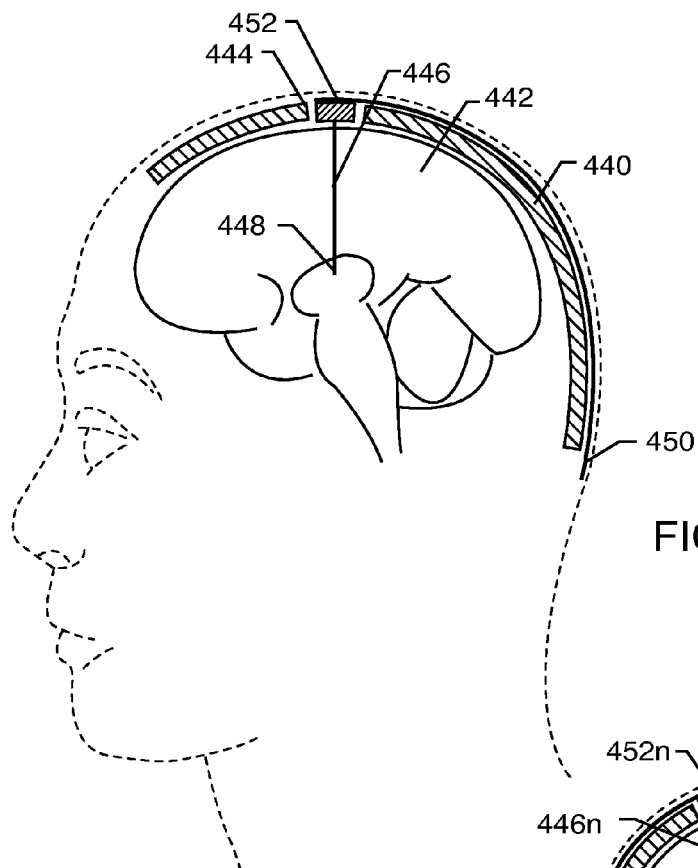
FIG. 42 is a diagrammatic, side cross-sectional view of a human head showing the placement of a deep brain probe and electrode incorporating electronic switches in accordance with the present invention.

FIG. 42 is a diagrammatic cross-sectional view of the human head, showing the skull 440 and the brain 442. A burr hole 444 is drilled through the skull 442 for placement of deep brain probe 446 with associated electrodes 448. One can see that there is a lead wire body 450 which has been tunneled up underneath the skin and attaches to the deep brain probe 446. One or more electronic switches 452 of the present invention are incorporated into the brain probe 446, electrodes 448, or lead wire body 450.

Figure 43:
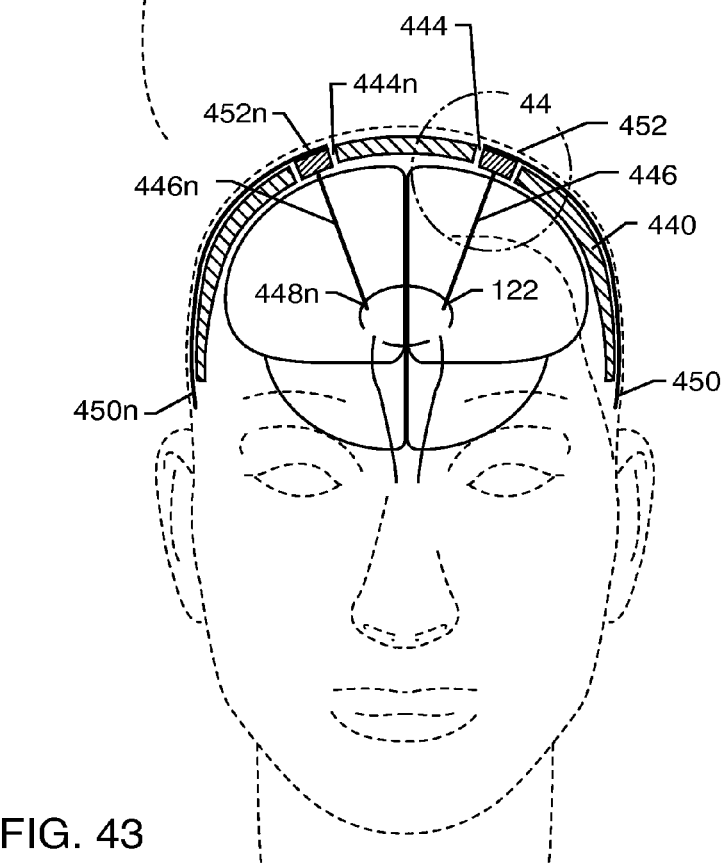
FIG. 43 is a diagrammatic, front cross-sectional view of the human head showing use of multiple deep brain probes which incorporate an electronic switch of the present invention.

FIG. 43 is a diagrammatic cross-sectional front view of the human head, showing that there can be multiple deep brain probes 446 . . . 446$_n$ placed as previously described in connection with FIG. 42. In a preferred embodiment, the top of the deep brain probe 446 and associated electronic switches 452 would be flush with the top of the skull 440. The lead wire 450 is generally connected to a pulse generator or transmitter (not shown) which is either implanted or can sit outside the skin. There can also be a receiver (not shown) which typically sits on the skin. The deep brain probe 446 can also have a nail head or nail shank.

Figure 44:
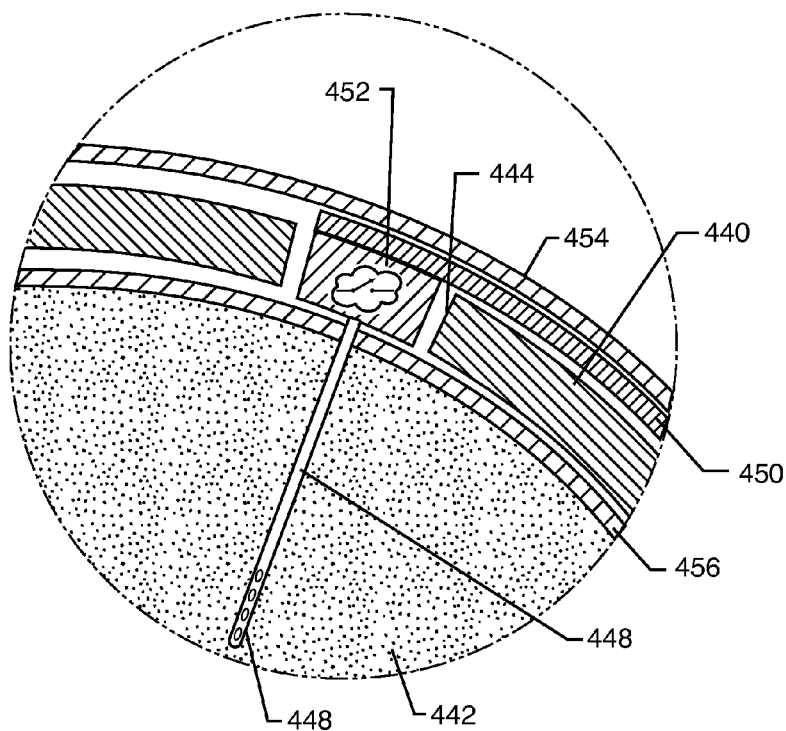
FIG. 44 is an enlarged sectional view taken generally of the area illustrated by the line 44-44 in FIG. 43.

FIG. 44 is an elongated sectional view of the area indicated by line 44 in FIG. 43, of the deep brain probe 448. Shown is the location of the electronic switch assembly 452, the skin 454 which covers the skull 440, the lead wire 450, the burr hole 444, dura layer 456 and the brain 442. At the end of the deep brain probe 448 are electrodes 448.

Figure 45:
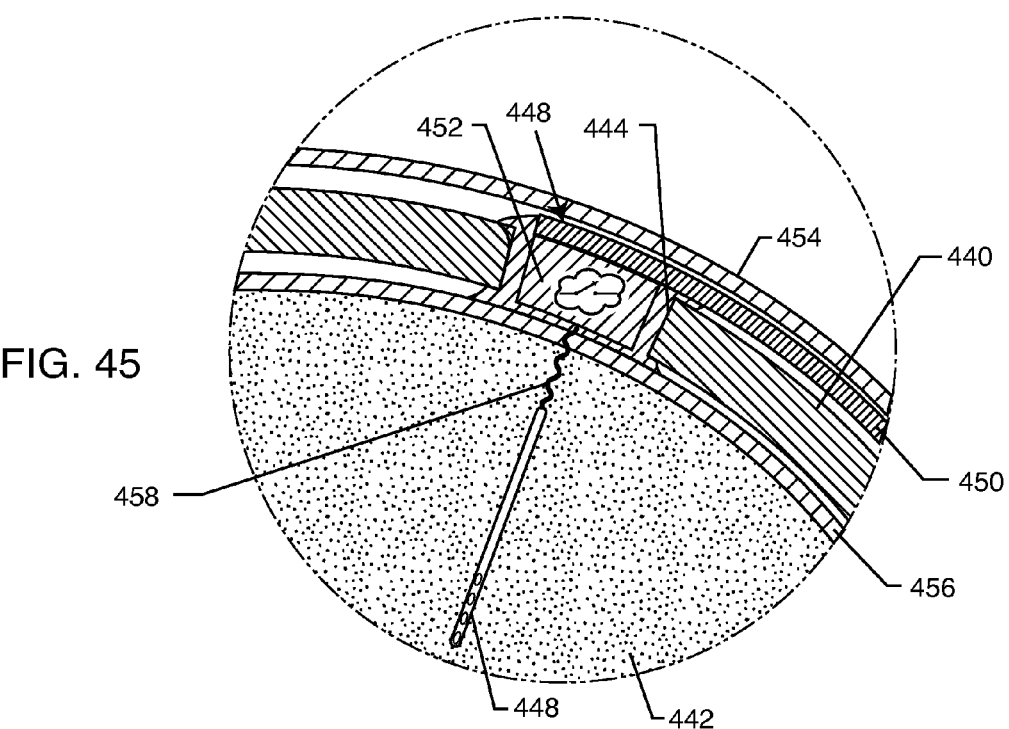
FIG. 45 is a view similar to FIG. 44, illustrating an alternative stress relieving probe in electrode arrangement.

FIG. 45 illustrates an alternative view wherein a highly flexible region 458 is connected between the electronic switch module 126 and the electrodes 448. This flexible section 458 accounts for the relative motion between the skull 440 and the brain 442.

Figure 46:
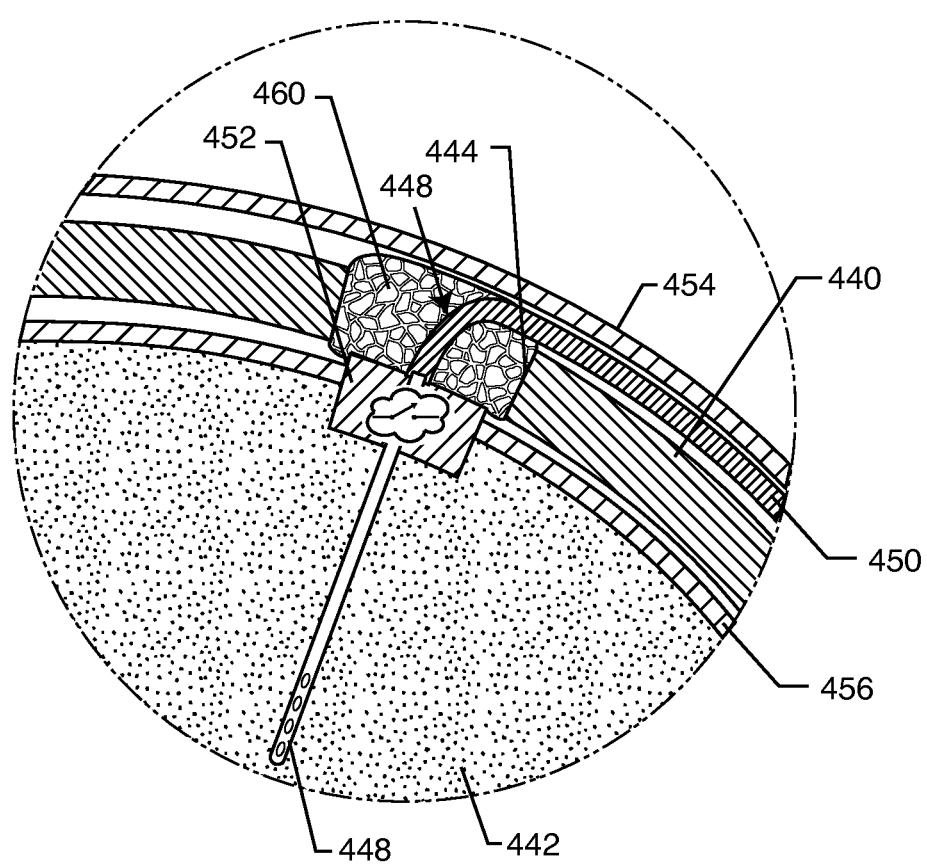
FIG. 46 is a sectional view similar to FIG. 44, except that the probe containing the electronic switch is embedded under the skull and then the skull bore hole is covered with a bone encapsulant.

FIG. 46 illustrates an alternate configuration taken from FIG. 44 wherein the top of the electronic switch module 452 is below the skull bone 440. The burr hole 444 is covered with a bone encapsulant 460. It will be obvious to those skilled in the art that the deep brain probe 448 of the present invention can be placed in various locations that are convenient for the physician/surgeon.

Figure 47:
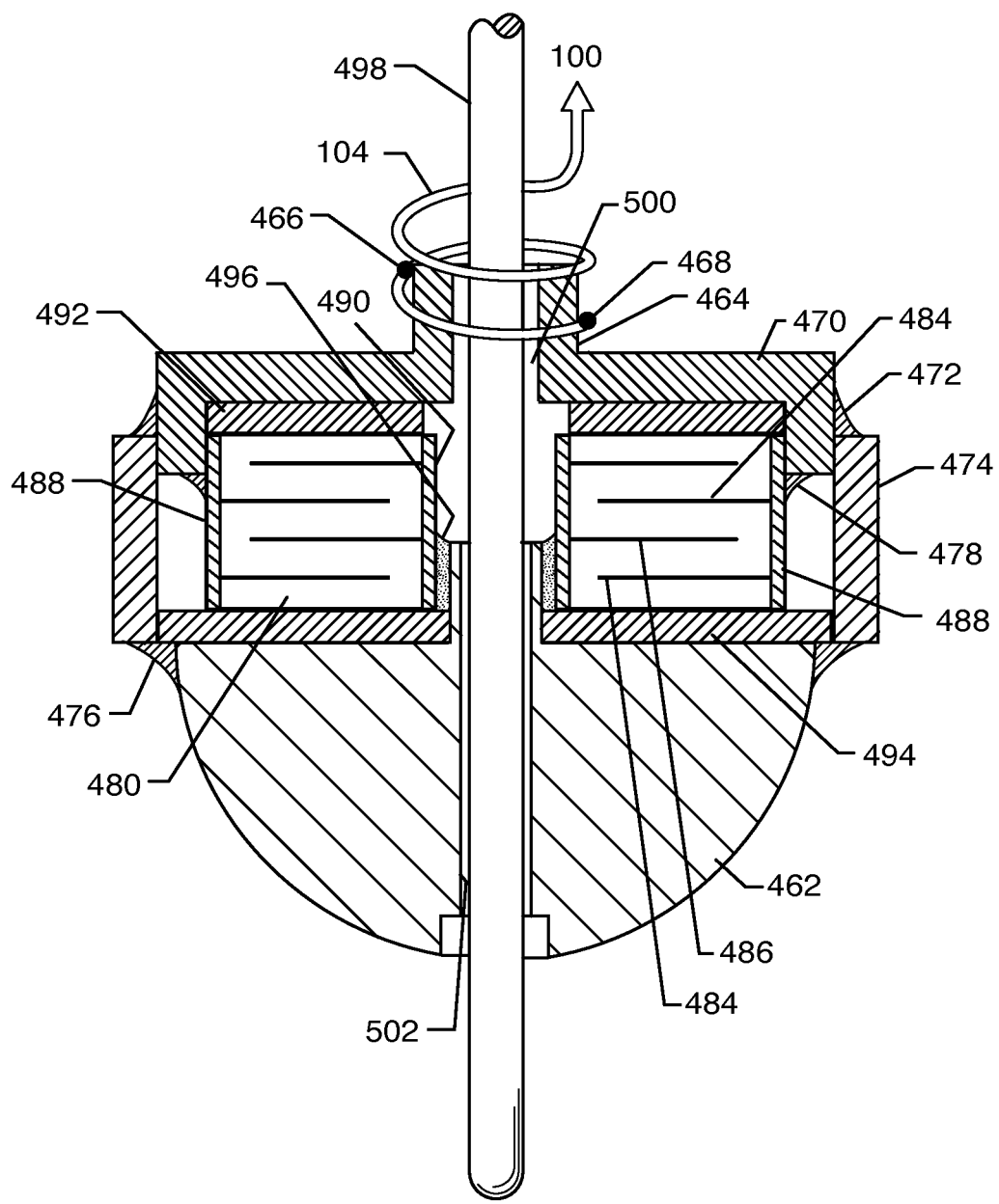
FIG. 47 is a cross-sectional view illustrating a hermetically sealed electronic switch of the present invention which has been adapted with a feedthrough hole for use with a guidewire implantation system.

FIG. 47 is a hermetic package consisting of the distal electrode trip 462 and a convenient pedestal 464 for connection of an AIMD lead wire 104. Typically the AIMD lead wire 104 is attached electrically and mechanically to the metal pedestal by laser welds 466 and 468. The metal cap 470 is typically of platinum, platinum radium, titanium or other suitable biocompatible material. A hermetic seal is formed by gold braze 472 to the insulative ceramic coaxial substrate 474. Hermetic seals are also formed at braze seal joints 476 and 478 to completely encapsulate the electronic switch assembly 480 of the present invention. In this case the electronic switch 480 is a special coaxial MEMS switch with a through hole through the center as shown. In this case there are multiple cantilevers 484 and 486 shown for high current applications. Multiple cantilevers 484 and 486 are shown for redundant circuit paths thereby allowing high currents to flow. One set connected to the outside diameter metallization 488 of the MEMS cantilevers switch contacts 484 are rigid and not free to bend. The other set of contacts 486 which are connected to the inside diameter metallization 490 are free to bend in the presence of electrostatic forces which is a principle well known in MEMS technology. The switch assembly is preferably sandwiched between insulator substrates 492 and 494 such that the metal cap 470 is electrically connected only to the outer metallization 488 and the inner metallization 490 is electrically connected to the electrode TIP 462, such as by means of conductive adhesive 496 or the like. In this manner, the electronic switch assembly 480 resides in series between the lead wire 104 and the electrode TIP 462. The novel discoidal geometry of the switch assembly 480 is new and not known in the prior art.

Referring once again to FIG. 47 one can see that there is a guide wire 498 which extends through an opening 500 of the top plate 470, through the throughhole of the switch assembly 480, and a passageway 502 of the TIP electrode 462. During implantation the physician threads the guide wire 498 through the venous system until it is in the desired location. This is a lot easier than threading the much larger diameter lead wire system. Once the guide wire 498 is suitably placed then the physician simply slips the lead system including its electrode tip 462 down over the guide wire. At this point guide wire 498 is withdrawn.

In all of the previously described embodiments, it is preferable that the electronic switches be as close to the electrode-to-tissue interface as possible. The reason for this is that lead wire systems act as transmission lines in that they have series inductance and resistance and also stray capacitance from lead to lead. This tends to cause them to decouple into various loops at MRI pulsed frequencies. It is for this reason, for example in a cardiac pacemaker, that placing an electronic switch at the housing of the cardiac pacemaker will not provide adequate cooling at the end of, for example, a 52 cm lead wire whose electrode tip is inside, for example, the right ventricle. The impedance of the lead wire would tend to decouple the electronic switch by presenting a very high impedance at the MRI RF pulsed frequencies. Accordingly, it is a feature of the present invention that the electronic switches be placed in relatively close proximity to the delivery electrodes as illustrated in the accompanying drawings.

This principle varies with the RF pulsed frequency of the MRI machine. For example, a 0.5 Tesla machine has an RF pulsed frequency of 21 MHz. In this case, the wavelength is long enough where the electronic switches could be a considerable distance away from the delivery electrode and still be quite effective. However, when one gets up around 3 Tesla with an RF pulsed frequency of 128 MHz, then the electronic switch must be much closer to the delivery electrode. This is because the impedance along the series lead wire tends to increase at higher frequencies.

Figure 48:
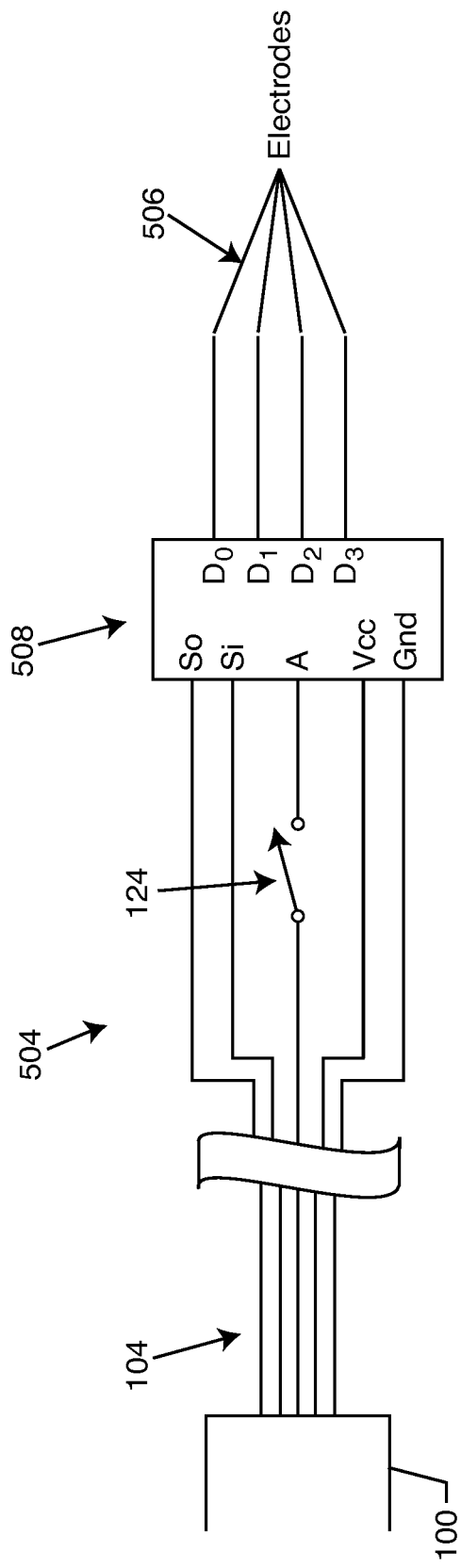
FIG. 48 is a line schematic drawing showing an electronic multiplexer which can be used to select optionally electronic switches or L-C bandstop filters.

With reference to FIG. 48, in certain AIMD applications, there can be as many as 6, 10, 12, 16 or more electrodes. There is largely a trial and error process after implantation as to which electrode pairs or which electrodes the physician will decide to use. For example, in a deep brain application, the physician will experiment using different electrodes until the desired patient responses is achieved. In a cochlear implant application, which typically uses 16 electrodes, the Audiologist will experiment with various electrodes until optimal patient hearing is achieved. A downside of these AIMDs is that a novel electronic switch would be required in series with each one of those electrodes. FIG. 48 illustrates a novel electronic multiplexing circuit 504. By way of illustration, a novel single MEMS switch 124 is shown. After the physician determines which of the multiple mini electrodes 506 is the optimal one by using the multiplexing function 508, the physician or technician can switch in the electronic switch 124 in series with that particular circuit. This has the effect of greatly reducing the number of electronic switches required.

As an alternative, instead of switching in an electronic switch, one could put a novel bandstop filter as previously described in United States Patent Application Publication Nos. US 2007/0112398 A1; US 2008/0132987 A1; US 2008/0049376 A1; US 2008/0116997 A1; and US 2006/0247684 A1, the contents of which are incorporated herein. By the use of a multiplexing network, the number of bandstop filters can be significantly reduced. Referring back to FIG. 48, one can see, if for example, there were 16 electrodes, one might need with only 4 electronic switches (or alternatively, bandstop filters consisting of a parallel inductor and capacitor element) to service selectively all 16 electrodes.

Figure 49:
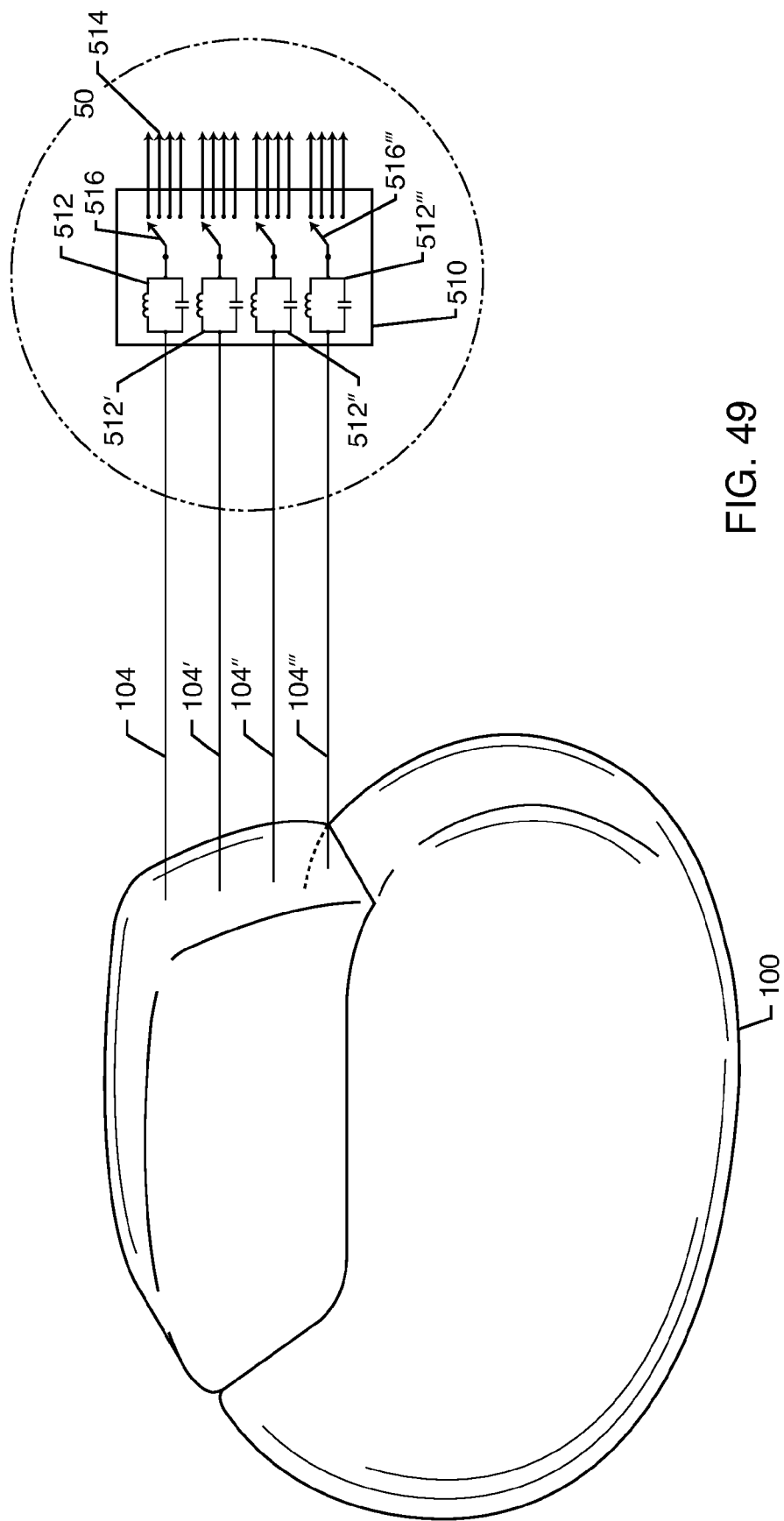
FIG. 49 is an expanded schematic illustration of the concept shown in FIG. 48.

FIG. 49 illustrates an active implantable medical device 100 such as a spinal cord stimulator. Shown are four leadwires 104 through 104''' which are routed from the spinal cord stimulator 100 to a multiplexer module 510 in accordance with the present invention. Inside of the multiplexer there are four bandstop filters 512-512'''. The bandstop filters 512-512''' consist of parallel inductor and capacitor components which are designed to be resonant at a selected frequency such as an MRI RF pulse frequency. In a preferred embodiment, the Q is selected such that they are effectively resonant with a 3 dB bandwidth over a range of pulsed MRI frequencies in the megahertz range. Also shown are 16 electrodes $514_1$-$514_{16}$ in contact with body tissue. Switches 516-516''', in this case, are single pull four throw switches. Any one of the switches can be independently switched to any one of the positions thereby connecting leadwires 104-104''' to any of the electrodes $514_1$-$514_{16}$. The switches 516-516''' have been drawn for simplicity, but it should be noted that leadwire 104 could even be routed to electrode $514_{16}$ in a more complex multiplexer circuit.

An advantage of the circuit shown in FIG. 49 is that only four leadwires are necessary to be routed from the AIMD. This is very important for either tunneling or transvenous applications where the implanted lead structure needs to be very small. It is very typical in implantable neurostimulation applications that the electrodes are inserted imprecisely but in the general anatomic region to be stimulated. It is literally a trial and error procedure during implant or after implant to find the best electrode pairs or multiple electrodes to give the best vectors. For example, in pain control, certain vectors might produce the highest level of parathesis or pain control. Another major advantage of the circuit shown in FIG. 49 is that only four (not 16) bandstop filters 512-512''' are required. This is because of the multiplexer 510 which can switch any of the bandstop filters in series with any of the electrodes. Since the other electrodes will be unused, their resonant length as an implanted lead will not be effective in coupling dangerously high levels of RF energy to body tissues.

Figure 50:
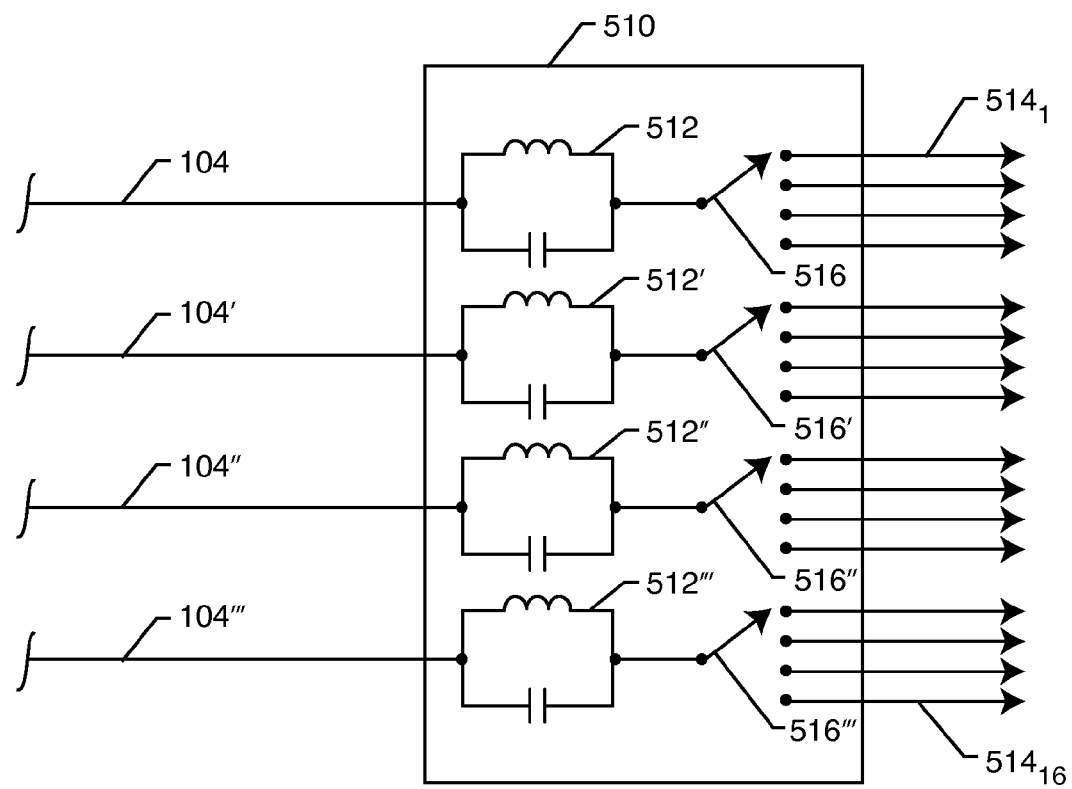
FIG. 50 is an enlarged detailed schematic illustration of the area indicated by line 50-50 from FIG. 49.

FIG. 50 is generally taken of area 50 from FIG. 49. This is a blowup of the multiplexer 510. In the bandstop filters 512-512''', an inductor and a capacitor form a parallel resonant L-C circuit. Bandstop filters are more thoroughly described in U.S. Pat. No. 7,363,090, the contents of which are incorporated herein by reference. The bandstop filter impedes the flow of induced RF current when leadwire $L_1$ from flowing into body tissues at electrode $E_1$. This provides very important protection so that body tissues are not overheated.

From the foregoing it will be appreciated that the present invention provides an MRI-compatible electronic medical therapy system which comprises (1) an active medical device (AMD) having an electronic circuit and a power supply disposed within an AMD housing, (2) a plurality of electrodes electrically connected to the electronic circuit of the AMD and adapted for insertion into or into contact with biological tissue, and (3) a multiplexer circuit including at least one, but fewer than the plurality of electrodes, bandstop filter in electrical series with the plurality of electrodes and the AMD electronic circuit. The bandstop filter is disposed exteriorly of the AMD housing and is adapted to permit current flow therethrough during normal AMD-related therapy, but substantially prevent current flow therethrough in the presence of an induced electromagnetic field, such as an MRI field.

Although several embodiments have been described in detail for purposes of illustration, various modifications may be made without departing from the scope and spirit of the invention. Accordingly, the invention is not to be limited, except as by the appended claims.

What is claimed is:

1. An MRI-compatible implantable lead extending from a proximal lead end to a distal lead portion, the implantable lead comprising:
    a) at least one lead conductor extending from a proximal lead conductor end to a distal lead conductor end, wherein the proximal lead conductor end resides at the proximal lead end and is electrically connectable to an active implantable medical device;
    b) at least two therapy delivery or sensing electrodes that are adapted for insertion into or are contactable with biological tissue, wherein the at least two electrodes are supported by the distal lead portion;
    c) at least one bandstop filter comprising a capacitance in parallel with an inductance, wherein the at least one bandstop filter is disposed physically and electrically in series with the at least one lead conductor distal the proximal lead conductor end, and wherein there are an equal number of the at least one bandstop filter as there are the at least one lead conductor, wherein there is at least one less lead conductor and bandstop filter than the at least two electrodes; and
    d) a multiplexer disposed physically and electrically in series with the at least one lead conductor proximal the at least two electrodes, wherein the multiplexer houses the at least one bandstop filter, and wherein the multiplexer provides for selectively electrically connecting the at least one lead conductor and the at least one bandstop filter to one or none of the at least two electrodes.

2. The system of claim 1, wherein the at least one bandstop filter is adapted to permit current flow therethrough when not in the presence of an induced electromagnetic field, but substantially attenuate current flow in the presence of the induced electromagnetic field.

3. The system of claim 1, wherein the induced electromagnetic field comprises an MRI RF field.

4. The system of claim 1, wherein the bandstop filter has a Q so as to resonate with a 3 dB bandwidth over a range of MRI frequencies.

5. The system of claim 4, wherein the range of MRI frequencies is in the megahertz range.

6. An MRI-compatible implantable lead extending from a proximal lead end to a distal lead portion, the implantable lead comprising:
    a) at least one lead conductor extending from a proximal lead conductor end to a distal lead conductor end, wherein the proximal lead conductor end resides at the proximal lead end and is electrically connectable to an active implantable medical device (AMD);
    b) at least two therapy delivery or sensing electrodes that are adapted for insertion into or are contactable with biological tissue, wherein the at least two electrodes are supported by the distal lead portion;
    c) at least one bandstop filter comprising a capacitance in parallel with an inductance, wherein the at least one bandstop filter is disposed physically and electrically in series with the at least one lead conductor distal the proximal lead conductor end, and wherein there are an equal number of the at least one bandstop filter as there are the at least one lead conductor, wherein there is at least one less lead conductor and bandstop filter than the at least two electrodes; and
    d) a multiplexer disposed physically and electrically in series with the at least one lead conductor proximal the at least two electrodes, wherein the multiplexer houses the at least one bandstop filter, wherein the multiplexer provides for selectively electrically connecting the at least one lead conductor and the at least one bandstop filter to one or none of the at least two electrodes; and
    e) wherein the at least one bandstop filter resonates when subjected to an induced MRI RF field so that the at least one bandstop filter permits current flow therethrough when not in the presence of the induced MRI RF field, but substantially attenuates current flow in the presence of the induced MRI RF field.

7. The system of claim 6, wherein the bandstop filter has a Q so as to resonate with a 3dB bandwidth over a range of MRI frequencies.

8. The system of claim 7, wherein the range of MRI frequencies is in the megahertz range.

9. An implantable lead extending from a proximal lead end to a distal lead portion, the implantable lead comprising:
    a) at least one lead conductor extending from a proximal lead conductor end to a distal lead conductor end, wherein the proximal lead conductor end resides at the distal lead end and is electrically connectable to an active implantable medical device;
    b) at least two therapy delivery or sensing electrodes that are adapted for insertion into or are contactable with biological tissue, wherein the at least two electrodes are supported by the distal lead portion;
    c) at least one bandstop filter comprising a capacitance in parallel with an inductance, wherein the at least one bandstop filter is disposed physically and electrically in series with the at least one lead conductor distal the proximal lead conductor end, and wherein there are an equal number of the at least one bandstop filter as there are the at least one lead conductor, wherein there is at least one less lead conductor and bandstop filter than the at least two electrodes; and
    d) a multiplexer disposed in electrical series with the lead conductor proximal the at least two electrodes, wherein the multiplexer houses the at least one bandstop filter, wherein the multiplexer provides for selectively electrically connecting the at least one lead conductor and the at least one bandstop filter to one or none of the at least two electrodes,
    e) wherein the at least one bandstop filter permits current flow therethrough when not in the presence of an induced MRI RF field, but substantially attenuates current flow in the presence of the MRI RF field, and
    f) wherein the bandstop filter has a Q so as to resonate with a 3 dB bandwidth in the megahertz range over a range of MRI frequencies.

* * * * *

UNITED STATES PATENT AND TRADEMARK OFFICE
CERTIFICATE OF CORRECTION

| | | |
|---|---|---|
| PATENT NO. | : 8,788,057 B2 | Page 1 of 1 |
| APPLICATION NO. | : 12/817030 | |
| DATED | : July 22, 2014 | |
| INVENTOR(S) | : Stevenson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 846 days.

Signed and Sealed this
Fourth Day of August, 2015

Michelle K. Lee
*Director of the United States Patent and Trademark Office*